(12) United States Patent
Nakai et al.

(10) Patent No.: US 7,445,929 B2
(45) Date of Patent: Nov. 4, 2008

(54) RECOMBINANT ADENOVIRUS VECTOR HAVING A REDUCED SIDE EFFECT

(75) Inventors: Michio Nakai, Ibaraki (JP); Kazuo Komiya, Nishinomiya (JP); Masashi Murata, Toyonaka (JP); Naoki Tohdoh, Kobe (JP); Izumu Saito, Tokyo (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 10/296,716

(22) PCT Filed: May 24, 2001

(86) PCT No.: PCT/JP01/04360

§ 371 (c)(1),
(2), (4) Date: Nov. 26, 2002

(87) PCT Pub. No.: WO01/90392

PCT Pub. Date: Nov. 29, 2001

(65) Prior Publication Data

US 2004/0091456 A1      May 13, 2004

(30) Foreign Application Priority Data

May 26, 2000    (JP)    ............................. 2000-155603
Dec. 8, 2000    (JP)    ............................. 2000-373850

(51) Int. Cl.
C12N 15/861     (2006.01)
C12N 7/01       (2006.01)
A61K 48/00      (2006.01)
A61K 31/713     (2006.01)
A01N 63/00      (2006.01)

(52) U.S. Cl. .................. 435/320.1; 424/93.2; 424/93.6; 514/44; 435/235.1

(58) Field of Classification Search .............. 435/320.1, 435/456; 424/93.2; 514/44
See application file for complete search history.

(56) References Cited

U.S. PATENT DOCUMENTS

| | | | |
|---|---|---|---|
| 5,534,015 A | | 7/1996 | Kroll et al. |
| 5,591,209 A | | 1/1997 | Kroll |
| 5,700,470 A | | 12/1997 | Saito et al. |
| 5,707,618 A | | 1/1998 | Armentano et al. |
| 5,731,172 A | | 3/1998 | Saito et al. |
| 5,824,544 A | | 10/1998 | Armentano et al. |
| 5,851,806 A | * | 12/1998 | Kovesdi et al. ........... 435/91.41 |
| 5,932,210 A | | 8/1999 | Gregory et al. |
| 6,110,744 A | * | 8/2000 | Fang et al. .................. 435/456 |
| 6,210,939 B1 | | 4/2001 | Gregory et al. |
| 6,312,946 B1 | * | 11/2001 | Yeh et al. ................. 435/320.1 |
| 6,328,958 B1 | * | 12/2001 | Amalfitano et al. ......... 424/93.2 |
| 6,461,606 B1 | * | 10/2002 | Flotte et al. ................ 424/93.2 |
| 6,630,344 B1 | * | 10/2003 | Fang et al. ............... 435/320.1 |
| 2001/0006629 A1 | | 7/2001 | Gregory et al. |
| 2001/0016192 A1 | | 8/2001 | Gregory et al. |
| 2002/0137212 A1 | | 9/2002 | Gregory et al. |

FOREIGN PATENT DOCUMENTS

| | | |
|---|---|---|
| KR | 1999-0044358 A | 6/1999 |
| WO | WO 95/11984 | 5/1995 |
| WO | WO 9613596 A1 * | 5/1996 |
| WO | WO 97/09439 A1 | 3/1997 |
| WO | WO 01/23597 A | 4/2001 |

OTHER PUBLICATIONS

De Geest, B. et al., "Elimination of Innate Immune Responses and Liver Inflammation by PEGylation of Adenoviral Vectors and Methylprednisolone", 2005, Human Gene Therapy, vol. 16: pp. 1-13.*

Schaack,, J. "Induction and Inhibition of Innate inflammatory Responses by Adenovirus Early Region Proteins", 2005, Viral Immun., vol. 18: pp. 79-88.*

Ishii, A. et al ., "Effective Adenovirus-Mediated Gene Expression in Adult Murine Skeletal Muscle", 1999, Muscle & Nerve, vol. 22: pp. 592-599.*

McGrory, W. et al., "A simple technique for the rescue of early region I mutations into infectious human adenovirus type 5", 1988, Virology, vol. 163: pp. 614-617 (Abstract Only).*

Patrice Yeh et al., "Efficient Dual Transcomplementation of Adenovirus E1 and E4 Regions from a 293-Derived Cell Line Expressing a Minimal E4 Functional Unit", Journal of Virology, vol. 70, No. 1, Jan. 1996, pp. 559-565.

Núria Morral et al., "Immune Responses to Reporter Proteins and High Viral Dose Limit Duration of Expresson with Adenoviral Vectors: Comparison of E2a Wild Type and E2a Deleted Vectors", Human Gene Therapy, vol. 8, Jul. 1, 1997, pp. 1275-1286.

M. Lusky et al., "In Vitro and In Vivo Biology of Recombinant Adenovirus Vectors with E1, E1/E2A, or E1/E4 Deleted", Journal of Virology, vol. 72, No. 3, Mar. 1998, pp. 2022-2032.

Wanda K. O'Neal et al., "Toxicological Comparison of E2a-Deleted and First Generation Adenoviral Vectors Expressing α1-Antitrypsin after Systemic Delivery", Human Gene Therapy, vol. 9, Jul. 20, 1998, pp. 1587-1598.

(Continued)

*Primary Examiner*—Michael Burkhart
(74) *Attorney, Agent, or Firm*—Sughrue Mion, PLLC

(57) ABSTRACT

The present invention provides a novel adenovirus vector for which inflammation during the in vivo administration thereof is alleviated by inhibiting the induction of expression of an adenovirus gene by a foreign promoter inserted into the adenovirus genome, and a method for producing the vector, a cell line for use in the production of the recombinant adenovirus vector, or a gene therapy method using the recombinant adenovirus vector.

17 Claims, 12 Drawing Sheets

OTHER PUBLICATIONS

Guang-Pin Gao et al., "Biology of Adenovirus Vectors with E1 and E4 Deletions for Liver-Directed Gene Therapy", Journal of Virology, vol. 70, No. 12, Dec. 1996, pp. 8934-8943.

Q Wang et al., "Persistent transgene expression in mouse liver following in vivo gene transfer with a ΔE1/ΔE4 adenovirus vector", Gene Therapy, vol. 4, 1997, pp. 393-400.

Jean-Francois Dedieu et al., "Long-Term Gene Delivery into the Livers of Immunocompetent Mice with E1/E4-Defective adenoviruses", Journal of Virology, vol. 71, No. 6, Jun. 1997, pp. 4626-4637.

Stefan Kochanek et al., "A new adenoviral vector: Replacement of all viral coding sequences with 28 kb of DNA independently expressing both full-length dystrophin and β-galactosidase", Proc. Natl. Acad. Sci., vol. 93, Jun. 1996, pp. 5731-5736.

Robin J. Parks et al., "A helper-dependent adenovirus vector system: Removal of helper virus by Cre-mediated excision of the viral packaging signal", Proc. Natl. Acad. Sci., vol. 93, Nov. 1996, pp. 13565-13570.

Manal A. Morsy et al., "An adenoviral vector delected for all viral coding sequences results in enhanced safety and extended expression of a leptin transgene", Proc. Natl. Acad. Sci. vol. 95, Jul. 1998, pp. 7866-7871.

Gudrun Schiedner et al., "Genomic DNA transfer with a high-capacity adenovirus vector results in improved in vivo gene expression and decreased toxicity", Nature Genetics, vol. 18, Feb. 18, 1998, pp. 180-183.

Núria Morral et al., "High Doses of a Helper-Dependent Adenoviral Vector Yield Supraphysiological Levels of α1-Antitrypsin with Negligible Toxicity", Human Gene Therapy, vol. 9, Dec. 10, 1998, pp. 2809-2716.

Bernard G. Huyghe et al., "Purification of a Type 5 Recombinant Adenovirus Encoding Human p53 by Column Chromatography", Human Gene Therapy, vol. 6, Nov. 1995, pp. 1403-1416.

Donna Armentano et al., "Effect of the E4 Region on the Persistence of Transgene Expression from Adenovirus Vectors", Journal of Virology, vol. 71, No. 3, Mar. 1997, pp. 2408-2416.

Douglas E. Brough et al., "Activation of Transgene Expression by Early Region 4 Is Responsible for a High Level of Persistent Transgene Expression from Adenovirus Vectors In Vivo", Journal of Virology, vol. 71, No. 12, Dec. 1997, pp. 9206-6213.

Calliope Caravokyri et al., "Constitutive Episomal Expression of Polypeptide IX (pIX) in a 293-Based Cell Line Complements the Deficiency of pIX Mutant Adenovirus Type 5", Journal of Virology, vol. 69, No. 11. Nov. 1995, pp. 6627-6633.

Kathleen M. Hehir et al., "Molecular Characterization of Replication-Competent Variants of Adenovirus Vectors and Genome Modifications To Prevent Their Occurrence", Journal of Virology, vol. 70, No. 12, Dec. 1996, pp. 8459-8467.

Valeri Krougliak et al., "Development of Cell Lines Capable of Complementing E1, E4, and Protein IX Defective Adenovirus Type 5 Mutants", Human Gene Therapy, vol. 6, Dec. 1995, pp. 1575-1586.

Guang-Ping Gao et al., "A Cell Line for High-Yield Production of E1-Delected Adenovirus Vectors without the Emergency of Replication-Competent Virus", Human Gene Therapy, vol. 11, Jan. 1, 2000, pp. 213-219.

Lee E. Babiss et al., "Promoter of the Adenovirus Polypeptide IX Gene: Similarity to E1B and Inactivation by Substitution of the Simian Virus 40 TATA Element", Journal of Virology, vol. 65, No. 2, Feb. 1991, pp. 598-605.

Bruce C. Trapnell, "Adenoviral vectors for gene transfer", Advanced Drug Delivery Reviews, vol. 12, 1993, pp. 185-199.

Nathalie Louis et al., "Cloning and Sequencing of the Cellular-Viral Junctions from the Human Adenovirus Type 5 Transformed 293 Cell Line", Virology, vol. 233, 1997, pp. 423-429.

Frits J. Fallaux et al., "New Helper Cells and Matched Early Region 1-Deleted Adenovirus Vectors Prevent Generation of Replication-Competent Adenoviruses", Human Gene Therapy, vol. 9, Sep. 1, 1998, pp. 1909-1917.

Yiping Yang et al., "Cellular immunity to viral antigens limits E1-deleted adenoviruses for gene therapy", Proc. Natl. Acad. Sci., vol. 91, May 1994, pp. 4407-4411.

Robert W. Wilmott et al., "Safety of Adenovirus-Mediated Transfer of the Human Cystic Fibrosis Transmembrane Conductance Regulator cDNA to the Lungs of Nonhuman Primates", Human Gene Therapy, vol. 7, Feb. 10, 1996, pp. 301-318.

John F. Engelhardt et al., "Ablation of E2A in recombinant adenoviruses improves transgene persistence and decreases inflammatory response in mouse liver", Proc. Natl. Acad. Sci., vol. 91, Jun. 1994, pp. 6196-6200.

Yiping Yang et al., "Inactivation of E2a in recombinant adenoviruses improves the prospect for gene therapy in cystic fibrosis", Nature Genetics, vol. 7, Jul. 1994, pp. 362-369.

Heshan Zhou et al., "Development of a Complementing Cell Line and a System for Construction of Adenovirus Vectors with E1 and E2a Delete", Journal of Virology, vol. 70, No. 10, Oct. 1996, pp. 7030-7038.

Mario I. Gorziglia et al., "Elimination of both E1 and E2a from Adenovirus Vectors Further Improves Prospects for In Vivo Human Gene Therapy", Journal of Virology, vol. 70, No. 6, Jun. 1996, pp. 4173-3178.

Q Wang et al., "A packaging cell line for propagation of recombinant adenovirus vectors containing two lethal gene-region deletions", Gene Therapy, vol. 2, 1995, pp. 775-783.

C. Caravokyri et al., "Constitutive Episomal Expression of Polypeptide IX (pIX) in a 293-Based Cell Line Complements the Deficiency of pIX Mutant Adenovirus Type 5", *Journal of Virology*, vol. 69, No. 11, Nov. 1995, pp. 6627-6633.

G.P. Linette et al., "In Vitro Priming with Adenovirus/gp100 Antigen-Transduced Dendritic Cells Reveals the Epitope Specificity of HLA-A*0201-Restricted CD8+ T Cells in Patients with Melanoma", *Journal of Immunology*, vol. 164, No. 6, Mar. 15, 2000, XP-002292685, pp. 3402-3412.

S. Miyake et al., "Efficient generation of recombinant adenoviruses using adenovirus DNA-terminal protein complex and a cosmid bearing the full-length virus genome", *Proceedings of the National Academy of Sciences of USA*, vol. 93, Feb. 1, 1996, XP 000197767, pp. 1320-1324.

D. S. Steinwaerder et al., "Insulation from viral transcriptional regulatory elements improves inducible transgene expression from adenovirus vectors in vitro and in vivo", *Gene Therapy*, vol. 7, No. 7, Apr. 2000, pp. 556-567.

R.M. Kotin, Prospects for the Use of Adeno-Associated Virus as a Vector for Human Gene Therapy, Human Gene Therapy, 1994, pp. 793-801, Mary Ann Liebert, Inc., Publishers.

R.L. Smith, et al., Characterization of Promoter Function and Cell-Type-Specific Expression from Viral Vectors in the Nervous System, Journal of Virology, Dec. 2000, pp. 11254-11261, vol. 74, No. 23.

J. Schaack, et al., Promoter Strength in Adenovirus Transducing Vectors: Down-Regulation of the Adenovirus E1A Promoter in 293 Cells Facilitates Vector Construction, Virology, 2001, pp. 101-109, vol. 291.

* cited by examiner

FIG. 3
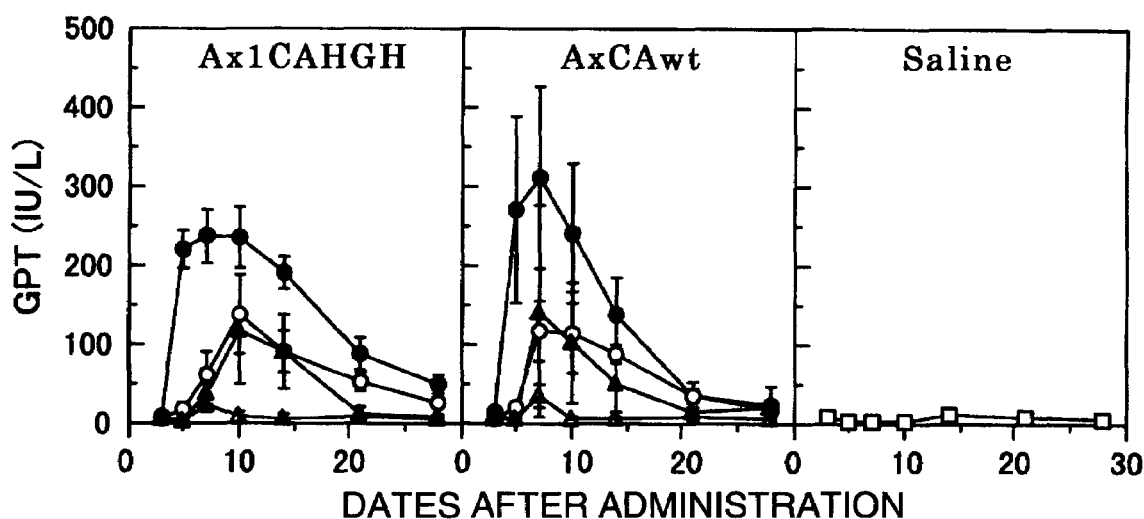
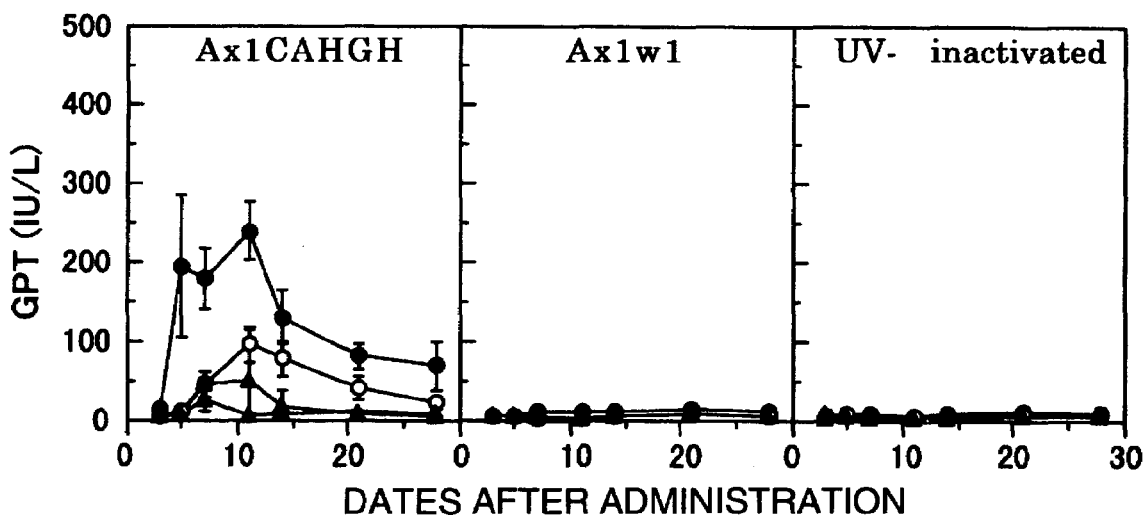

FIG. 12
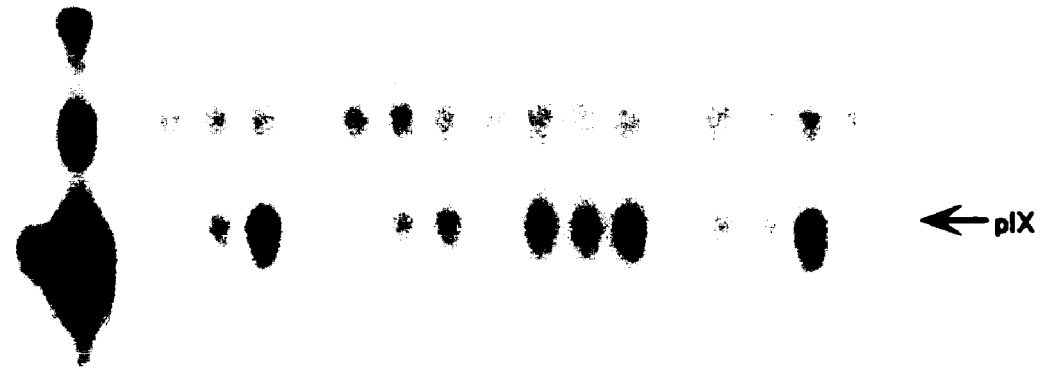

RECOMBINANT ADENOVIRUS VECTOR HAVING A REDUCED SIDE EFFECT

TECHNICAL FIELD

The present invention relates to a recombinant adenovirus vector for gene therapy and a method for producing the vector. Specifically, the present invention relates to a novel recombinant adenovirus vector for which inflammation after in vivo administration thereof is alleviated by inhibiting the induction of the gene expression of adenovirus by a foreign promoter inserted into the adenovirus genome, and a method for producing the vector, a cell line for use in the production of said recombinant adenovirus vector, or a gene therapy method using said recombinant adenovirus vector.

BACKGROUND ART

Adenovirus vectors are an excellent gene transfer vector for animal cells because of the high efficiency of gene transfer, the ability of allowing a gene to be transferred into non-dividing cells, the ease of preparing a high titer virus stock, and the like, and clinical applications thereof have been attempted as a vector for use in gene therapy. Adenovirus vectors that are widely used currently are replication-defective vectors in which the E1 gene essential for the replication of adenovirus and the expression of all adenovirus proteins has been deleted, and the vectors are termed as the first generation adenovirus vectors (some of them are further comprise the deletion of the E3 gene).

It was thought that since the first generation adenovirus vectors lack the E1 gene, none of adenovirus proteins could be expressed in normal cells such as human cells that are not expressing the E1 gene. However, recent studies have demonstrated that when a gene was transferred using a first generation adenovirus vector in vivo, expression of the transgene has been transient, and an inflammatory response occurs at the site of gene transfer (Yang Y. et al., Proc. Natl. Acad. Sci. USA 91: 4407-4411 (1994), and Wilmott R. W. et al., Hum. Gene Ther., 7: 301-318 (1996)).

As an explanation of the cause, the following hypothesis was proposed. In cells into which first generation adenovirus vectors have been infected, adenovirus early genes such as the E2A gene are expressed at low levels by transcription factors derived from cells, and thereby the adenovirus major late promoter (MLP) are activated. Subsequently, major late proteins are expressed, and cytotoxic T lymphocytes (CTL) against them are lead to generate, and CTL eliminates the foreign gene-transferred cells. Thus, it is a theory that the expression of adenovirus late proteins via the expression of adenovirus early proteins is a cause for the inflammatory response and the lack of persistent expression of the transgenes (Engelhardt J. F. et al., Proc. Natl. Acad. Sci. USA 91: 6196-6200 (1994), and Yang Y. et al., Nature Gnent., 7: 362-368 (1994)).

Based on this hypothesis, various improved adenovirus vectors were constructed in which genes essential for the replication of adenovirus other than the E1 gene were deleted, and then supplied with the proteins encoded by the genes from virus producing cells, the virus was made possible to replicate. For example, there have been reported an adenovirus vector in which the E2A gene has been deleted (Zhou H. et al., J. Virol., 70: 7030-7038 (1996), and Gorziglia M. I. et al., J. Virol., 70: 4173-4178 (1996)), an adenovirus vector in which the E4 gene which is an early gene as is the E2A gene has been deleted (Krouglicak V. et al., Hum. Gene Ther., 6: 1575-1586 (1995), and Wang Q. et al., Gene Ther., 2: 775-783 (1995), Yeh P. et al., J. Virol., 70: 559-565 (1996)), and the like. However, for adenovirus vectors in which the E2A gene has been deleted, little effect has been observed of prolonging the expression period of the transgenes and of reducing inflammatory responses (Morral N. et al., Hum. Gene Ther., 8: 1275-1286 (1997), and Lusky M. et al., J. Virol., 72: 2022-2032 (1998), and O'neal W. K. et al., Hum. Gene Ther., 9: 1587-1598 (1998)). Furthermore, it has been reported that in an adenovirus in which the E4 gene has been deleted, a moderate improvement was observed but was not satisfactory (Gao G-P. et al., J. Virol., 70: 8934-8943 (1996), Wang Q. et al., Gene Ther., 4: 393-400 (1997), and Dedieu J-F. et al., J. Virol., 71: 4626-4637 (1997)).

Thus, as a further improved vector, a helper-dependent adenovirus vector (HD vector) was proposed, in which all adenovirus genes were deleted except the inverted terminal repeat (ITR) and the packaging signal and which replicate depending on a helper virus (Kochanek S. et al., Proc. Natl. Acad. Sci. USA 93: 5731-5746 (1996), and Parks R. J. et al., Proc. Natl. Acad. Sci. USA 93: 13565-13570 (1996)). This HD vector is also termed as a gutted vector or a gutless vector. Said HD vector has been reported to exhibit an effect of improved vector such as the extension of the expression period of the transgene and reduction in inflammatory responses (Morsy M. A. et al., Proc. Natl. Acad. Sci. USA 95: 7866-7871 (1998), Schiedner G. et al., Nature Gnent. 18: 180-183 (1998), and Morral N. et al., Hum. Gene Ther. 9: 2709-2716 (1998)).

However, when this HD vector is clinically used as a pharmaceutical drug, there is a big problem of low productivity of vectors. The reason is as follows: First, in the production of HD vectors, HD vectors depend on helper adenoviruses for the supply of all proteins required for the replication as their source. From the principle of production to enable the replication of HD vectors while always maintaining the helper viruses at a constant ratio, the reported yield of HD vectors produced per cells is evidently low compared to the first generation adenovirus vectors (Morsy M. A. et al., Proc. Natl. Acad. Sci. USA 95: 7866-7871 (1998), Schiedner G. et al., Nature Gnent. 18: 180-183 (1998)). Furthermore, since the desired HD vector is always contaminated with the helper virus used for the production, the helper virus must be removed by separating the virus by ultracentrifugation based on a subtle difference in specific gravity between the viruses. Sometimes the first generation adenovirus vectors are purified by ultracentrifugation, but its purpose is to remove contaminating proteins from adenovirus particles. On the other hand, in the purification of HD vectors, not only the contaminating proteins must be removed but, as described above, helper viruses must be separated, and therefore the yield to be purified at one run of centrifugation is smaller than for the first generation adenovirus vectors. If helper viruses have not been adequately removed, the safety of viruses per se remains a concern. Furthermore, though the first generation adenovirus vectors can also be purified by the column method (Huyghe B. D. et al., Hum. Gene Ther. 6: 1403-1416 (1995)) that can handle a larger quantity of viruses than by ultracentrifugation method, the column method cannot be applied by the present state of art due to the necessity of removal of helper viruses for HD vectors. For the above reasons, the productivity of HD vectors is clearly lower than that of the first generation adenovirus vectors in both the production from cultured cells and in the subsequent purification steps. Therefore, to produce HD vectors in an amount sufficient for clinical applications is considered to be extremely difficult and is impractical.

Furthermore, since virus-derived promoters such as cytomegalovirus (CMV) promoters and Rous sarcoma virus (RSV) promoters have been widely used for vectors for gene therapy including adenovirus vectors because their promoter activities are high levels. However, it has been reported that in order to attain a long-term expression in vivo of the desired gene from these promoters, protein encoded by the adenovirus E4 gene is required (Armentano D. et al., J. Virol., 71: 2408-2416 (1997), and Brough D. E. et al., J. Virol. 71: 9206-9213 (1997)). From the standpoint of persistent promoter activity, adenovirus vectors that have inserted therein high-activity promoters derived from viruses must use vectors having a structure similar to those of the first generation adenovirus vectors.

DISCLOSURE OF THE INVENTION

It is an object of the present invention to provide a novel adenovirus vector that can replicate independently of helper viruses, said vector having a property of expressing little adenovirus protein in vivo and, as a result, of inducing no inflammatory response and enabling persistence of expression of the transgene. Furthermore, it is an object of the present invention to provide such an adenovirus vector in gene therapy.

The inventors of the present invention have made intensive and extensive study on the reasons why inflammatory responses take place when a first generation adenovirus vector in which the E1 gene has been deleted is administered to an individual animal. As a result, it was found that the mechanism by which adenovirus proteins are expressed when cells which did not produce E1 proteins were infected with a first generation adenovirus vector is different from the conventional hypothesis. Thus the inventors of the present invention have elucidated that what triggers the expression of adenovirus proteins is not the conventionally believed expression of an early gene but a foreign promoter that has been inserted into the adenovirus vector. Specifically, a new mechanism was clarified that a specific component (enhancer etc.) of the foreign promoter acts on an adenovirus promoter occurring in the vicinity of said promoter, with a result that an adenovirus gene is expressed. Besides, we have found that the mainly expressed adenovirus gene is not the major late gene that is regulated by the conventionally believed major late promoter (MLP) and that encodes hexon etc., but the protein IX gene having an independent promoter.

Protein IX is not a protein essential for the replication of adenoviruses, but required for the formation of a complete adenovirus particle. Thus, a mere deletion of the protein IX gene from the first generation adenovirus vectors does not yield a normal adenovirus vector which the present inventors desire to obtain. Accordingly, the present inventors have further carried out intensive and extensive study, and have found that said problem can be solved by two different methods. One is a method in which the protein IX gene of said adenovirus vector is relocated from the normal position to a position that does not undergo the effect of a foreign promoter (termed as the protein IX-relocated adenovirus vector). The other is a method in which the protein IX gene is deleted from said adenovirus vector, and a new cell line that produces protein IX is constructed, from which cell line a protein IX gene-deleted adenovirus vector is produced (the protein IX-deleted adenovirus vector).

Furthermore, a study by the present inventors has demonstrated that though the adenovirus gene of which expression is induced in response to the effect of a foreign promoter is mainly the protein IX gene, there is a possibility that the expression of the protein IVa2 gene and the L1 gene is also induced. Therefore, adenovirus vectors in which the promoters of the protein IVa2 gene and the L1 gene have been modified not to undergo the effect of foreign promoters can be used, either alone or in combination with the modification of protein IX gene, as a vector that does not express adenovirus proteins and that hardly induces inflammation.

The present invention has been completed based on the foregoing findings.

Thus, the present invention relates to:

1. A recombinant adenovirus vector for which inflammation during the in vivo administration thereof is alleviated, said vector having the following characteristics (1) to (4):
   (1) the E1A and the E1B genes of the adenovirus genome have been deleted;
   (2) a foreign gene containing a foreign promoter has been inserted into the adenovirus genome;
   (3) having the following characteristics (A) and/or (B):
   (A) the gene of adenovirus genome of which expression is induced by a foreign promoter has been relocated from the normal position to a position that does not undergo the induction of expression by a foreign promoter or the gene has been deleted; and
   (B) the nucleotide sequence of promoter of the adenovirus genome gene that undergoes the induction of expression by a foreign promoter has been substituted so as not to undergo the effect of the foreign promoter; and
   (4) normal virus particles having properties equal to an adenovirus wild strain have been formed,
2. A recombinant adenovirus vector according to the above 1 wherein the promoter of the adenovirus genome is MLP and/or a IVa2 gene promoter,
3. A recombinant adenovirus vector according to the above 1 or 2 having the following characteristics (5) to (8):
   (5) the E1A and the E1B genes of the adenovirus genome have been deleted;
   (6) a foreign gene containing a foreign promoter has been inserted into the adenovirus genome;
   (7) the protein IX gene of the adenovirus genome has been relocated from the normal position to a position that does not undergo the induction of expression by a foreign promoter; and
   (8) containing similar amounts of protein IX to that of the adenovirus wild strain and forming normal virus particles,
4. A recombinant adenovirus vector according to any of the above 1-3 wherein the foreign gene containing the foreign promoter has been inserted into the E1A and the E1B gene deletion sites of the adenovirus genome,
5. A recombinant adenovirus vector according to any of the above 1-4 wherein all or part of at least one gene other than the E1A and the E1B gene of the adenovirus genome has been deleted,
6. A recombinant adenovirus vector according to any of the above 3-5 wherein all or part of at least one gene other than the E1A and the E1B gene and the protein IX gene of the adenovirus genome has been deleted,
7. A recombinant adenovirus vector according to any of the above 1-6 wherein all or part of the E3 gene of the adenovirus genome has been deleted,
8. A recombinant adenovirus vector according to any of the above 1-7 wherein all or part of the E2A gene of the adenovirus genome has been deleted,
9. A recombinant adenovirus vector according to any of the above 1-8 said vector retaining at least one ORF of the E4 gene of the adenovirus genome,
10. A recombinant adenovirus vector according to the above 9 said vector retaining the ORF3 of the E4 gene of the adenovirus genome, 11. A recombinant adenovirus vector according to the above 10 wherein all or part of ORFs other than the ORF3 of the E4 gene of the adenovirus genome has been deleted,
12. A recombinant adenovirus vector according to any of the above 3-11 wherein the protein IX gene has been relocated at a position 18 kb or more apart from the foreign promoter,
13. A recombinant adenovirus vector according to the above 12 wherein the protein IX gene has been relocated to between the L3 gene and the E2A gene of the adenovirus genome,
14. A recombinant adenovirus vector according to any of the above 3-11 wherein the protein IX gene has been relocated at a position 24 kb or more apart from the foreign promoter,
15. A recombinant adenovirus vector according to the above 14 wherein the protein IX gene has been relocated at the E3 gene deletion site of the adenovirus genome,
16. A recombinant adenovirus vector according to any of the above 3-11 wherein the protein IX gene has been relocated at a position 30 kb or more apart from the foreign promoter,
17. A recombinant adenovirus vector according to the above 16 wherein the protein IX gene has been relocated to between the upstream region of the E4 gene and 3' end ITR of the adenovirus genome,
18. A recombinant adenovirus vector according to any of the above 1-17 wherein the foreign promoter contains an element derived from a mammal and/or an animal virus,
19. A recombinant adenovirus vector according to the above 18 wherein the foreign promoter contains a CMV enhancer,
20. A recombinant adenovirus vector according to the above 19 wherein the foreign promoter is a CMV promoter,
21. A recombinant adenovirus vector according to the above 19 wherein the foreign promoter is a CAG promoter,
22. A recombinant adenovirus vector according to the above 18 wherein the foreign promoter is a RSV promoter or a SRα promoter,
23. A recombinant adenovirus vector according to the above 18 wherein the adenovirus is a human adenovirus vector,
24. A recombinant adenovirus vector according to the above 23 wherein the adenovirus is a type 2 adenovirus or a type 5 adenovirus,
25. A recombinant adenovirus vector according to the above 1 or 2 having the following characteristics (9) to (11):
    (9) the E1A and the E1B genes and the protein IX gene of the adenovirus genome have been deleted;
    (10) a foreign gene containing a foreign promoter has been inserted into the adenovirus genome; and
    (11) containing similar amounts of protein IX to that of the adenovirus wild strain and forming normal virus particles,
26. A recombinant adenovirus vector according to the above 25 wherein all or part of the E3 gene of the adenovirus genome has been deleted,
27. A recombinant adenovirus vector according to the above 25 or 26 wherein the foreign gene containing the foreign promoter has been inserted into the E1A and the E1B gene deletion sites or the E3 gene deletion site of the adenovirus genome,
28. A recombinant adenovirus vector according to any of the above 25-27 wherein all or part of at least one gene other than the E1A and the E1B genes, the E3 gene, and the protein IX gene of the adenovirus genome has been deleted,
29. A recombinant adenovirus vector according to any of the above 25-28 wherein all or part of the E2A gene of the adenovirus genome has been deleted,
30. A recombinant adenovirus vector according to any of the above 25-29 said vector retaining at least one ORF of the E4 gene of the adenovirus genome,
31. A recombinant adenovirus vector according to the above 30 said vector retaining the ORF3 of the E4 gene of the adenovirus genome,
32. A recombinant adenovirus vector according to the above 31 wherein all or part of ORFs other than the ORF3 of the E4 gene of the adenovirus genome has been deleted,
33. A recombinant adenovirus vector according to any of the above 25-32 wherein the foreign promoter contains an element derived from a mammal and/or an animal virus,
34. A recombinant adenovirus vector according to the above 33 wherein the foreign promoter contains a CMV enhancer,
35. A recombinant adenovirus vector according to the above 34 wherein the foreign promoter is a CMV promoter,
36. A recombinant adenovirus vector according to the above 34 wherein the foreign promoter is a CAG promoter,
37. A recombinant adenovirus vector according to the above 33 wherein the foreign promoter is a RSV promoter or a SRα promoter,
38. A recombinant adenovirus vector according to any of the above 25-37 wherein the adenovirus is a human adenovirus vector,
39. A recombinant adenovirus vector according to the above 38 wherein the adenovirus is a type 2 adenovirus or a type 5 adenovirus,
40. A cell derived from a mammal having the following characteristics (12) and (13):
    (12) expressing the E1 gene and the protein IX gene of adenovirus; and
    (13) capable of allowing a recombinant adenovirus vector to propagate according to any of the above 25-39,
41. A cell according to the above 40 wherein the expression of the protein IX gene of adenovirus has been regulated by a foreign promoter other than the original promoter of said gene,
42. A cell according to the above 40 or 41 which further expresses at least one adenovirus gene other than the E1 gene and the protein IX gene of adenovirus,
43. A cell according to the above 42 which expresses the E1 gene, the protein IX gene, and the E2A gene of adenovirus,
44. A method of producing a recombinant adenovirus vector according to any of the above 25-39 wherein a cell according to any of the above 40-43 is used,
45. A recombinant adenovirus vector for which inflammation during the in vivo administration thereof is alleviated, said vector having the following characteristics (14) and (15):
    (14) the E1A and the E1B genes of the adenovirus genome have been deleted; and
    (15) a foreign promoter that does not induce the expression of the adenovirus gene has been inserted into the adenovirus genome,
46. A recombinant adenovirus vector according to the above 45 having the following characteristics (16) to (18):
    (16) the E1A and the E1B genes of the adenovirus genome have been deleted;
    (17) the protein IX gene of the adenovirus genome has been retained at the original position; and
    (18) a foreign promoter that does not induce the expression of the protein IX gene has been inserted into the adenovirus genome,
47. A recombinant adenovirus vector according to the above 45 or 46 wherein the foreign gene containing the foreign promoter has been inserted into the E1A gene and the E1B gene deletion sites of the adenovirus genome, 48. A recombinant adenovirus vector according to any of the above 45-47 wherein the foreign promoter dose not contain a CMV enhancer, 49. A recombinant adenovirus vector according to any of the above 45-48 wherein the foreign gene containing the foreign promoter has been inserted in the orientation toward left side, 50. A recombinant adenovirus vector according to any of the above 45-49 wherein the foreign promoter is an EF1α promoter, 51. A recombinant adenovirus vector for which inflammation during the in vivo administration thereof is alleviated, said vector having the following characteristics (19)-(21):
   (19) the E1A and the E1B genes of the adenovirus genome have been deleted;
   (20) a foreign gene containing a foreign promoter has been inserted into the adenovirus genome; and
   (21) a base sequence having a property of inhibiting the induction of the adenovirus gene expression by a foreign promoter has been inserted into between the foreign promoter and the adenovirus gene, 52. A recombinant adenovirus vector according to the above 51 wherein the foreign gene containing the foreign promoter has been inserted into the E1A gene and the E1B gene deletion sites of the adenovirus genome, 53. A recombinant adenovirus vector according to the above 51 or 52 wherein the foreign promoter contains a CMV enhancer, 54. A pharmaceutical composition which alleviates or does not induce inflammation during the in vivo administration thereof, comprising as an active ingredient a recombinant adenovirus vector selected from the above 1-39 and the above 45-53, 55. A method of alleviating inflammation during the in vivo administration, wherein a recombinant adenovirus vector selected from the above 1-39 and the above 45-53 is administered to a mammal, 56. A gene therapy method which alleviates inflammation during the in vivo administration, wherein a recombinant adenovirus vector selected from the above 1-39 and the above 45-53 is administered to a mammal, 57. The use of a recombinant adenovirus vector selected from the above 1-39 and the above 45-53 for the production of a pharmaceutical composition which alleviates or does not induce inflammation during the in vivo administration thereof, 58. The use of a recombinant adenovirus vector selected from the above 1-39 and the above 45-53 for the production of a pharmaceutical composition for use in gene therapy which alleviates or does not induce inflammation during the in vivo administration thereof.

BRIEF EXPLANATION OF THE DRAWINGS

FIG. 3 is a graph showing mean values of daily changes in serum GPT levels of C57BL/6 mice which were injected with adenovirus vectors with different structures or UV-inactivated adenovirus particles by tail vein (five mice per group). In the figure, ● is a group injected with $1 \times 10^9$ PFU, ○ is a group injected with $3 \times 10^8$ PFU, ▲ is a group injected with $1 \times 10^8$ PFU, and Δ is a group injected with $3 \times 10^7$ PFU of the vector. Saline represents a group which were injected with physiological saline, and UV-inactivated represents a group that injected with UV-inactivated adenovirus particles.

FIG. 12 is a photograph showing the result of Northern blotting of the protein IX gene of pIX-expressing cell lines. Four clones (#2, #5, #6, #10) of the pIX-expressing cell lines were subcultured to passage 30, in which for each 5 passages, RNA was prepared from the cell lines, and was subjected to Northern blotting. In the figure, P1, P5, P10, P15, P20, P25, and P30 indicate the number of passages. Three lanes on the left hand side are the negative control and the positive control. Mock represents RNA prepared from the 293 cells not in which virus, 8 hr and 24 hr represent RNA prepared from 8 hours (8 hr) and 24 hours (23 hr) after the infection of the 293 cells with Axlwl at a moi of 10.

BEST MODE FOR CARRYING OUT THE INVENTION

Figure 1:
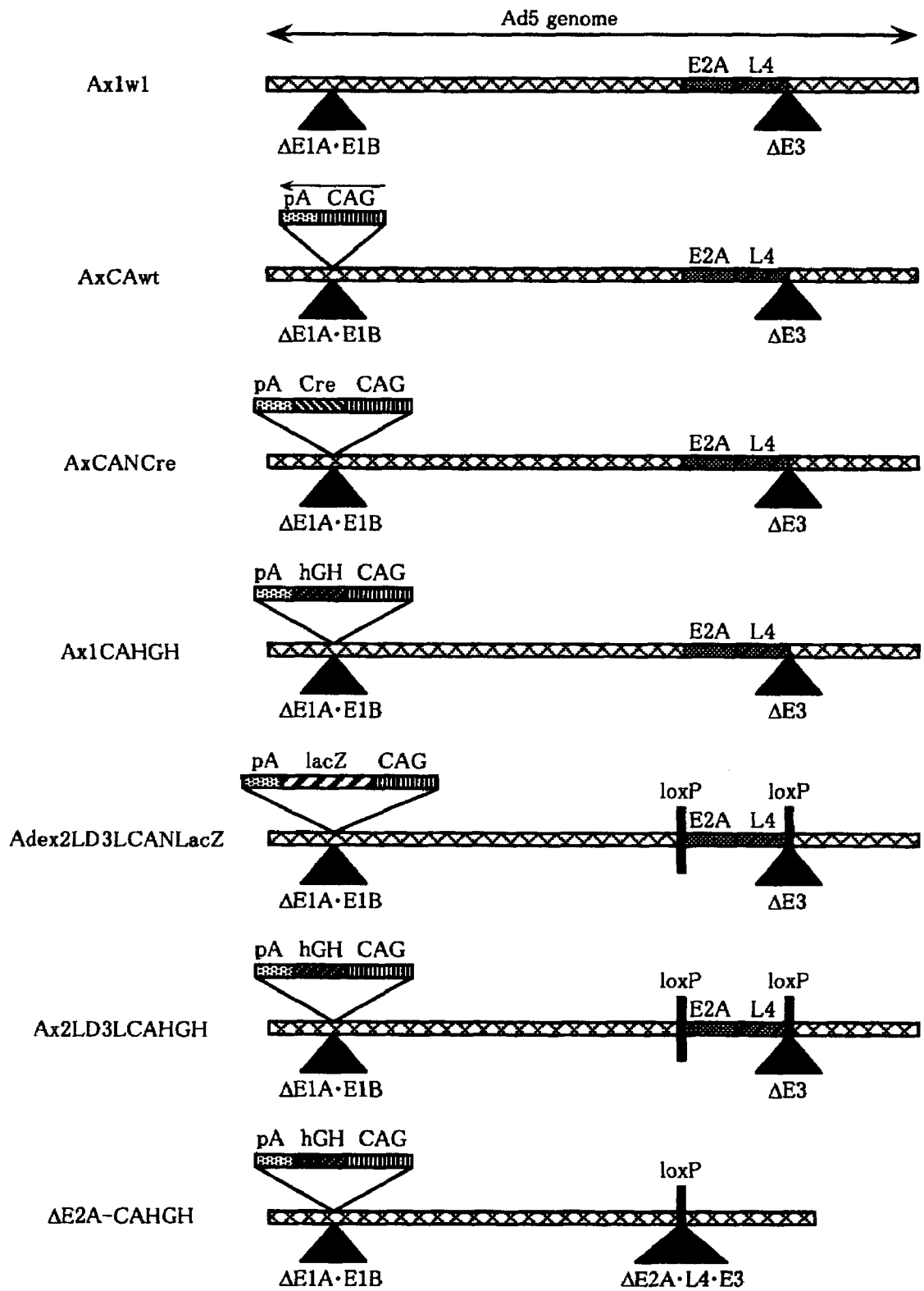
FIG. 1 is a schematic diagram showing the structure of an adenovirus vector used in the experiment. In the figure, CAG represents CAG promoter, pA represents poly(A) sequence, and an arrow above them indicates the direction of transcription. Ad5 genome represents the human adenovirus genome type 5, lacZ represents *Escherichia coli* lacZ gene, Cre represents recombinase Cre gene, and hGH represents cDNA of human growth hormone.

The present invention will now be explained in more detail hereinbelow.

In accordance with the present invention, it was revealed for the first time that inflammation that occurs after the in vivo administration of a recombinant adenovirus vector is caused by foreign promoter. Specifically, it was clarified for the first time that the gene of an adenovirus genome that should not originally be expressed is expressed by the action of a foreign promoter, and the expressed protein derived from the adenovirus causes inflammation.

Thus, in order to alleviate inflammation after the in vivo administration of an adenovirus vector, it is obvious, the genome structure of a recombinant adenovirus vector should be modified, as appropriate, so as an adenovirus gene expression is not affected by the action of the foreign promoter. Thus, the modification of the genome structure of a recombinant adenovirus vector, so as an adenovirus gene expression not to be affected by the action of a foreign promoter, could be carried out by a person skilled in the art using a standard recombinant DNA technology.

In accordance with the present invention, any of those genome structures of recombinant adenovirus vectors that have been modified so as an adenovirus gene expression not to be affected by foreign promoters are included in the category of the recombinant adenovirus vectors of the present invention.

As preferred embodiments of the recombinant adenovirus vectors of the present invention, those having the following characteristics (1)-(4) can be mentioned:
(1) the E1A and the E1B genes of the adenovirus genome have been deleted;
(2) a foreign gene containing a foreign promoter has been inserted into the adenovirus genome;
(3) having the following characteristics (A) and/or (B):
(A) the gene of an adenovirus genome of which expression is induced by a foreign promoter has been relocated from the normal position to a position that does not undergo the induction of expression by a foreign promoter or the gene has been deleted; and
(B) the nucleotide sequence of promoter of the adenovirus genome gene that undergoes the induction of expression by a foreign promoter has been substituted so as not to undergo the effect of the foreign promoter; and
(4) normal virus particles having properties equal to an adenovirus wild strain have been formed.

As used herein, an adenovirus for use in the construction of the recombinant adenovirus vector of the present invention is a virus that utilizes an animal as a natural host, and specifically a human adenovirus that utilizes a human as a host can be preferably used, and more preferably a human adenovirus of subgroup C such as human adenovirus type 2 or type 5 is used. In the present specification, in order to show the position of a gene in the adenovirus genome, map units (hereinafter referred to as m.u.; 1 m.u. is about 360 base pairs) may be used, and the values are based on adenovirus type 5. The structure of said adenovirus genome is known, and for example the entire nucleotide sequence of human adenovirus type 2 genome has been registered in GenBank (Accession No. J01949), and the entire nucleotide sequence of human adenovirus type 5 genome has been registered in GenBank (Accession No. M73260).

In the above (1), the deletion of the E1A and the E1B genes of the adenovirus means that all or part of the bases of both genes is not present, and if the deletion is such that a functional E1A protein and E1B protein are not produced, the range of deletion is not specifically limited. Furthermore, though a protein IX gene is present at a position completely overlapping with part of the E1B gene, the deletion of the E1B gene does not usually include the deletion of the protein IX gene. As examples of E1A and E1B gene deletions, there can be mentioned the deletion of 1.3-9.3 m.u. of the adenovirus type 5 (all of the E1A gene and the majority of the E1B gene are deleted; Trapnell B. C., Advanced Drug Delivery Reviews, 12: 185-199 (1993), Elsevier Science Publishing B.V.). Said deletion will be readily carried out by a person skilled in the art based on such basic textbooks as Molecular Cloning, A Laboratory Manual., T. Maniatis et al. ed., Second edition (1989), Cold Spring Harbor Laboratory.

In accordance with the present invention, the E1A gene and the E1B gene may collectively be termed simply as the E1 gene or the E1 region.

In the above (2), a foreign promoter is a promoter other than the original promoter of adenovirus, and a foreign gene is a nucleotide sequence for performing transcription comprising a promoter, a gene encoding a protein, a poly(A) sequence etc. When gene therapy is to be performed, said foreign gene refers to a gene that expresses a protein for use in treating the subject disease. A foreign gene can be readily constructed by, for example, inserting a gene encoding the desired protein into various commercially available expression vectors. Also the insertion of the constructed foreign gene into an adenovirus genome may be readily carried out based on a known method described in references (Graham F. L. et al., Proc. Natl. Acad. Sci. USA 91: 8802-8806 (1994), and Miyake S. et al., Proc. Natl. Acad. Sci. USA 93: 1320-1324 (1996), etc.). The foreign gene is preferably inserted into the above E1 gene deletion site.

In the above (3), the gene of an adenovirus genome that undergoes the induction of expression by a foreign promoter refers to a gene of the adenovirus genome the transcription of which takes place by the action of a specific component in the foreign promoter. Specifically, there can be mentioned the protein IX gene, the protein IVa2 gene, and the L1 gene and the like.

In (A) of the above (3), the gene of an adenovirus genome that undergoes the induction of expression by such a foreign promoter may be relocated from the normal position to a position that does not undergo the effect of the foreign promoter or said gene may be deleted in order to prevent the expression of said gene after in vivo administration. A specific example includes the protein IX gene. Thus, the object of the present invention of alleviating inflammation after in vivo administration can be attained. When a gene is deleted in the above, it is necessary that the gene that had been deleted should be introduced to a cell previously and the gene should be expressed in a cell that permits the replication of a recombinant adenovirus vector to form normal virus particles.

Though specific examples of such relocation or deletion of a gene will be mentioned hereinbelow in more details, basically various relocated or deleted recombinant adenovirus vectors are constructed, and evaluated on what kind of relocation or deletion can satisfy the object of the present invention by investigating the presence or absence of inflammation after in vivo administration as described in Example 5 or the Northern blotting analysis as described in Example 6, and the like.

As specific examples of genes in the above (B) of (3), there can be mentioned the major late promoter (MLP) and/or the IVa2 gene promoter. By substituting a base in the promoter of an adenovirus genome so as not to be affected by a foreign promoter to the extent that does not impair the original function, the expression of a gene under the control of the promoter of said adenovirus genome after in vivo administration can be prevented. Thus, the object of the present invention of alleviating inflammation after in vivo administration of an adenovirus vector can be attained. Specific base substitutions can be carried out as appropriate by a person skilled in the art by referring to Examples below. Thus, a recombinant adenovirus vectors having various base substitutions may be constructed, and evaluated what kind of base substitutions can satisfy the object of the present invention by investigating the presence or absence of inflammation after in vivo administration described in Example 5 or the Northern blotting analysis described in Example 6.

Specific procedures for the relocation, deletion, and substitution of adenovirus genes as described in the above (A) and (B) of (3) may be readily carried out by a person skilled in the art based on a basic textbook such as Molecular Cloning, A Laboratory Manual., T. Maniatis et al. ed., Second edition (1989), Cold Spring Harbor Laboratory, or a known technology for recombinant adenovirus construction (Graham F. L. et al., Proc. Natl. Acad. Sci. USA 91: 8802-8806 (1994), and Miyake S. et al., Proc. Natl. Acad. Sci. USA 93: 1320-1324 (1996), etc.) and the like.

In the above (4), having properties equal to an adenovirus wild strain refers to having almost the same properties as a wild strain in terms of the ratio of the composition of virus particles such as protein and physicochemical properties of virus particles, as well as the retention of infectivity to cells.

In the recombinant adenovirus vector of the present invention as mentioned above, it is possible to further delete all or part of at least one gene of the adenovirus genome other than the above E1A and E1B genes. Specifically, it is possible to delete all or part of the E3 gene, the E2A gene, and/or E4 gene. As used herein, when the E4 gene is to be deleted, it is preferred to be deleted while retaining at least one ORF of the E4 gene. In particular, deletion with at least ORF3 being retained is preferred. These deletions will be explained in detail hereinbelow.

As preferred embodiments of the recombinant adenovirus vector of the present invention, those having the following characteristics (5)-(8) can be mentioned:

(5) the E1A and the E1B genes of the adenovirus genome have been deleted;
(6) a foreign gene containing a foreign promoter has been inserted into the adenovirus genome;
(7) the protein IX gene of the adenovirus genome has been relocated from the normal position to a position that does not undergo the induction of expression by a foreign promoter; and
(8) containing similar amounts of protein IX to that of the adenovirus wild strain and forming normal virus particles.

These characteristics will now be explained in detail below taking as an example a recombinant adenovirus vector having these characteristics.

The foreign gene of the above (6) is preferably being inserted into the E1 gene deletion site. More preferably, the foreign gene has been inserted into a site in which 1.3-11.2 m.u. of the virus genome has been deleted, and a site in which all the E1 gene and the protein IX gene have been deleted (due to relocation).

The adenovirus protein IX (hereinafter referred to as pIX) of the above (7) is a minor component constituting the groups of nine hexons in the capsid of adenovirus virions, and is involved in the thermal stability of virions, and the size of virus genomes capable of being packaged. Protein IX is not an essential component for the replication of adenovirus, but virions locking pIX tend to be heat labile (Colby W. W. et al., J. Virol. 39: 977-980 (1981)), and can only package the genome DNA having a size about 90% of the wild strain (Ghosh-Choudhury G. et al., EMBO J. 6: 1733-1739 (1987)). Thus, pIX is required to form a normal virus particle.

In the above (7), that the protein IX gene of the adenovirus genome is relocated from the normal position to a position that does not undergo the induction of expression by a foreign promoter means that at a position at which protein IX gene is originally present in a wild type adenovirus genome, i.e. a position of 9.7-11.2 m.u. in the human adenovirus type 5 genome (Maat J. et al., Gene 10: 27-38 (1980)) the protein IX gene is not present, and that the protein IX gene is present at any other position of the adenovirus genome. Furthermore, that the protein IX gene does not undergo the induction of expression by a foreign promoter means that the transcription of the protein IX gene is not induced by the foreign promoter. Hereinafter, the adenovirus vector in which the protein IX gene has been relocated may be termed as "protein IX-relocated adenovirus vector."

In the above (7), the position to which the protein IX gene is relocated is not specifically limited as long as the protein IX gene does not undergo the induction of expression by a foreign promoter and the expression of protein IX is not significantly inhibited in a replication cycle of the vector. However, it is preferably that protein IX gene is relocated to a position about a few dozen kb apart from the foreign promoter and at a position at which the cloning of the foreign gene may be easily carried out. As a preferred example of such a position, there can be mentioned a position that is about 18 kb or more apart from the foreign promoter, a specific example of which includes a position between the L3 gene and the E2A gene of the adenovirus genome (Japanese Unexamined Patent Publication (Kokai) No.-308585). As another preferred example, there can be mentioned a position that is about 24 kb or more apart from the foreign promoter, a specific example of which includes a the deletion site of the E3 gene of the adenovirus genome. Furthermore, as another preferred example, there can be mentioned a position that is about 30 kb or more apart from the foreign promoter, a specific example of which includes a position between the upstream region of the E4 gene and 3' end ITR (inverted terminal repeat) of the adenovirus genome (Saito I. et al., J. Virol. 54: 711-719 (1985)). Deletion from a normal position of the protein IX gene and the relocation to the above position may be readily carried out based on a standard recombinant DNA technology and a known technology for recombinant adenovirus construction mentioned above. Whether the constructed protein IX-relocated adenovirus vector satisfy the object of the present invention can be evaluated by investigating the presence or absence of inflammation after in vivo administration described in Example 5 or the Northern blotting analysis described in Example 6 and the like.

In the above (8), a virus particle that contains similar amounts of protein IX to the adenovirus wild strain indicates an adenovirus particle that containing an almost the same ratio of protein IX as the protein IX contained in the wild type adenovirus particle. Furthermore, a normal virus particle means an adenovirus virus particle which retains infectivity to cells, and of which thermal stability and size of genomic DNA that can be packaged are almost identical to those of the wild type adenovirus.

In the above protein IX-relocated adenovirus vector, the E1A and the E1B genes can be deleted, the protein IX gene can be relocated, and furthermore all or part of the other genes of adenovirus genome can be deleted. Specifically, it is possible to delete all or part of the E3 gene, E2A gene, and/or E4 gene. As used herein the length of "all or part" is not specifically limited as long as the deletion does not permit the production of a functional protein. The nucleotide sequence of the adenovirus genome such as the above E3 gene, E2A gene, and E4 gene have been described in a reference (The Adenoviruses, Ginsberg H. S. ed., 1984, Plenum Press, New York), and a person skilled in the art can readily perform the procedure of deleting these genes from an adenovirus vector.

By deleting all or part of the E3 gene among the above genes, it is possible to insert a foreign gene having a longer size. When all or part of said E3 gene has been deleted, there is no need to express said E3 gene in a cell in which recombinant adenovirus vector is replicated. On the other hand, when all or part of the E2A gene and E4 gene has been deleted, it is necessary to introduce the deleted gene previously and allow it to be expressed in cells in which a recombinant adenovirus vector is replicated in order to form a normal virus particle.

When the E4 gene is to be deleted, it is preferred that at least one open reading frame (ORF) of the E4 gene be retained. In particular, it is preferred to retain the ORF3 of the E4 gene. In a type 5 and type 2 adenovirus, seven different polypeptides have been encoded in the E4 gene due to the difference in RNA splicing after transcription, and ORF3 is one of those polypeptides. In the multiplication cycle of the adenovirus, ORF3 has a function of promoting the expression of the virus gene and DNA replication. On the other hand, for a foreign promoter of some of CMV promoters described below to retain its promoter activity in vivo for a long term, the OR3 of the E4 gene is said to be necessary (Lusky M. et al., J. Virol. 73: 8308-8319 (1999), and Yeew N. S. et al., Hum. Gene Ther. 10: 1833-1843 (1999)). For the above reasons, it is preferred to retain said PRF3.

Cell lines that produce the protein IX-relocated adenovirus vector of the present invention are not specifically limited if they express the E1 gene and are suitable for the production of adenovirus vectors as 293 cells derived from human embryonic kidney cells (ATCC CRL-1573). However, if a homologous DNA sequence is present between an adenovirus DNA that was integrated into the chromosome of the cell line and the genome of the vector, there is a possibility that an undesirable adenovirus be generated by homologous recombination. Thus, for the production of said adenovirus vector, it is preferred to use a cell line that only contains the minimum parts of the E1 gene so that an overlapping DNA sequence may not be present as much as possible between the genome of the vector and the chromosome of the cell line. As an example, there can be mentioned PER cell lines derived from the human embryonic retina (HER) (Fallaux F. J. et al., Hum. Gene Ther. 9: 1909-1917 (1998)). In addition to the E1 gene, cell lines that express other adenovirus genes such as E2A gene may also be used as needed. A cell lines that expresses said other adenovirus gene may be constructed by, for example, transfecting an expression vector constructed by inserting said adenovirus gene into a suitable expression vector into said E1 gene-expressing cells by a standard method.

As another preferred embodiment of the recombinant adenovirus vector of the present invention, there can be mentioned an adenovirus vector in which the E1 gene and the protein IX gene have been deleted from the genome and a normal amount of protein IX is contained in said virus particles. Thus, there can be mentioned a recombinant adenovirus vector having the following characteristics (9) to (11):

(9) the E1A and the E1B genes and the protein IX gene of the adenovirus genome have been deleted;

(10) a foreign gene containing a foreign promoter has been inserted into the adenovirus genome; and

(11) containing similar amounts of protein IX to that of the adenovirus wild strain and forming normal virus particles, This vector may be termed as "protein IX-deleted adenovirus vector" hereinafter.

In the above (9), the range in which protein IX gene is deleted is not specifically limited, as long as the deletion does not permit the expression of a partial peptide of protein IX or a peptide derived from the protein IX gene. It is preferred to delete, at least, all of the coding region of the protein IX gene. Furthermore, it is more preferred to delete 1.3-11.2 m.u. of the virus genome and to delete all of the E1 gene and the protein IX gene. These deletions can be readily carried out using a standard recombinant DNA technology.

In order to produce a protein IX-deleted adenovirus vector, a cell line that expresses protein IX is needed, and said cell line is explained hereinbelow.

The foreign gene in the above (10) is preferably inserted into the E1 gene deletion site. More preferably, the foreign gene is inserted into a site in which 1.3-11.3 m.u. of the virus genome has been deleted, namely the site in which all of the E1 gene and the protein IX gene have been deleted. As in the above protein IX-relocated adenovirus vector, all or part of the adenovirus E3 gene can be deleted in the protein IX-deleted adenovirus vector as well, and it is also possible to insert a foreign gene into the E3 gene deletion site.

In the above (11), a virus particle containing similar amounts of protein IX to that of an adenovirus wild strain means an adenovirus particle containing an almost the same ratio of protein IX as the protein IX contained in the wild type adenovirus particle. A normal virus particle means an adenovirus particle that retains infectivity to cells, and has almost the same properties to the wild type adenovirus in terms of thermal stability and the size of genomic DNA that can be packaged. Said virus particle can be produced by infecting a protein IX-deleted adenovirus to a cell line that expresses protein IX and by allowing it to replicate.

For the protein IX-deleted adenovirus vector of the present invention, the E1A and the E1B genes as well as the protein IX gene can be deleted therefrom, and furthermore all or part of the other genes of the adenovirus genome can be deleted. Specific deletions are the same as for the above-mentioned protein IX-relocated adenovirus vector, and all or part of the E3 gene, E2A gene and/or E4 gene can be deleted. As used herein the length of "all or part" in which deletion is performed is not specifically limited, as long as the deletion does not permit the production of a functional protein. The nucleotide sequence of an adenovirus genome such as the above E3 gene, E2A gene, and E4 gene have been described in a reference (The Adenoviruses, Ginsberg H. S. ed., 1984, Plenum Press, New York), and a person skilled in the art can readily perform the procedure of deleting these genes from an adenovirus vector.

By deleting all or part of the E3 gene among the above genes, it is possible to insert a foreign gene having a longer size. When said E3 gene has been deleted, there is no need to express said E3 gene in cells in which a recombinant adenovirus vector is replicated. On the other hand, when all or part of the E2A gene and E4 gene has been deleted, it is necessary to introduce the deleted gene previously and allow it to be expressed in cells in which a recombinant adenovirus vector is replicated.

When the E4 gene is to be deleted, it is preferred that at least one open reading frame (ORF) of the E4 gene be retained. In particular, it is preferred to retain the ORF3 of the E4 gene. For the advantages of retaining ORF3, refer to the section of said protein IX-relocated adenovirus vector.

For the recombinant adenovirus vector of the present invention represented by the protein IX-relocated adenovirus vector and the protein IX-deleted adenovirus vector of the present invention, it is necessary to exist a foreign promoters in the vector for expressing the desired foreign gene such as a therapeutic gene. As a foreign promoter, as long as it is functional in a mammalian cell and it can express the desired gene in the desired amount, any promoter such as a animal virus-derived promoter, a mammalian cell-derived promoter, or a hybrid promoter of both promoter and the like can be used without limitation. As an example of a foreign promoter, since in many cases it is desirable to express a therapeutic gene at higher level, it is preferred to use so-called a high-expression promoter such as a CMV promoter (Foecking M. K. et al., Gene 45: 101-105 (1986)) and a CAG promoter (Niwa H. et al., Gene 108: 193-200 (1991)), and the like. The CMV promoter consists of an enhancer and a promoter of the immediate early (IE) gene of cytomegalovirus (CMV), and the CAG promoter consists of an IE enhancer of CMV, chicken β-actin promoter, a splice acceptor and poly(A) sequence of rabbit β-globin. Thus, both of the CMV promoter and the CAG promoter contain an enhancer of the IE gene of CMV (Boshart M. et al., Cell 41: 521-530 (1985)). As used herein, this enhancer of the IE gene of CMV may be termed simply as a "CMV enhancer."

As explained in Examples below, the induction of expression of the protein IX gene was noted when any of the CMV promoter and the CAG promoter which are promoters having the CMV enhancer was used. On the other hand, when the EF-1α promoter that is a promoter not containing the CMV enhancer was used, the induction of expression of the protein IX gene was not noted. Thus, it can be understood that the CMV enhancer which said CMV promoter and the CAG promoter have in common is considered to be a factor that causes the induction of expression of an adenovirus gene such as protein IX. Thus, it is thought that the CMV enhancer acts on a promoter such as protein IX gene, with a result that protein IX etc is expressed.

From the strength of promoter activity, hybrid promoters containing a CMV promoter or a CMV enhancer are used in almost all adenovirus vector which is now studying clinically. Thus, in clinical applications, the recombinant adenovirus vector of the present invention for which inflammation after in vivo administration thereof is alleviated may be used very effectively.

In addition to the above promoter containing the CMV enhancer, promoters similarly derived from viruses such as a SV40 promoter, a Rous sarcoma virus (RSV) promoter (Takebe Y. et al., Mol. Cell Biol. 8: 466-472 (1988)) can also be used.

The foreign gene to be inserted into the adenovirus vector of the present invention is not specifically limited, and a gene encoding a protein such as a cytokine, an enzyme, a receptor, a structural protein of a virus, a gene encoding an antisense RNA and a ribozyme and the like may be used.

The above protein IX-deleted adenovirus vector of the present invention, can replicate even in a cell line that expresses the E1 gene but does not express protein IX such as human embryonic kidney cells derived 293 cells. But, since a protein IX-deleted adenovirus vector produced in a cell line that does not express protein IX does not contain the desired amount of protein IX in the virus particle, it is impossible to obtain an adenovirus vector having the property of interest of the present invention. Thus, in order to produce the protein IX-deleted adenovirus vector of the present invention, a specific cell line is required that expresses at least the E1 gene and protein IX. That is, in order to allow the protein IX-deleted adenovirus vector of the present invention to replicate, mammalian cells having the following characteristics (12) and (13) is used:
(12) expressing the E1 gene and the protein IX gene of adenovirus; and
(13) capable of allowing a protein IX-deleted adenovirus vector to propagate.

As a method of constructing a cell line that expresses protein IX, a cell line already expressing the E1 gene as human embryonic kidney cells derived 293 cells (ATCC CRL-1573) may be further transformed with an expression vector containing the protein IX gene, or a cell that is not expressing the E1 gene may be sequentially or simultaneously transformed with an expression vector containing the E1 gene and an expression vector containing the protein IX gene. However, since the transformation of a cell with a DNA fragment containing all of 1.3-11.2 m.u. of E1A, E1B and protein IX gene does not give a cell line that expresses protein IX, it must be transformed with a DNA fragment to which a suitable promoter has been added upstream of the protein IX gene. Because it has been reported that 293 cells, despite nucleotide at positions 1-4344 of a human adenovirus type 5 containing the full-length of the protein IX gene has been inserted thereinto (Louis N., Virology 233: 423-429 (1997)), express very little protein IX (Krougliak V. et al., Hum. Gene Ther. 6: 1575-1586 (1995)), and, other cell lines, despite the E1 gene containing the full-length of the protein IX gene has been inserted thereinto, express very little protein IX (Fallaux F. J. et al., Hum. Gene Ther. 9: 1909-1917 (1998)). It is thought that the reason why protein IX is not expressed in these cells is that the transcription of the protein IX gene is suppressed when E1B gene is transcribing across the protein IX promoter. (Vales L. D., Genes Dev., 3: 49-59 (1989)).

With regard to a cell line that expresses the protein IX of the present invention, a promoter used for the expression of protein IX is not specifically limited, and it may be a foreign promoter or the original promoters of the protein IX gene. When a foreign promoter is used, it may be a constitutive promoter or an inducible promoter, as long as the cell line of interest can be established and maintained, and furthermore the protein IX-deleted adenovirus vector multiplied and produced in said cell line forms virus particles containing a normal amount of protein IX. Examples of a constitutive promoter include CAG promoter, CMV promoter, EF-1α promoter, SRα promoter, SV40 promoter, RSV promoter, adenovirus major late promoter (MLP), and the like. Examples of an inducible promoter include metallothionein gene promoter, mouse mammary tumor virus (MMTV) promoter, and the like. Furthermore, there can be used a system in which the expression of a constitutive promoter is induced by tetracycline or ecdysone. Expression vectors and expression-inducing systems having such a promoter are commercially available or available from public agencies. Commercial ones, if available, can be purchased from Invitrogen Inc., Clontech Inc. etc.

A cell line that expresses the above protein IX can be constructed by cloning the coding region of the protein IX gene by the PCR method, inserting this into a commercially available expression vector (for example, pcDNA3.1(+), Invitrogen Inc.), which is then introduced into the human embryonic kidney cells derived 293 cells, and allowing the cells to express protein IX. For details, see examples hereinbelow.

Furthermore, when a protein IX-deleted adenovirus vector in which a gene of adenovirus other than the adenovirus E1 gene and the protein IX gene was further deleted is to be replicated, a cell line that further expresses said deleted gene may sometimes be required. For example, when the E1 gene, protein IX gene, and the E2A gene of an adenovirus vector were deleted, a cell line that expresses these three genes is used. The E2A gene can be transduced into the cells and allowed to be expressed in a manner similar to that described for the above protein IX gene.

Methods of constructing a recombinant adenovirus vector using a cell line as described above are known to a person skilled in the art, and for example the COS-TPC method (Miyake S. et al., Proc. Natl. Acad. Sci. USA 93: 1320-1324 (1996)) may be used for the construction.

Thus, as a representative embodiment of the recombinant adenovirus vector of the present invention, a recombinant adenovirus vector having the above characteristics (1)-(4) was mentioned, and as a preferred embodiment thereof, a protein IX-relocated adenovirus vector and a protein IX-deleted adenovirus vector were illustrated and explained. As embodiments other than those described above, there can be mentioned a recombinant adenovirus vector in which a foreign promoter has been modified not to induce the expression of an adenovirus gene, or in which a foreign promoter that does not induce the expression of an adenovirus gene is used. Thus, as another preferred embodiment of the recombinant adenovirus vector of the present invention, there can be mentioned recombinant adenovirus vectors having the following characteristics (14) and (15):
(14) the E1A and the E1B genes of the adenovirus genome have been deleted; and
(15) a foreign promoter that does not induce the expression of the adenovirus gene has been inserted into the adenovirus genome.

As used herein, "a foreign promoter that does not induce the expression of the adenovirus gene" may be any promoter that does not induce at least the expression of the protein IX gene. When such a foreign promoter is used, the protein IX gene does not require the above-mentioned relocation and/or deletion, and it is only needed to be in the original position of the adenovirus genome. What kind of foreign promoter does not induce the expression of the protein IX can be evaluated by constructing a recombinant adenovirus vector in which a foreign gene containing various foreign promoters has been inserted, and investigating the presence or absence of inflammation after in vivo administration described in Example 5 or performing the Northern blotting analysis described in Example 6. Said foreign promoter does not contain at least the CMV enhancer, and specifically there can be mentioned the EF-1α promoter (Kim D. W. et al., Gene 91: 217-223 (1990)). As to the fact that said EF-1α promoter does not induce the expression of protein IX and does not induce inflammation, see Examples 8 and 9 below.

Furthermore, an expression unit containing a foreign promoter that does not induce the expression of protein IX such as said EF-1α promoter is preferably inserted in the orientation toward the left side (the reverse direction of that of transcription of the E1 gene). Because when an expression unit is inserted in the orientation toward the right side, transcription from the foreign promoter does not terminate, partly, at the normal site, and it is feared that transcription extends to the protein IX gene.

Furthermore, as another embodiment of the recombinant adenovirus vector of the present invention, there can be mentioned a recombinant adenovirus vector having the following characteristics (19)-(21):
(19) the E1A and the E1B genes of the adenovirus genome have been deleted;
(20) a foreign gene containing a foreign promoter has been inserted into the adenovirus genome; and

(21) a base sequence having a property of inhibiting the induction of the adenovirus gene expression by a foreign promoter has been inserted into between the foreign promoter and the adenovirus gene.

As used herein "a base sequence having a property of inhibiting the induction of the adenovirus gene expression by a foreign promoter" means a DNA sequence that has an activity of inhibiting the activation of the promoter of the adenovirus genome by an enhancer present in the foreign promoter. An example thereof is an insulator represented by "scs" and "gypsy" which were initially discovered in Drosophila. The insulator is a DNA sequence that prevents the activation of a promoter by an enhancer when it is located in between the enhancer and the promoter (Chung J. C. et al., Proc. Natl. Acad. Sci. USA 94: 575-580 (1997), and Bell A. C. et al., Curr. Opin. Genet. Dev. 9: 191-198 (1999)).

Thus, an adenovirus vector in which an insulator has been inserted into the right hand side (MLP side) of a foreign gene (containing enhancer/promoter) that was inserted to the E1 gene deletion site does not express adenovirus proteins including protein IX or does not induce inflammation, even when the protein IX gene is present at the original position of the adenovirus genome.

As a specific embodiment of insulators, there can be mentioned, in addition to the above-mentioned "scs" and "gypsy," an about 1.2 kb DNA fragment at the 5' HS4 site of chicken β-globin locus (Chung J. C. et al., Proc. Natl. Acad. Sci. USA 94: 575-580 (1997)), and BEAD-1 of human T cell receptor α/δ locus (Bell A. C. et al., Curr. Opin. Genet. Dev. 9: 191-198 (1999)) and the like. An insulator to be inserted into the adenovirus vector of the present invention is not specifically limited, and its origin and the size of the DNA fragment used etc. are not limited as long as the insulator has a function of not permitting the foreign enhancer/promoter to induce the gene expression of adenovirus. As an adenovirus vector in which an insulator has been inserted, there have been reported an adenovirus vector in which the above-mentioned β-globin insulator and an inducible promoter have been inserted (Steinwaerder D. S. et al., Gene Ther. 7: 556-567 (2000)), an adenovirus vector in which an insulator in the transcription stop signal of bovine growth hormone and a tissue-specific promoter have been inserted (Vassux G. et al., Gene Ther. 6: 1192-1197 (1999)), and the like. However, neither of them is intended to inhibit the gene expression of adenovirus by a foreign enhancer/promoter, but its objective is to inhibit the activation of a foreign promoter by an enhancer of the adenovirus. Thus, in the adenovirus vectors in both reports, there is no evidence that the gene expression of adenovirus by the foreign enhancer/promoter has been inhibited, and hence these reports are essentially different from the present invention in which an insulator has been inserted in order to inhibit the induction of the adenovirus gene expression and inflammation.

Then, the history of how the invention of the adenovirus vector of the present invention has been made is explained below. Thus, the history of the essence of the present invention, or the discovery that the onset of inflammation by a first generation adenovirus vector results from the induction of gene expression of adenovirus by a foreign promoter, is explained.

As used herein, the first generation adenovirus vector mean a replication-defective adenovirus vector in which the adenovirus E1 gene has been deleted. The first generation adenovirus vector is only replicable in a cell line expressing the E1 gene as 293 cells. The first generation adenovirus vector may or may not have the deletion of the E3 gene.

In order to prove the conventional hypothesis that "inflammation by the first generation adenovirus vectors is triggered by the expression of the E2A gene which is an adenovirus early gene" as has also been explained in the section of "Prior Art," the present inventors have also constructed an adenovirus vector in which the E2A gene is deleted. Since the method of constructing an E2A-deleted adenovirus vector by the present inventors has been disclosed in Japanese Unexamined Patent Publication (Kokai) No. 8-308585, the outline of the construction method is only explained herein. First, we have constructed a first generation adenovirus vector (FIG. 1, Ax2LD3LCAHGH) in which a loxP site which is a recognition sequence of recombinase Cre of the P1 phage (Abremski K. et al., J. Biol. Chem. 259: 1509-1514 (1984), and Hoess R. H. et al., Proc. Natl. Acad. Sci. USA 81: 1026-1029 (1984)) has been inserted into two sites (between the adenovirus L3 gene and the E2A gene (61.5 m.u.), and the E3 gene deletion site (78.0 m.u.)). By coinfection of 293 cells with Ax2LD3LCAHGH and the recombinase Cre-expressing first generation adenovirus vector (FIG. 1, AxCANCre), an E2A-deleted adenovirus vector (FIG. 1, ΔE2A-CAHGH) in which the E2A gene and the L4 gene flanked by two loxP sites were excised was generated. Then, by a density-gradient ultracentrifugation using cesium chloride, each virus was separated depending on the specific gravity of the virus particles to purify the E2A-deleted adenovirus vector at a purity of 97-98%. Into this E2A-deleted adenovirus vector ΔE2A-CAHGH, the expression unit thereof was inserted so that human growth hormone (hGH) could be expressed as a reporter gene under the control of the above-mentioned CAG promoter. Furthermore, as a control vector for the E2A-deleted adenovirus vector, a first generation adenovirus vector (FIG. 1, Ax1CAHGH) having the same expression unit was constructed.

The E2A-deleted adenovirus vector thus constructed was then confirmed to be deleted in the E2A gene. Thus, the expression levels of a DBP (single stranded DNA binding protein) encoded by the E2A gene in the A549 cells (human lung cancer-derived cell line) infected with either ΔE2A-CAHGH or Ax1CAHGH, was compared by the fluorescent antibody method, and the deletion of the E2A gene was confirmed since the expression of DBP was evidently decreased in the cells infected with ΔE2A-CAHGH. Furthermore, the expression levels of hexon encoded by the L3 gene, belonging to a late gene, and which is a major structural protein of the virus particle was similarly compared by the fluorescent antibody method, and it was found that the expression of hexon was evidently decreased in the cells infected with ΔE2A-CAHGH. The result indicated that the conventional hypothesis "the E2A gene expressed in trace amounts activates the adenovirus major late promoter (MLP) and thereby the major late protein is expressed" is correct on this point.

Accordingly, it was investigated whether in vivo inflammatory responses of animals injected with the E2A-deleted adenovirus vector are reduced. ΔE2A-CAHGH or Ax1CAHGH was intravenously injected into mice, and serum level of a liver released enzyme GPT (glutamic pyruvic transaminase) was measured as an index of inflammation. First, in order to confirm the efficiency of infection for each adenovirus vector, serum hGH levels three days after the administration of an adenovirus vector were measured. Since there was no significant difference in serum hGH levels between both of the adenovirus vector administration groups, the absence of difference in infection efficiency in animals between the adenovirus vectors was confirmed. Accordingly, the E2A-deleted adenovirus vector was evaluated with serum GPT levels as an index, and it was found that serum GPT levels increased in the ΔE2A-CAHGH-administered mice as same as in the Ax1CAHGH-administered mice. This result revealed that the E2A-deleted adenovirus vector had no effect of alleviating inflammation. Furthermore, in some mice, after the administration of the adenovirus vector, liver sections were prepared for histological analysis at constant intervals. In the Ax1CAHGH-administered mice, at day 5 or more after administration, there were inflammatory responses such as leukocyte infiltration into the liver including T cells and the apoptosis of hepatocytes were observed, and similar inflammatory responses were observed in the ΔE2A-CAHGH-administered mice as well. Therefore, there were also no differences histopathologically between both adenovirus vector-administered mice.

The above result indicates that the deletion of the E2A gene has no effect on the alleviation of inflammation. Thus, as reasons why there were no differences in the induction of inflammation between the E2A gene-deleted adenovirus vector and the first generation adenovirus vector, the following four possibilities were considered:

1) Adenovirus genes such as the E4 gene other than the E2A gene are directly activated by cell-derived factors, and the expressed adenovirus protein per se induces cell-mediated immunity, or induced the expression of another adenovirus protein, which protein induces cell-mediated immunity thereby leading to inflammation;
2) The hGH protein used as a reporter gene induces cell-mediated immunity thereby leading to inflammation;
3) A foreign promoter (CAG promoter) inserted into the vector acts as an enhancer on the adenovirus promoter to express an adenovirus protein, which adenovirus protein induces cell-mediated immunity thereby leading to inflammation; and
4) In stead of a protein synthesized de novo in the vector-infected cells but a protein per se constituting the adenovirus particle invading into the cell induces cell-mediated immunity thereby leading to inflammation. Alternatively, the entry per se of adenovirus particles into the cell serves as a stimulation, and induces the production of inflammatory cytokines etc., thereby leading to inflammation.

Thus, in order to clarify which of the above 1) to 4) is a possible cause of why the E2A gene-deleted adenovirus vector did not alleviated the induction of inflammation, the cause of inflammation was investigated using the following four adenovirus vectors:

(a) a first generation adenovirus vector which expresses hGH (Ax1CAHGH: positive control)
(b) a first generation adenovirus vector in which a CAG promoter has only been inserted without hGH cDNA (FIG. 1, AxCAwt: poly(A) sequence has also been inserted)
(c) a first generation adenovirus vector in which a foreign gene such as promoter has not been inserted (FIG. 1, Ax1wl)
(d) UV-inactivated adenovirus particles (Ax1CAHGH has been inactivated).

These four vectors were injected intravenously into mice and serum GPT levels were measured. Details of the definition and the method for the preparation of UV-inactivated adenovirus particles have been described in existing publications (Brinstiel M. L. et al., Proc. Natl. Acad. Sci. USA 89: 6094-6098 (1992), Birnstiel M. L. et al., Virology 205: 254-261 (1994)), of which definition is briefly described below. UV-inactivated adenovirus particles mean adenovirus particles that retain infectivity to the cells and can invade into the cells, but cannot replicate even in the cells that permit the replication of adenovirus before inactivation and that have been inactivated to a state in which the expression of the inserted foreign gene does not occur.

Summarizing the results, in the mice that treated with the UV-inactivated adenovirus particles and the mice that treated with Axlwl into which no foreign genes have been inserted, serum GPT levels were not elevated at all. On the other hand, in the mice that treated with AxCAwt in which a CAG promoter was only inserted, serum GPT levels were increased to a similar degree as the Ax1CAHGH-treated mice that express hGH. Since inflammation have also occurred in the AxCAwt-treated mice, the possibility that hGH protein of 2) is the cause was denied. Furthermore, since no inflammation occurred in mice that treated with UV-inactivated adenovirus particles, the possibility that the adenovirus particles of 4) are the cause was denied. Furthermore, since no inflammation occurred in the Axlwl-treated mice, the possibility that the cause of 1) alone causes inflammation was denied. Thus, since inflammation in the AxCAwt-treated mice has occurred to a similar degree to that in the Ax1CAHGH-treated mice, and no inflammation has occurred in the Axlwl-treated mice, and the only difference between the structure of the AxCAwt and Axlwl is the presence or absence of the CAG promoter, it was revealed that the reason of inflammation caused by the first generation adenovirus vectors is caused by the CAG promoter that was inserted into the vector of 3).

Accordingly, the adenovirus gene of which expression is induced by the CAG promoter, namely an adenovirus gene involved in inflammation were identified. An E2A-deleted adenovirus vector (ΔE2A-CAHGH) or the three first generation adenovirus vectors (Ax1CAHGH, AxCAwt, Axlwl) in the above (a) to (c) were infected to the A549 cells (human lung cancer-derived cell line) or the HepG2 cells (human hepatoma-derived cell line) at a high moi (multiplicity of infection), and after 24 hours the adenovirus genes that were expressed were analyzed by Northern blotting. The adenovirus genes of which expression were investigated are the following eight genes: early genes: E2A gene, E4 gene; major late genes under the control of the major late promoter (MLP): L1, L2, L3, L5; delayed early genes: protein IX, IVa2. The definition of the desired adenovirus, i.e., the adenovirus gene of which expression is induced by the CAG promoter and which is involved in inflammation, is a gene which, if a CAG promoter is inserted to the vector, is expressed in the cells infected with the E2A-deleted adenovirus vector (ΔE2A-CAHGH) in a similar degree as in the cells infected with the first generation adenovirus vector (Ax1CAHGH and AxCAwt), but of which expression is induced very little in the cells infected with the first generation adenovirus vector to which a CAG promoter is not inserted (Axlwl).

First, after the expression of the E2A gene was investigated, it was confirmed that the E2A gene is completely deleted in the E2A-deleted adenovirus vector used in the present invention since the E2A gene was expressed very little in the ΔE2A-CAHGH-infected cells, and the gene was expressed to almost the same degree regardless of the presence of the CAG promoter in the cells infected with the other three first generation adenovirus vectors. At the same time, it was revealed that the expression of the E2A gene is not induced by the CAG promoter. The E4 gene, another early gene, has been expressed to almost the same degree in all the cells infected with four adenovirus vectors, and thereby it was also revealed that the expression of the E4 gene is not induced by the CAG promoter either.

Next, the expression of major late genes that are controlled by MLP were investigated. Among the major late genes, the expression of three genes, L2, L3 and L5, was decreased only in the cells infected with ΔE2A-CAHGH in the HepG2 cells, and among the A549 cells, expression in the cells infected with ΔE2A-CAHGH and the cells infected with Axlwl was evidently decreased. Thus, not only at the above-mentioned protein level but also at the gene level, the conventional hypothesis "the E2A gene induces the expression of major late genes" was confirmed, but it was demonstrated that the expressions of these major late genes are not induced by the CAG promoter. Furthermore, the expression of the L1 gene varied with the cell line used. Among the HepG2 cells, the expression of the L1 gene was only decreased in the ΔE2A-CAHGH-infected cells, and no induction of expression by the CAG promoter was observed. On the other hand, among the A549 cells, the expression of the L1 gene was only decreased in the Axlwl-infected cells, and the induction of expression by the CAG promoter was observed.

Finally, the expression of delayed early genes of two genes, the IVa2 gene and the protein IX gene, having their respective unique promoter was investigated. The expression pattern of the IVa2 gene differed with the cell line used as for the L1 gene. Thus, in HepG2 cells, all of the four adenovirus vector-infected cells expressed the IVa2 gene at almost the same level, and no induction of the expression was noted by the CAG promoter. In contrast, the A549 cells, the expression of IVa2 cells, and the induction of expression by the CAG promoter was promoted.

On the other hand, the same result was obtained for the expression of the protein IX gene by both cell lines, and the protein IX gene was expressed to an almost same degree in the ΔE2A-CAHGH-, Ax1CAHGH- and AxCAwt-infected cells but very little in the Axlwl-infected cells. Thus, for the protein IX gene, the induction of expression by the CAG promoter was evidently observed.

From the foregoing results, it was demonstrated that the adenovirus gene of which expression is evidently induced by the CAG promoter is mainly the protein IX gene. This strongly indicated that the expression of the protein IX gene represents a cause of inflammation when a first generation adenovirus vector is administered in vivo.

Furthermore, from the above results, it was also demonstrated the expression of the protein IVa2 gene and the L1 gene was induced by the CAG promoter in some cells. Since the protein IVa2 gene has an independent promoter, it can be easily expected to be directly activated by the CAG promoter. However, the L1 gene is one of the major late genes, and is regulated by an MLP common to other late genes such as the L3 gene and the L5 gene, it cannot be expected that only the expression of the L1 gene is induced by the CAG promoter. However, since it is known that the L2 to L5 genes are expressed only at the later stages of infection, whereas the L1 gene is known to be also expressed in the early stages of infection (Shaw A. R. et al., Cell 22: 905-916 (1980)), the reason why the expression of the L1 gene is only induced by the CAG promoter is likely to be based on the difference in the mechanism of gene expression in the early and later stages. Furthermore, since it has been reported that both of the protein IX and the protein IVa2 have an effect of activating MLP (Lutz P. et al., J. Virol. 71: 5102-5109 (197), Tribouley C. et al., J. Virol. 68: 4450-4457 (1994)), it is likely that MLP has been indirectly activated via protein IX or protein IVa2 rather than the CAG promoter directly activates MLP. The degree of expression of these protein IVa2 gene and the L1 gene by the CAG promoter is weak when compared to the induction of expression of the protein IX gene, but it is likely that they induce inflammation by additively acting with protein IX.

Next, it was investigated which component of the CAG promoter induces the expression of adenovirus genes including the protein IX gene. The CAG promoter is composed of the IE enhancer of CMV, chicken β-actin promoter, the splice acceptor and poly(A) sequence of rabbit β-globin. In the adenovirus vector used in the present invention, the CAG promoter is inserted into the deletion site of E1 gene (1.3-9.2 m.u.) in the orientation toward left side (the reverse direction of that of transcription of E1), and the direction of the CAG promoter inserted is opposite to the direction of the protein IX gene (9.7-11.2 m.u.) that is transcribed rightward. Thus, it was considered to be likely that what induces the expression of the protein IX gene is not the β-actin promoter but is the IE enhancer of CMV. Thus, using an adenovirus vector (AdCMVlacZ) into which has inserted a CMV promoter containing the IE enhancer portion that is only common component to the CAG promoter, the expression of the protein IX gene was investigated. As a result, in the AdCMVlacZ-infected A549 cells, the protein IX gene was expressed at a level almost similar to that of the AxCAwt-infected cells in which the CAG promoter was only inserted. Therefore, it was confirmed that the CMV IE enhancer (CMV enhancer) induces the expression of the adenovirus gene including the protein IX gene.

In order to further confirm this result, using an adenovirus vector (AxEFlacZ-L) having inserted therein the EF-1α promoter which is a promoter containing no CMV-enhancer, the expression of the protein IX was investigated, and it was found that no protein IX gene was expressed at all in the AxEFlacZ-L-infected cells. Furthermore, using an adenovirus vector (AxCAlacZ-L) that has inserted therein the CAG promoter and the lacZ gene as the positive control, the degrees of inflammation caused by AdCMVlacZ and AxEFlacZ-L were compared by measuring serum GPT levels in mice that received the intravenous administration of adenovirus vectors. As a result, it was confirmed that serum GPT levels in the AdCMVlacZ-treated mice increased to levels equal to or higher than that of AxCAlacZ-L-treated mice, whereas in the AxEFlacZ-L-treated mice serum levels GPT increase very little. Thus, EF-1α promoter containing no CMV enhancer does not induce the expression of protein IX, and it was indicated that no inflammation occurs in adenovirus vectors that do not induce the expression of protein IX.

The above series of results taken together, a very important new mechanism that was not conventionally known was found by the present inventors that inflammation caused by the first generation adenovirus vectors is due to the induction of expression of the adenovirus gene by the CMV enhancer.

Promoters containing a CMV enhancer such as a CMV promoter, have been used for a variety of adenovirus vectors that are currently under clinical studies due to their high promoter activity. Examples thereof include: vectors that use the CMV promoter per se: tumor suppressor gene, p53-expressing adenovirus vector (Clayman G. L. et al., J. Clin. Oncol. 16: 2221-2232 (1998), and Swisher S. G. la, J. Natl. Cancer Inst. 91: 763-771 (1999)), an interleukin-2-expressing adenovirus vector (Stewart A. K. et al., Gene Ther. 6: 350-363 (1999)), a vascular endothelium growth factor VEGF121-expressing adenovirus vector (Rosengart T. K. et al., Circulation 100: 468-474 (1999)); examples of adenovirus vectors that use a hybrid promoter containing the CMV IE enhancer include cystic fibrosis transmembrane conductance regulatory protein (CFTR)-expressing adenovirus vector (Knowles M. R. et al., N. Eng. J. Med. 333: 823-831 (1995), and Zuckerman J. B. et al., Hum. Gene Ther. 10: 2973-2985 (1999)).

Thus, the discovery by the present inventors that a foreign promoter induces the expression of adenovirus gene leading to inflammation is not a phenomenon merely restricted to recombinant adenovirus vectors having a CAG promoter but a universal phenomenon applicable to many other adenovirus vectors that are currently under clinical studies. Therefore, based on such a finding, adenovirus vectors that have been modified so as not to induce the expression of adenovirus genes are expected to alleviate inflammation after administration and thereby to have the persistent expression of therapeutic genes, and are of high practical value.

Furthermore, the discovery of the present invention that a foreign promoter induces the expression of an adenovirus gene is likely to be applicable to adenovirus vectors having not only the CMV IE enhancer but other virus promoters. Examples of such promoters include the RSV promoter, a promoter containing the SV40 early gene enhancer, or the SRα promoter and the like.

Then, with a protein IX-relocated adenovirus vector and a protein IX-deleted adenovirus vector as an example, the method of carrying out the present invention is specifically described.

First, the method of constructing a protein IX-relocated adenovirus vector is described. The nucleotide sequence and the position of the protein IX gene are described in a reference (Maat J. et al., Gene 10: 27-38 (1980)). The method of preparing the relocated protein IX gene is not specifically limited, and may be excised by restriction enzyme digestion from a plasmid or cosmid (Miyake S. et al., Proc. Natl. Acad. Sci. USA 93: 1320-1324 (1996)) containing protein IX gene, but from the subsequent convenience of construction, the PCR method is preferably used for amplification. The range of the protein IX gene to be amplified preferably contains not only the coding sequence but the 5'-untranslated region and 3'-untranslated region of the protein IX gene. The 5'-untranslated region preferably contains the promoter region of the protein IX gene, and as an example thereof contains a sequence at positions 3525 and after of adenovirus type 5, and more preferably a sequence at positions 3213 and after. The range of the 3'-untranslated region is not specifically limited as long as it contains the base sequence to the termination codon of the protein IX gene, and may add a poly(A) sequence of another gene to immediately after the termination codon, or the original poly(A) sequence of the protein IX gene may be used. As an example of the latter, it preferably contains a polyadenylation signal and a base sequence up to position 4070 containing the site to which poly(A) is actually added, and more preferably a base sequence up to position 4076. The nucleotide sequence of PCR primers is not specifically limited as long as it is a sequence capable of amplifying the protein IX gene in the range mentioned above, but preferably it contains a recognition sequence of a suitable restriction enzyme in order to facilitate cloning of a DNA fragment containing the protein IX gene after amplification into a plasmid.

The DNA fragment containing a PCR-amplified protein IX gene may be directly inserted into the desired site of the adenovirus genome, but in order to confirm the absence of mutation in the nucleotide sequence during the PCR reaction, the amplified fragment is cloned first into a suitable plasmid etc., and then the nucleotide sequence is preferably confirmed to be ready for use. Plasmids for which the amplified fragment is cloned is not specifically limited, and as an example there can be mentioned pUC19 etc.

As sites into which a protein IX gene is relocated, as mentioned above, there can be mentioned a site between the L3 gene and the E2A gene, the deletion site of the E3 gene, etc., but as a more preferred example, a method of relocating between the upstream region of the E4 gene and the 3'-end ITR is described below. As a procedure for constructing an adenovirus vector in which the protein IX gene has been relocated to the above site, it is possible to transform a cell line such as 293 cells with a plasmid or a cosmid vector containing an adenovirus genome having a structure in which the protein IX gene has been deleted from the original position (9.7-11.2 m.u.) has been inserted between the upstream region of the E4 gene and the 3'-end ITR so as to obtain the desired recombinant adenovirus vector in one step. However, as an alternative method, a two-step procedure is also possible in which a recombinant adenovirus in which protein IX is retained at the original position and also having inserted therein a protein IX gene between the upstream region of the E4 gene and the 3'-end ITR is first constructed, and then the protein IX gene at the original position is deleted to construct an adenovirus vector in which the protein IX gene has been relocated. Though many steps are included in the latter method, it permits to certainly obtain the recombinant adenovirus vector of interest, and thus is a preferred method, which method of construction comprising two steps is described in detail below. The method of constructing a recombinant adenovirus vector described below is one in which 293 cells are transformed with a cosmid vector containing the majority of the adenovirus genome and DNA obtained by restriction digestion of the terminal protein-adenovirus DNA complex (DNA-TPC), and then a recombinant adenovirus vector of interest can be obtained by homologous recombination between the cosmid vector and the adenovirus DNA-TPC, and the principle and procedure thereof have been disclosed in an existing reference (Miyake S. et al., Proc. Natl. Acad. Sci. USA 93: 1320-1324 (1996)) and a patent (Japanese Unexamined Patent Publication (Kokai) No. 7-298877).

The cosmid vector pAx4w is a vector that contains 2.6-98.0 m.u. (the E3 gene is deleted) of the genome of adenovirus type 5 and 98.0-100 m.u. of the genome of adenovirus type 2, and has a restriction enzyme SwaI site as a cloning site, between the upper region of the promoter of the E4 gene and 3'-end ITR (99.3 m.u.) (Miyake S. et al., Proc. Natl. Acad. Sci. USA 93: 1320-1324 (1996), in said reference pAx4w has been described as pAdex4w). To the SwaI site of pAx4w, a protein IX gene prepared by the above-mentioned PCR method is inserted to obtain a cosmid vector pAx4pIX. On the other hand, a recombinant adenovirus vector Adex4SRlacZL is a replication-defective adenovirus vector which is derived from adenovirus type 5 (E1A, E1B, E3 genes are deleted), and which has inserted therein an expression unit of the *E. coli* lacZ gene at the same position of 99.3 m.u. as pAx4w. 293 cells are transformed with DNA-TPC which is obtained from adenovirus genomic DNAs prepared from this Adex4SRlacZL, by digestion with restriction enzyme AseI and EcoRI which digest several times at the right half of the genome, and with a cosmid vector pAx4pIX, then a recombinant adenovirus vector Ax4pIX in which the expression unit of the *E. coli* lacZ gene of Adex4SRlacZL has been replaced with the protein IX gene, can be generated. Ax4pIX is a recombinant adenovirus vector having a protein IX gene at two sites: the original position of protein IX gene and between the upstream region of the E4 gene and 3'-end ITR.

Then, the range of the nucleotide sequence to be deleted at the original position of the protein IX gene is explained. The protein IX gene is transcribed rightward, whereas the 3'-untranslated region of the protein IX gene partly overlaps with the 3'-untranslated region of the IVa2 gene and the E2B gene that are transcribed leftward, and therefore the deletion range of the protein IX gene must be the range that does not affect the functions of the IVa2 gene and the E2B gene. The polyadenylation site of the IVa2 gene and the E2B gene is thought to be the base at position 4060 for the example of adenovirus type 5, the deletion range must be to further left thereof. The deletion range is not limited as long as this condition is met and protein IX is not expressed, and as an example there can be mentioned the deletion from a PvuII site (Ad5: 452-457) to a AlwNI site (Ad5: 4048-4056) of adenovirus type 5. A vector containing an adenovirus genome deleted said range of bases can be easily constructed from the cosmid vector pAxcw (Japanese Unexamined Patent Publication (Kokai) No. 8-308585, page 15, pAdexlcw is identical with pAxcw). pAxcw is a cosmid vector that contains the majority of the adenovirus type 5 genome in which the E1 gene is deleted (A454-3328), and by the construction comprising several steps from pAxcw as the starting material, a cosmid vector pAxΔpIXcw can be obtained that contains an adenovirus genome having a deletion from the PvuII site to the AlwNI site. pAxΔpIXcw is a vector in which the E1A, E1B, and protein IX genes are deleted (Δ454-4053), and into the deletion site a cloning site (ClaI and SwaI sites) for a foreign gene has been inserted.

By transforming the 293 cells with DNA-TPC obtained by digesting genomic DNA prepared from the above-mentioned adenovirus Ax4pIX with a restriction enzyme EcoT22I having a plurality of recognition sites on the left of the genome and with the above-mentioned cosmid vector pAxΔpIXcw, a recombinant adenovirus vector AxRpIXcw of interest in which a protein IX gene has been relocated can be obtained. Though foreign genes such as a promoter have not been inserted into this AxRpIXcw, a protein IX-relocated adenovirus vector in which any foreign gene has been inserted can be readily obtained by homologous recombination of DNA-TPC obtained by digesting the genomic DNA of AxRpIXcw with EcoT22I and a cosmid vector in which a foreign gene has been inserted into the SwaI site or the ClaI site of a cosmid vector pAxΔpIXcw. Alternatively, a protein IX-relocated adenovirus vector in which any foreign gene has been inserted can also be obtained by homologous recombination of DNA-TPC obtained by digesting the genomic DNA of Ax4pIX with EcoT22I and a cosmid vector in which a foreign gene has been inserted into the SwaI site or the ClaI site of a cosmid vector pAxΔpIXcw.

As described above, a method of constructing a protein IX-relocated adenovirus vector was explained taking adenovirus type 5 as an example. The relocated protein IX gene need not use a gene derived from the same serotype adenovirus, and a protein IX gene of another serotype can be used as long as the protein functions sufficiently in the replication cycle of said adenovirus. By way of example, there may be mentioned a vector in which a type 2 protein IX gene has been relocated to the basic backbone of type 5, or conversely a vector in which a type 5 protein IX gene has been relocated to the basic backbone of type 2.

Then a method of constructing a protein IX-deleted adenovirus vector is explained. In order to construct said vector, a protein IX-expressing cell line is required, and therefore a method of constructing said protein IX-expressing cell line is explained. The range of protein IX gene to be introduced into the cell is not specifically limited as long as it contains the coding region of protein IX. A DNA fragment containing the coding region of protein IX can be excised from a plasmid etc. containing said gene by restriction enzyme digestion, or may be prepared by the PCR method. Promoters for expressing protein IX are not specifically limited, and a promoter that constitutively functions in the animal cell may be used, or an inducible promoter may be used. Alternatively, the original promoter for the protein IX gene may be used. A cell line that expresses protein IX can be obtained by transformation any cell with a plasmid containing the expression unit of the protein IX gene. However, cells used for the construction of said cell line are preferably cells expressing the adenovirus E1 gene, said cells being capable of producing efficiently a first generation adenovirus vector in which the E1 gene is deleted. Examples of such cells include 293 cells. Furthermore, in order to prevent the generation of a replication competent adenovirus (RCA) by homologous recombination between the vector genome and the genome in the cell, a cell line that has introduced therein only the minimum region required for the E1 gene is preferably used to construct a protein IX-expressing cell line. Furthermore, the desired cell line can also be obtained by first constructing a protein IX-expressing cell line from cells that are not expressing the E1 gene and then by transformation said cell line with the E1 gene. The method for transformation of cells and the selection of the cell line of interest are not specifically limited, and any cell lines that can supply an adequate amount of protein IX to a protein IX-deleted adenovirus vector may be used.

Next, a method of constructing a protein IX-deleted adenovirus vector is explained more specifically. The range of deleting the protein IX gene, as described for the protein IX-relocated adenovirus vector, may be any range that does not affect the function of the IVa2 gene and the E2B gene and does not permit the expression of protein IX, examples of which include the above-mentioned deletion of from the PvuII site (Ad5: 452-457) to the AlwNI site (Ad5: 4048-4056). The above-mentioned cosmid vector pAxΔpIXcw is a vector corresponding to the deletion of an adenovirus genome in said range. By transforming the above-mentioned protein IX-expressing cell line with this pAxΔpIXcw and DNA-TPC obtained by digesting genomic DNA of a first generation adenovirus vector, such as AxCAwt or Axlwl, with a restriction enzyme such as EcoT22I, the protein IX-deleted adenovirus vector of interest can be obtained. Foreign genes such as a promoter have not been inserted into the protein IX-deleted adenovirus vector AxΔpIXcw thus constructed. However, similarly to the case of the protein IX-relocated adenovirus vector, a protein IX-deleted adenovirus vector in which any foreign gene has been inserted can be readily obtained by homologous recombination of a cosmid vector in which a foreign gene has been inserted into the SwaI site or the ClaI site of a cosmid vector pAxΔpIXcw and DNA-TPC obtained by digesting the genomic DNA of AxΔpIXcw with EcoT22I etc. Alternatively, a protein IX-deleted adenovirus vector in which any foreign gene has been inserted can also be obtained by homologous recombination of DNA-TPC obtained by digesting the genomic DNA of any first generation adenovirus vector such as AxCAwt and Axlwl with EcoT22I and a cosmid vector in which a foreign gene has been inserted into the SwaI site or the ClaI site of a cosmid vector pAxΔpIXcw.

As described above, the method of constructing a protein IX-relocated adenovirus vector and a protein IX-deleted adenovirus vector was explained taking adenovirus type 5 as an example. However, the present invention is not limited to adenovirus type 5, and can be applied to any adenovirus vector having the adenovirus backbone of other serotype including adenovirus type 2.

Then a pharmaceutical composition comprising as an active ingredient the recombinant adenovirus vector of the present invention, and a method of gene therapy in which inflammation has been alleviated will be explained. The recombinant adenovirus vector of the present invention obtained as above is a highly safe vector in which inflammation has been alleviated when administered to humans, and can be used in gene therapy for various diseases as an active ingredient of a pharmaceutical composition. When the recombinant adenovirus vector of the present invention is used as a pharmaceutical composition, either an in vivo or an ex vivo method can be selected, as appropriate, depending on the disease to be treated, the target organ, and the like. As used herein, the in vivo method is a method in which a pharmaceutical composition for gene therapy is directly introduced into the body of a patient, and an ex vivo method is a method in which certain cells are removed from the patient and the above pharmaceutical composition is introduced ex vivo into said cells, and then the cells are returned to the patient's body.

In the recombinant adenovirus vector of the present invention, the in vivo administration route is not specifically limited, and may be administered intravenously, arterially, subcutaneously, dermally, or intramuscularly to the subject organ such as liver, lung, kidney, brain and the like. Dosage forms used for the in vivo administration are not specifically limited either, and when, for example, used an injection, said injection can be prepared by a standard method. Thus, after the recombinant adenovirus vector of the present invention was dissolved aseptically in a suitable solvent (a buffer such as PBS, physiological saline, sterilized water, etc.), it may be filled into a sterile vessel for preparation. A conventionally used carrier may be added to said pharmaceutical formulation as required.

When the adenovirus vector of the present invention is applied in an ex vivo method, the cell used is not specifically limited, and any cells that serve the intended use such as leukocytes such as lymphocytes, various tumor cells derived from patients, etc. may be used.

The dosage of said pharmaceutical composition of the present invention to patients may be prepared as appropriate depending on the disease to be treated, the age and body weight of the patient, and the like. Usually about $10^6$-$10^{14}$ (PFU), preferably about $10^8$-$10^{12}$ (PFU) of the recombinant adenovirus vector of the present invention may be administered per dose, or continuously for several days, or about once a month.

As adenovirus vectors that are currently under clinical studies, as described above, there are known a tumor suppressor gene p53 expression vector, an interleukin 2 expression vector, a vascular endothelial growth factor (VEGF) 121 expression vector, a cystic fibrosis transmembrane conductance regulatory protein (CFTR) expression vector, and the like. The recombinant adenovirus vector of the present invention can be used in stead of conventional adenovirus vectors as a vector in which inflammation resulting from the use of a conventional adenovirus vector has been alleviated.

For example, a protocol etc. of a clinical study using the tumor suppressor gene p53 expression vector has been described in a reference (Roth J. A. et al., Hum. Gene Ther. 7: 1013-1030 (1996)), and thus it is possible to perform the gene therapy of the present invention according to said protocol.

The recombinant adenovirus vector of the present invention may be used not only as a drug for gene therapy of humans but as a vector for gene transfer to animals. The method may be carried out according to the above-mentioned method of gene therapy for humans such as the in vivo and the ex vivo methods.

Also, reference can be made to many already known publications and examples described below. The characteristics of the adenovirus vector of the present invention of being a vector in which inflammation has been alleviated has a major advantage over conventional adenovirus vectors even when used on animals, since there is no need to concern adverse effect derived from vectors such as inflammation in a variety of purposes such as the creation of animal models of disease, therapeutic models of human diseases, the functional analysis of a gene, and the like.

The present invention will now be explained in further details hereinbelow with reference to examples, however it should be noted that the present invention is not limited by these examples in any way, and that commonly used alterations in the art of the present invention may be made. Procedures dealing with phages, plasmids, DNA, various enzymes, *E. coli*, cultured cells etc. in the examples were carried out, unless otherwise specified, according to the methods described in "Molecular Cloning, A Laboratory Manual, T. Maniatis et al. ed., Seconds edition (1989), Cold Spring Harbor Laboratory."

Cosmid vectors pAxCAwt (Kanegae Y. et al., Nucleic Acids Res. 23: 3816-3821 (1995), and pAxcw (Japanese Unexamined Patent Publication (Kokai) No. 8-30858858, page 15, pAdexlcw is identical with pAxcw) used in the examples of the present invention are vectors that contain the majority of the adenovirus type 5 genome other than adenovirus E1 and E3 genes. Furthermore, pAxCAwt has introduced thereinto a CAG promoter (Niwa H. et al., Gene 108: 193-200 (1991), and Japanese Patent No. 2824434) at the E1 gene deletion site, and has a cloning site between the promoter and the poly(A) sequence. pAxcw has only inserted therein a ClaI site and a SwaI site at the E1 gene deletion site. The method of transformation of the 293 cells (ATCC CRL-1573) with these cosmid vectors and adenovirus DNA-terminal protein complex and of constructing a recombinant adenovirus vector by homologous recombination (COS/TPC method) was carried out according to an existing reference (Miyake S. et al., Proc. Natl. Acad. Sci. USA 93: 1320-1324 (1996)) and a patent (Japanese Unexamined Patent Publication (Kokai) No. 7-298877). Furthermore, the purification method of an adenovirus vector by ultracentrifugation (Kanegae Y. et al., Jpn. J. Med. Sci. Biol. 47: 157-166 (1994)) and the determination method of virus titers by limiting dilution using the 293 cells (Japanese Unexamined Patent Publication (Kokai) No. 7-298877) were also carried out based on the existing methods, unless otherwise specified.

EXAMPLE 1

Construction of a Human Growth Hormone-expressing Adenovirus Vector (1) Cloning of Human Growth Hormone cDNA In order to clone human growth hormone cDNA by the PCR method, the following procedure was carried out.

Phage DNAs were prepared from a commercial human pituitary adenoma-derived cDNA library (CLONTECH), and used as a template DNA for PCR. Primers for PCR were designed so as to add a recognition site for a restriction enzyme on both ends, and the 5'-end primer contained the initiation codon and a NheI recognition site, and the 3'-end primer contained the termination codon and a SphI recognition site. The sequence of each primer is shown below:

```
5'-end primer
5-TGGCTAGCTCACCTAGCGGCAATGGCT-3'    (SEQ ID NO: 1)
    NheI                Met 3'-end primer
5-CAGGCATGCCACCCGGGCAGCTAGAA-3'     (SEQ ID NO: 2)
     SphI             End
```

Using the above-mentioned cDNA library-derived DNA as a template, polymerase pfu (Takara Shuzo) was used in a standard PCR reaction to thereby obtain an about 700 bp amplified fragment containing hGH cDNA. After the amplified fragment was blunt-ended with a Klenow enzyme, it was inserted into the HincII site of plasmid pUC19 to obtain a plasmid pUCHGH (3.4 kb). By sequencing of the cDNA portion of pUCHGH and the sequence was confirmed to be identical with the sequence described in a reference (Chen E. Y. et al., Genomics 4: 479-497 (1989)).

(2) Construction of a Human Growth Hormone-expressing Recombinant Adenovirus Vector After pUCHGH was digested with NheI and BglI, it was blunt-ended to obtain an about 0.7 kb DNA fragment containing the coding region of hGH cDNA. The cDNA fragment was inserted into the SwaI site between the promoter and the poly(A) sequence of a cosmid vector pAxCAwt to obtain a cosmid pAxlCAHGH.

In order to confirm that the expression unit of hGH has been precisely integrated into the cosmid pAxlCAHGH, a plasmid containing the expression unit of hGH was constructed from pAxlCAHGH, and the hGH protein was allowed to be transiently expressed in the COS7 cells (monkey kidney-derived cell line). Thus, pAxlCAHGH was self-ligated after digestion with NruI to obtain a hGH-expressing plasmid PxlCAHGH in which the majority of the adenovirus DNA has been removed (contains about 0.4 kb at the left end). Then, COS7 cells were transfected with the PxlCAHGH by the DEAE-dextran method, and two days later the hGH concentration in the conditioned medium was determined by the ELISA method (Picoia™ HGH plate: Sumitomo Pharmaceuticals). Though the hGH concentration in the condition medium of the COS7 cells in which the plasmid has not been introduced was below the detection limit, 1 ng/ml or more of hGH was detected in the conditioned medium of the COS7 cells transformed with PxlCAHGH. This result confirmed that the expression unit of hGH has been precisely integrated into the cosmid pAxlCAHGH.

Finally, by the above-mentioned COS/TPC method, 293 cells were transformed with the cosmid pAxlCAHGH and the adenovirus DNA-terminal protein complex to obtain a hGH-expressing recombinant adenovirus Ax1CAHGH (FIG. 1, the E1 gene and E3 gene are deleted).

EXAMPLE 2

Construction of an E2A Gene-deleted Adenovirus Vector Expressing hGH (1) Construction of a Recombinant Adenovirus Vector for Constructing an E2A-deleted Adenovirus Vector The cosmid vector pAx2LD3LCAwt (pAdex2LD3LCAwt in Japanese Unexamined Patent Publication (Kokai) No. 8-308585, on page 19, is identical with pAx2LD3LCAwt) is a derivative of the above-mentioned cosmid vector pAx-CAwt. pAx2LD3LCAwt is a cosmid in which loxP sites have been inserted between the adenovirus L3 gene and the E2A gene (61.5 map units), and in the deletion site (78.0 map units) of the E3 gene, and the nucleotide sequence other than the loxP insertion sites is identical with pAxCAwt.

After the plasmid pUCHGH constructed in Example 1 was digested with NheI and BglI, it was blunt-ended to obtain an about 0.7 kb DNA fragment containing the coding region of hGH cDNA. The DNA fragment was inserted into the SwaI site between the promoter and the poly(A) sequence of the cosmid vector pAx2LD3LCAwt to obtain a cosmid pAx2LD3LCAHGH.

An adenovirus vector Adex2LD3LCANLacZ (FIG. 1, Japanese Unexamined Patent Publication (Kokai) No. 8-308585, page 21) is a recombinant adenovirus in which two loxP sites have been inserted into the same position as the cosmid vector pAx2LD3LCAwt and which expresses *Escherichia coli* β-galactosidase.

In order to construct a recombinant adenovirus in which the inserted gene of Adex2LD3LCANLacZ has been replaced from lacZ to hGH, the following procedure was carried out according to an existing method (Japanese Unexamined Patent Publication (Kokai) No. 7-298877). First, an adenovirus DNA-terminal protein complex was prepared from Adex2LD3LCANLacZ, and then digested with EcoT22I. 293 cells were transfected with this DNA-terminal protein complex and the cosmid pAx2LD3LCAHGH to obtain a recombinant adenovirus Ax2LD3LCAHGH (FIG. 1) having the hGH expression unit and two loxP sites. This Ax2LD3LCAHGH is identical with the adenovirus vector Ax1CAHGH constructed in Example 1 in the structure other than the loxP-inserted portion, and is identical with the adenovirus vector Adex2LD3LCANLacZ in the structure other than the expression unit.

(2) Construction of an E2A-deleted Adenovirus Vector

In order to construct a recombinant adenovirus (E2A-deleted adenovirus vector) in which the E2A gene and the L4 gene flanked by two loxP sites have been deleted from the adenovirus vector Ax2LD3LCAHGH by the action of recombinase Cre, the following procedure was carried out.

First, the adenovirus vector Ax2LD3LCAHGH and the recombinase Cre-expressing adenovirus vector AxCANCre (FIG. 1, Kanegae Y. et al., Nucleic Acids Res. 23: 3816-3821 (1995)) were purified by the ultracentrifugation method (supra), and the titer of each virus was determined by the limiting dilution method (supra) using 293 cells.

Then to almost confluent 293 cells in a collagen-coated 225 $cm^2$ culture flask, 4 ml of the culture medium (Dulbecco's Modified Eagle's Medium containing 5% FCS: DMEM) containing $3.0 \times 10^7$ PFU/ml of Ax2LD3LCAHGH (moi 2) and $1.5 \times 10^7$ PFU/ml of AxCANCre (moi 1) was added to infect both viruses at 37° C. for 1 hour. After infection, 21 ml of DMEM medium containing 5% FCS was added, and cultured at 37° C. in the presence of 5% $CO_2$. Two days later, cells attached to the bottom of the flask were scraped with a cell scraper, and the cell suspension containing the conditioned medium was placed into a 50 ml centrifuge tube, which was centrifuged at 2500 rpm (1130×g) at 4° C., for 5 minutes, and after discarding the supernatant the cell fraction was stored frozen at −80° C.

(3) Purification of an E2A-deleted Adenovirus Vector

Though a hGH-expressing E2A-deleted adenovirus vector (ΔE2A-CAHGH: 28.1 kb) of interest has been generated in the 293 cells co-infected with the above Ax2LD3LCAHGH and AxCANCre, there are also Ax2LD3LCAHGH (34.4 kb) and AxCANCre (34.7 kb) present, and hence these three viruses are present in a mixture (figures in parentheses indicate genome size of each virus). Thus, in order to isolate ΔE2A-CAHGH based on the difference of specific gravity of virus, the following cesium chloride (CsCl) density gradient ultracentrifugation was carried out to purify the E2A-deleted adenovirus vector. The CsCl solutions used for purification were all prepared in a 50 mM Hepes buffer (pH 7.4), and centrifugation and ultracentrifugation were carried out at 4° C.

1) The cell fraction of 293 cells containing (ΔE2A-CAHGH that had been stored frozen at −80° C. was thawed, and was suspended into 25 ml of 50 mM Hepes buffer (pH 7.4) per the cells from eight 225 $cm^2$ flasks. Then the cell suspension was placed in a 200 ml sonication cup, and was sonicated (200 W, 3 minutes (30 seconds×6 times), 4° C.) in a closed type sonicator (manufactured by Cosmo Bio, model UCD-200T). The cell homogenate was transferred to a 30 ml centrifuge tube, which was centrifuged at 10,000 rpm (11,850×g) for 10 minutes. The supernatant after centrifugation was subjected to a three-step ultracentrifugation.

2) In order to concentrate the adenovirus in the cell homogenate, 8 ml of CsCl solution with a specific gravity of 1.43 was placed in an ultracentrifuge tube for the Beckmann swing rotor SW28, and about 25 ml of the supernatant prepared in the above 1) was layered thereupon, and was ultracentrifuged at 23,000 rpm (95,400×g) for about 1.5 hour. After centrifugation, a band containing adenovirus around the interface of the aqueous phase and the CsCl phase was recovered (about 2.5 ml per tube), and a saturated CsCl solution at an amount equal to the recovered virus solution was added.

3) To an ultracentrifuge tube for the Beckmann swing rotor SW41, the following solutions were layered sequentially from the bottom. The virus solution (about 5 ml) prepared in the above 2)/a CsCl solution (4.5 ml) with a specific gravity of 1.32/a CsCl solution (2.5 ml) with a specific gravity of 1.25. This was ultracentrifuged at 35,000 rpm (210,000×g) for 3 hours. Since, by this ultracentrifugation, protein formes a broad band around the interface of the CsCl solution with a specific gravity of 1.25 and 1.32, and virus formes a sharp band around the middle of the CsCl solution with a specific gravity of 1.32, the band of virus was recovered (about 1.5 ml per tube), and the CsCl solution with a specific gravity of 1.36 at an amount equal to the recovered virus solution was added therein.

4) To an ultracentrifuge tube for SW41, about 2 ml of the virus solution prepared in 3) and 10 ml of the CsCl solution with a specific gravity of 1.34 were added, mixed well, and ultracentrifuged at 30,000 rpm (154,000×g) for about 19 hours. By this ultracentrifugation, the bands of viruses are each separated depending on the specific gravity of each virus. Since Ax2LD3LCAHGH (34.4 kb) and AxCANCre (34.7 kb) have an almost equal genome size, the specific gravities thereof are almost equal, and virus bands after ultracentrifugation overlapped, whereas ΔE2A-CAHGH (28.1 kb) has a smaller specific gravity than these viruses, a band was formed in the upper part of the tube by ultracentrifugation. A hole was made on the side of the ultracentrifuge tube by a syringe needle to recover the band of ΔE2A-CAHGH.

5) Finally, in order to remove CsCl from the virus solution, recovered virus solution was dialyzed against PBS(−) containing 10% glycerol to obtain a finally purified product of ΔE2A-CAHGH. The virus after dialysis was stored frozen at −80° C. after aliquoting.

(4) Determination of Infectious Titer and Purity of an E2A-deleted Adenovirus Vector 1) Determination of Infectious Titer Since the E2A-deleted adenovirus does not replicate in the 293 cells, its titer cannot be determined by the standard method using the replication in the 293 cells as an index unlike the first generation adenovirus vectors (the E1 gene is deleted). Thus, with the amount of products of a reporter gene, hGH, as an index, the amount of produced hGH by a hGH-expressing first generation adenovirus vector Ax1CAHGH of which titer is known and that of ΔE2A-CAHGH were compared to determine the relative titer (infectious titer) of ΔE2A-CAHGH.

The adenovirus vector to be tested was serially diluted in a DMEM medium containing 2% FCS, 50 µl of which was then added to the A549 cells (human lung tumor-derived cell line) that had been cultured in a 96-well microtiter plate to infect at 37° C. for 1 hour. Then the virus solution was removed, the cells were washed once with the medium, 100 µl of the 2% FCS-containing DMEM medium was added thereto, and cultured for two days. After completion of the culture, the amount of hGH in the conditioned medium was determined by the ELISA method (Picoia™ HGH plate: Sumitomo Pharmaceuticals).

First, a preliminary examination was carried out using a first generation adenovirus vector Ax1CAHGH and it was found that the amount of virus added and the amount of hGH produced correlated in the range of moi 0.01-1 during virus infection, confirming that the amount of hGH produced reflects the amount of added virus.

Thus, using Ax1CAHGH (Lot B, titer $3.0 \times 10^{10}$ PFU/ml) of which titer is known as the control virus, the infectious titer of ΔE2A-CAHGH (Lot 3) was determined. The dilution ratio for each virus during infection were 30,000, 90,000, and 270,000 fold, and the amount of hGH produced two days later was compared. In any dilution ratio, the amount of hGH produced was higher in Ax1CAHGH (Lot B) than in ΔE2A-CAHGH (Lot 3) with the mean being about 1.1 fold. Accordingly, the titer of ΔE2A-CAHGH (Lot 3) was calculated to be $3.0 \times 10^{10}$ PFU/ml×1/1.1=$2.7 \times 10^{10}$ PFU/ml (equivalent).

By calculating the total yield of ΔE2A-CAHGH (Lot 3) based on this value, the 293 cells from forty eight 225 cm² flasks yielded $4.7 \times 10^{10}$ PFU (equivalent) of virus. Furthermore, from absorbance determination of purified virus at 260 nm, the ratio of particles to plaque forming units (PFU) of ΔE2A-CAHGH was 63.

A similar determinations were made for another lot of ΔE2A-CAHGH and it was found that the total yield of ΔE2A-CAHGH (Lot 2) per the 293 cells from twenty 225 cm² flasks was $1.9 \times 10^{10}$ PFU (equivalent) of virus, and the ratio of particles to plaque forming units (PFU) was 47.

2) Determination of Purity

Though the E2A-deleted adenovirus vector is purified by ultracentrifugation, there are slight contaminations of the first generation adenovirus vectors (Ax2LD3LCAHGH and AxCANCre) that could not be removed during purification. Since these contaminating first generation adenovirus vectors can replicate in the 293 cells, the titer determined by the standard method (limiting dilution) using the 293 cells reflects the amount of the contaminating first generation adenovirus vectors. Accordingly, in order to determine the purity of ΔE2A-CAHGH (Lot 3), the titer was determined by the limiting dilution method using the 293 cells. The titer of ΔE2A-CAHGH (Lot 3) was $7.8 \times 10^8$ PFU/ml, that of Ax1CAHGH (Lot B) was $4.4 \times 10^{10}$ PFU/ml, and the ratio was 1.8%. Since the infections titer of Ax1CAHGH (Lot B) was 1.1 fold that of ΔE2A-CAHGH (Lot 3) from the result of 1), this value was corrected and the purity of ΔE2A-CAHGH (Lot 3) was calculated to be (1−0.018×1.1)×100≅98%.

Also, from a similar determination, the purity of ΔE2A-CAHGH of another lot (Lot 2) was 97%.

(5) Confirmation of Decreased Expression of Adenovirus Protein of the E2A-deleted Adenovirus Vector For the cells infected with the E2A-deleted adenovirus vector, the fluorescent antibody method was used to determine whether the expression of DBP (single stranded DNA binding protein) encoded by the E2A gene and hexon, a major structural protein of adenovirus particles, was decreased.

To confluent A549 cells cultured in a collagen-coated 8-well culture slide (Becton Dickinson, #40630), 100 µl of the virus solution containing ΔE2A-CAHGH or Ax1CAHGH diluted in the 5% FCS-containing DMEM medium to a moi of 100 or 10 was added to infect at 37° C. for 1 hour. After infection, the virus solution was removed, 0.3 ml of DMEM medium containing 5% FCS was added, and cultured for two days. Two days later, the conditioned medium was removed and the cells were washed with PBS(−), 0.4 ml of 2% paraformaldehyde/PBS(−) was added, the cells were fixed at room temperature for 10 minutes, and washed twice with PBS(−). Furthermore, after the membrane permeability treatment (room temperature, 30 minutes) with 1 mg/ml of saponin, the cells were subjected to detection of DBP or hexon.

For detection of DBP, after blocking the slide glass with 10% normal goat serum, rabbit anti-DBP peptide (RPPT-MEDVSSPSPSPPPPRAPPKKR: (SEQ ID NO: 25) corresponding to the amino acid residues at positions 22-46 of DBP) antibody and FITC-labeled goat anti-rabbit antibody (JACKSON, #111-096-003) were sequentially reacted, subjected to nuclear staining with the DAPI (4', 6-diamino-2-phenyl-indole) solution, and examined under an epi-illumination fluorescence microscope (Olympus BX-50).

For detection of hexon, after blocking the slide glass with 10% normal rabbit serum, goat anti-hexon antibody (CHEMICON, AB-1056) and FITC-labeled rabbit anti-goat antibody (Vector Laboratories, FI5000) were sequentially reacted, subjected to nuclear staining with DAPI, and examined under an epi-illumination fluorescence microscope.

In the ΔE2A-CAHGH-infected cells, expression levels of both DBP and hexon were clearly decreased, and the ratio of DBP- and hexon-positive cells in the cells infected with ΔE2A-CAHGH at a moi of 100 was almost identical with that in the cells infected with Ax1CAHGH at a moi of 10. Therefore, it was confirmed as originally expected that the expression of the adenovirus gene is decreased in ΔE2A-CAHGH.

EXAMPLE 3

Investigation of Inflammation-inducing Effect of an E2A-deleted Adenovirus Vector In order to determine whether the deletion of the adenovirus E2A gene leads to reduction of the inflammation-inducing effect, the hGH-expressing E2A-deleted adenovirus vector (ΔE2A-CAHGH) or a hGH-expressing first generation adenovirus vector (Ax1CAHGH) were injected to mice, and the effect of inducing inflammation in both adenovirus vectors was compared with the serum GPT levels (glutamic pyruvic transaminase) as an index. The method and the result are shown below.

(1) Method

Mice used were C57BL/6 mice (7-week old, female). The adenovirus vector used was ΔE2A-CAHGH (Lot 3) or Ax1CAHGH (Lot C). The dosage of the adenovirus vector was $1\times10^9$ PFU, $3\times10^8$ PFU, or $1\times10^8$ PFU (five animals per group), and an adenovirus vector diluted in saline was administered via the tail vein at 0.2 ml per mouse. Three days before, and 3, 5, 7, 10, 14, 21, 28, 35, 42, 49, 56, and 63 days after the administration of the adenovirus vector, blood was partially collected from the orbital vein of the animals using a heparinized hematcrit tube under ether anesthesia. The blood was centrifuged at 10,000 rpm for 5 minutes to separate serum, which was stored at −20° C. until use. Serum levels of GPT were determined by the POP-TOOS method using the Transaminase CII-Test Wako (Wako Pure Chemicals).

(2) Result

Figure 2:
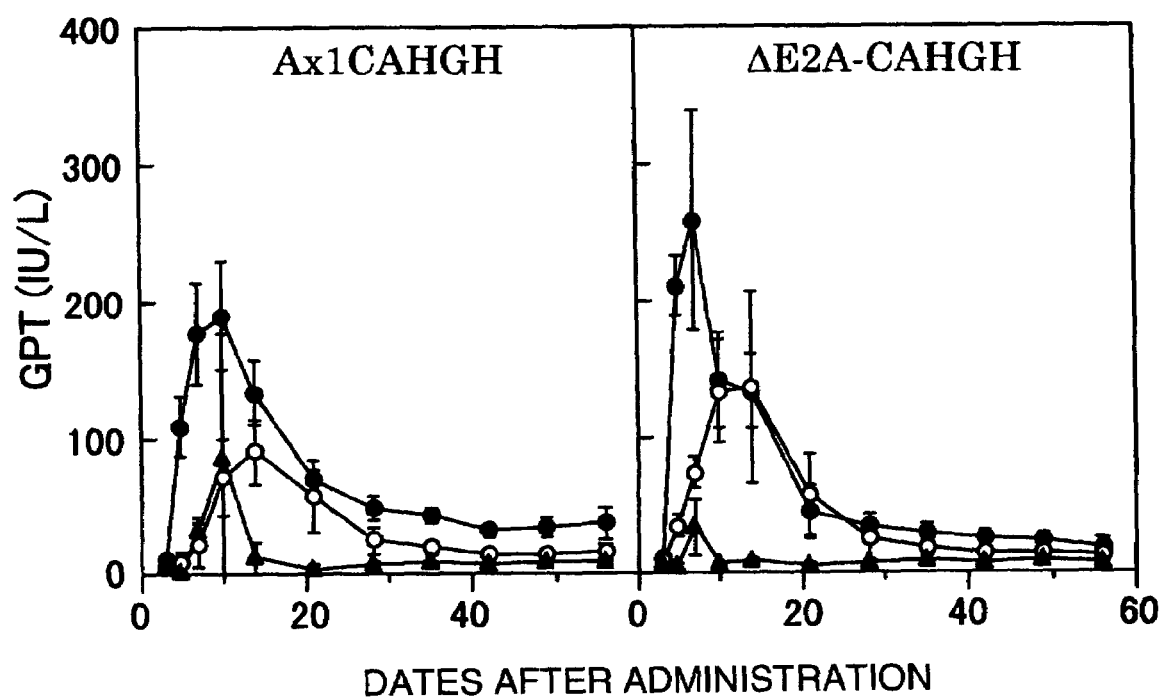
FIG. 2 is a graph showing mean values of daily changes in serum GPT levels of C57BL/6 mice which were injected with an adenovirus vector Ax1CAHGH or ΔE2A-CAHGH by tail vein (five mice per group). In the figure, ● is a group injected with $1 \times 10^9$ PFU, ○ is a group injected with $3 \times 10^8$ PFU, and ▲ is a group injected with $1 \times 10^8$ PFU of the adenovirus vector. The experiment was carried out on five mice per group. Serum hGH levels in one mouse was evidently lower (one tenth or lower, data not shown) than in the other four mice in each of the Ax1CAHGH $1 \times 10^9$ PFU administration group and the ΔE2A-CAHGH $3 \times 10^8$ PFU administration group. Therefore, in these two groups, the value of respective mouse was omitted at calculation of the mean values and the mean GPT values of four mice per group are shown.

Mean values of serum levels of GPT determined at constant intervals after administering the adenovirus vector to C57BL/6 mice are shown in FIG. 2. In order to confirm the administration efficiency of the vectors in each treated group, serum levels of hGH were also determined three days and five days after adenovirus vector administration. In the groups treated with the same dosage of adenovirus vectors, there was no significant difference in serum hGH levels between the Ax1CAHGH treated group and the ΔE2A-CAHGH treated group, confirming that both vectors were administered at the same efficiency.

Next, serum GPT levels were determined. In the ΔE2A-CAHGH-treated mice, serum GPT levels were increased with the increased dosage of adenovirus vector, and there was no difference from the mice treated with a first generation adenovirus vector. This result indicated that the deletion of the adenovirus E2A gene does not lead to alleviation of inflammation-inducing effect.

EXAMPLE 4

Preparation of UV-inactivated Adenovirus Particles

In order to clarify whether inflammation occurring at the administration of an adenovirus vector to mice is caused by the adenovirus vector per se, UV-inactivated adenovirus particles were prepared by the following procedure.

To 1.8 ml of the hGH-expressing adenovirus vector Ax1CAHGH ($3.0\times10^{10}$ PFU/ml, $1.4\times10^{12}$ particles/ml) purified by the method described in Example 2-(2), 18 μl of 33 mg/ml 8-methoxypsoralen (8-MOP) was added (the final concentration of 8-MOP is 330 μg/ml), and then 0.6 ml each thereof was aliquoted into three tissue culture petri dishes (Sumitomo Bakelite, Cat. No. MS-10350) with a diameter of 35 mm. Then the petri dishes were placed on ice, and were placed at 5 cm below a UV lamp of a UV crosslinker (Stratalinker™ UV Crosslinker 1800 model, STRATAGENE) equipped with UV lamps (8 watts, 5 lamps) having a wavelength of 365 nm while keeping the lid closed. UV was irradiated for 1 hour (UV intensity of about 1.8 kW) while changing the position of the dishes every 10 minutes. After UV irradiation, the virus solution was recovered from the dishes, and were dialyzed overnight against 10% glycerol-containing PBS(−) in order to remove 8-MOP. Finally, about 1.7 ml of the virus solution with a particle concentration of $1.1\times10^{12}$ particles/ml was recovered, which was stored frozen at −80° C.

That the adenovirus vector was inactivated by the above treatment was confirmed by two methods of determining the amount of produced hGH and of determining the titer. The determination of the amount of produced hGH was carried out in the method described in the above Example 2-(4), except that hGH concentration was determined one day after adenovirus vector infection. The amount of produced hGH in cells infected with $1\times10^5$ particles/ml of adenovirus vector Ax1CAHGH before UV-inactivation was about 0.2 ng/ml, and the amount of produced in cells infected with $1\times10^{10}$ particles/ml was about 28 μg/ml. On the other hand, for the above inactivated adenovirus vector, the amount of produced hGH was 0.4 ng/ml even when infected with $1\times10^{10}$ particles/ml. Thus, it was confirmed that the infectivity of adenovirus vector decreased to one in $10^5$ by inactivation from the calculation of the amount of produced hGH. Titer determination was also performed by a standard method using 293 cells. The virus titer before inactivation was about $3\times10^{10}$ PFU/ml, whereas the titer after inactivation was less than $2\times10^3$ PFU/ml, and thus the titer of virus decreased to one in $10^7$ or lower.

The above result confirmed that the viruses that received the UV-irradiation treatment (UV-inactivated adenovirus particles) of the present invention have been fully inactivated.

EXAMPLE 5

Investigation on the Cause of Inflammation after Administration of a First Generation Adenovirus Vector It was shown in Example 3 that even when the E2A-deleted adenovirus vector was administered to mice, serum GPT levels of treated mice were not decreased as compared to mice treated with first generation adenovirus vector (Ax1CAHGH). As an interpretation of this result, the following four possibilities were considered: 1) the expression of E2A gene is not associated with inflammation, 2) the hGH protein used as reporter serves as the antigen for cell-mediated immunity thereby causing inflammation, 3) a virus gene product of which expression was induced by a foreign promoter (CAG promoter) serves as the antigen for cell-mediated immunity, and 4) not the virus protein synthesized de novo in the infected animal but the virus particle-constitutive protein that was incorporated into the cell during virus infection serves as the antigen for cell-mediated immunity.

Thus, adenoviruses of different structures were administered to mice, and the cause of inflammation after the administration of the first generation adenovirus vector was investigated by measuring serum GPT levels as an index. The adenovirus vectors used, the experimental method and the result are shown below.

(1) Adenovirus Vectors
The adenovirus vectors used are shown below. All of them are first generation adenovirus vectors.
hGH-expressing adenovirus vector: Ax1CAHGH
An adenovirus vector in which a CAG promoter has been only inserted without hGH cDNA: AxCAwt (FIG. 1: a poly(A) sequence was also inserted) (Kanegae Y. et al., Nucleic Acids Res. 23: 3816-3821 (1995))
An adenovirus vector in which no foreign gene such as a promoter has been inserted (a restriction enzyme SwaI site has only been inserted): Axlwl (FIG. 1, Miyake S. et al., Proc. Natl. Acad. Sci. USA 93: 1320-1324 (1996), described in this reference as Adexlw)
An inactivated virus by UV irradiation on Ax1CAHGH: UV-inactivated particles (see Example 4).

(2) Method
The method is largely identical with that shown in Example 3. Different points are only described below.

The dosage of vectors was $1 \times 10^9$ PFU, $3 \times 10^8$ PFU, $1 \times 10^8$ PFU, or $3 \times 10^7$ PFU (five animals per group). Since the dosage of UV-inactivated adenovirus particles cannot be determined in terms of PFU, they were administered at the same amount in terms of the number of particles.

Blood was collected three days before, and 3, 5, 7, 10 (or 11), 14, 21, and 28 days after the administration.

(3) Result
The experiment was carried out in two divided runs. In the first run, Ax1CAHGH and AxCAwt were compared (FIG. 3, upper column). In the second run, Ax1CAHGH, Axlwl and UV-inactivated adenovirus particles were compared (FIG. 3, lower column). In both runs, a group was set up as a negative control in which saline used for the dilution of vectors was only administered. In FIG. 3, the data on the saline-treated group is only from the first run, but a similar result was obtained in the second run.

Between in the group treated with an adenovirus vector (Ax1CAHGH) that expresses hGH under the control of the CAG promoter and in the group treated with an adenovirus vector (AxCAwt) that only has the CAG promoter, there was very little difference in the degree of increases in serum GPT levels. It was demonstrated therefore that the expression of reporter gene, hGH, is not associated with inflammation. On the other hand, in the group treated with the adenovirus vector (Axlwl) in which no foreign gene has been inserted and in the group treated with UV-inactivated adenovirus particles, there was no increase in serum GPT levels. Since the difference in the structure between AxCAwt and Axlwl is only in the presence or absence of a CAG promoter and a poly(A) sequence, the cause of the increase in serum GPT levels, namely the cause of inflammation, was shown to be the CAG promoter.

EXAMPLE 6

Identification of an Adenovirus Gene of which Expression is Induced by the CAG Promoter In the first generation adenovirus vectors, in order to identify an adenovirus gene of which expression is induced by the CAG promoter thereby causing inflammation, various adenovirus vectors shown below were infected to cell lines (A549 cells or HepG2 cells) in which the first generation adenovirus vectors cannot replicate, and the adenovirus genes expressed were analyzed by Northern blotting. The adenovirus vectors used for this study were the first generation adenovirus vectors (Ax1CAHGH, AxCAwt) having a CAG promoter, a first generation adenovirus vector (Axlwl) in which there is no foreign promoter, and the E2A-deleted adenovirus vector (ΔE2A-CAHGH) having a CAG promoter. As used herein, the adenovirus gene of interest, namely the gene of which expression is induced by the CAG promoter, is an adenovirus gene that is expressed to the same degree in the cells infected with the three vectors (Ax1CAHGH, AxCAwt, ΔE2A-CAHGH), but is expressed very little in the Axlwl-infected cells. The method and the result are shown below.

(1) Method
Nearly confluent (about $5 \times 10^6$ cells) A549 cells (human lung tumor-derived cell line) or HepG2 cells (human hepatoma-derived cell line) in a 25 $cm^2$ culture flask, were infected 0.3 ml of each adenovirus vector diluted in a 5% FCS-containing DMEM medium for 1 hour (moi 100). After infection, the virus solution was removed and 5 ml of 5% FCS-containing DMEM medium was added and cells were cultured for 24 hours. Twenty four hours later, the conditioned medium was removed and the cells were washed twice with PBS(-), and then using ISOGEN (Nippongene), RNA was prepared from each virus-infected cell according to the instruction manual.

Probes used for Northern blotting were obtained by labeling the DNA which was amplified by PCR with the cosmid vector pAxcw (supra) as the template, with [$\alpha$-$^{32}$P] dCTP using the BcaBEST™ Labeling Kit (Takara Shuzo). The sequences of primers used for PCR are shown below (numerical values in parentheses indicate the base numbers of adenovirus type 5 and sequence numbers):

```
L1:    5'-primer 5'-ACTGCGGCTAATGGTGACTGAGACA-3'      (12,818-12,842/SEQ ID NO: 3)

3'-primer 5'-CGGCCGCGCGATGCAAGTAGTCCAT-3'      (13,440-13,416/SEQ ID NO: 4)

L2:    5'-primer 5'-AGCGGCGCGGAAGAGAACTCCAACG-3'      (15,098-15,122/SEQ ID NO: 5)

3'-primer 5'-ATGCCCAGGGCCTTGTAAACGTAGG-3'      (15,834-15,810/SEQ ID NO: 6)

L3:    5'-primer 5'-GGGCTCCAGTGAGCAGGAACTGAAA-3'      (21,735-21,759/SEQ ID NO: 7)

3'-primer 5'-CTGCGCACTGTGGCTGCGGAAGTAG-3'      (22,305-22,281/SEQ ID NO: 8)

L5:    5'-primer 5'-GACCCCTCACAGTGTCAGAAGGAAA-3'      (31,484-31,508/SEQ ID NO: 9)

3'-primer 5'-GCCAAACAGCCTTTAACAGCCAAAA-3'      (32,378-32,354/SEQ ID NO: 10)

pIX:   5'-primer 5'-ATGAGCACCAACTCGTTTGATG-3'         (3,609-3,630/SEQ ID NO: 11)

3'-primer 5'-TGTTTTAAACCGCATTGGGAGGGGA-3'      (4,035-4,011/SEQ ID NO: 12)

Iva2:  5'-primer 5'-AAGAACTTGGAGACGCCCTTGTGA-3'       (4,554-4,577/SEQ ID NO: 13)

3'-primer 5'-TGTGGGACCGCCTGGAACTGCTTG-3'       (5,181-5,158/SEQ ID NO: 14)

E4:    5'-primer 5'-GGCAGTGGTCTCCTCAGCGA-3'           (33,301-33,320/SEQ ID NO: 15)

3'-primer 5'-TGAGGAAGTGTATGCACGTG-3'           (33,800-33,781/SEQ ID NO: 16)

E2A:   5'-primer 5'-TGCTCAGGGCGAACGGAGTCAACTTTGGTA-3' (22,769-22,798/SEQ ID NO: 17)

3'-primer 5'-GTATGCGGACGCAAGAGGAAGAGGAAGAGC-3' (23,584-23,555/SEQ ID NO: 18)
```

After 5 μg of each RNA was electrophoresed on a 1% agarose gel, it was blotted on a nylon filter (Hybond-N+, Amersham) by the capillary transfer method and then subjected to UV crosslinking. After the filter was stained with a 0.02% methylene blue solution to confirm the position of 28S and 18S RNA, 50 ml of buffer A (0.5 M $Na_2HPO_4$ (pH 7.2) 7% SDS/1 mM EDTA) was added and prehybridized at 65° C. for 2 hours. Then, 50 ml of buffer A containing 12.5 ng of the $^{32}$P-labeled probe was added to the filter, which was then hybridized at 65° C. overnight. Furthermore, 200 ml of buffer B (40 mM $Na_2HPO_4$ (pH 7.2)/1% SDS) was added thereof, and after the filter was washed twice at 65° C., it was subjected to autoradiography.

(3) Result

Figure 4:
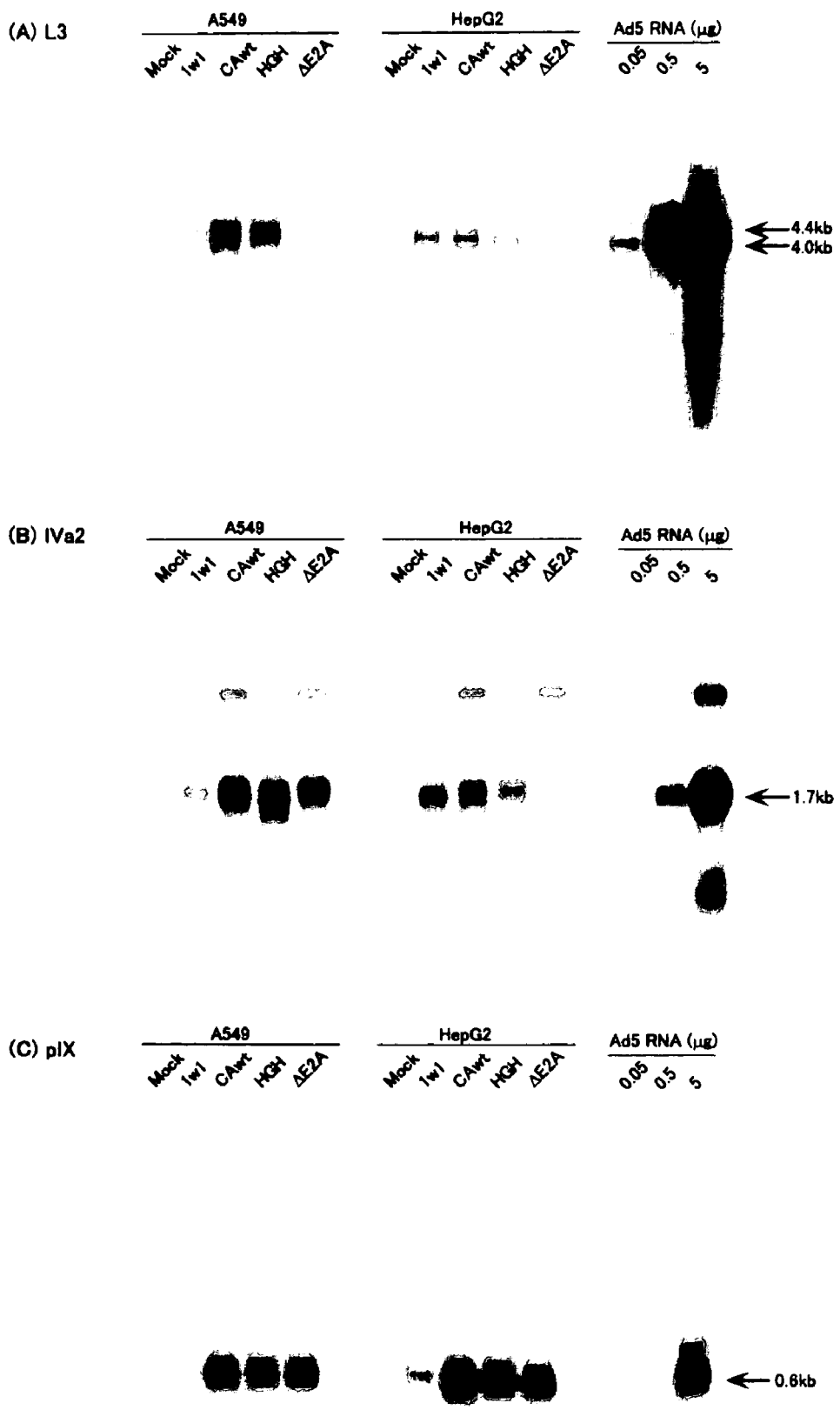
FIG. 4 is a photograph showing the result of Northern blotting. A549 cells or HepG2 cells were infected with each of the adenovirus vectors shown below at a moi of 100, and 24 hours later RNA was prepared from the cells. After electrophoresis of five μg of each RNA, (A) L3 RNA, (B) IVa2 RNA, and (C) pIX RNA were detected by Northern blotting. Symbols above the gel represent: Mock: mock infection, lwl: Axlwl, CAwt: AxCAwt, HGH: Ax1CAHGH, ΔE2A: ΔE2A-CAHGH. Arrows and figures on the righthand side of the gel show the position and the size of the desired band. Three lanes on the right labeled Ad5 are the positive control. HepG2 cells were infected with viruses derived from an adenovirus type 5 wild strain (Ad5-dlX: Saito I. et al., J. Virol. 54: 711-719 (1985)) in which the E3 gene is only deleted at a moi of 10, and 24 hours later RNA was prepared, and the amount of RNA shown in the figure was subjected to electrophoresis.

Results of Northern blotting are shown in FIG. 4A to C, and the summary of the results is shown in Table 1. In A549 cells, the expressions of a major late gene, which is controlled by the adenovirus major late promoter (MLP), for example the L3 gene containing hexon, were evidently decreased in the Axlwl-infected cells as compared to the AxCAwt-infected cells, and was similarly decreased in the ΔE2A-CAHGH-infected cells (FIG. 4A). Furthermore, in HepG2 cells, the expression of the L3 gene was only decreased in the ΔE2A-CAHGH-infected infected cells. Though the data are not shown, results for other major late genes such as the L2 gene and the L5 gene were similar to that for the L3 gene, and no induction of expression by the CAG promoter was noted for these late genes.

Though the expression of the E2A gene was naturally decreased in the ΔE2A-CAHGH-infected cells, no difference of the E2A gene expression was seen between in the Axlwl-infected cells and in the AxCAwt-infected cells, and the E2A gene was expressed at a similar level in both of the virus-infected cells. These were no differences in all vector-infected cells for the expression of the E4 gene, and the E4 gene was expressed at a similar level in all of the virus-infected cells (data not shown). Thus, it was demonstrated that neither the expression of E2A gene nor the expression of the E4 gene are induced by the CAG promoter.

In the HepG2 cells, the expression of the IVa2 gene which is a delayed early gene not controlled by MLP was not different between the Axlwl-infected cells and the AxCAwt-infected cells, and was expressed to a similar degree in both cells. On the other hand, in the A549 cells, the expression of the IVa2 gene was decreased only in the Axlwl-infected cells (FIG. 4B).

Also, the expression of the L1 gene, one of the late genes controlled by MLP, was similar to that of the IVa2 gene and the result was different in the HepG2 cells and in the A549 cells (see Table 1).

On the other hand, the expression of the protein IX gene (hereinafter referred to as pIX gene), a delayed early gene as is the IVa2 gene not controlled by MLP, gave a similar result for the A549 cells and for the HepG2 cells. Thus, the expression of the pIX gene was not decreased in the ΔE2A-CAHGH-infected cells, and only in the Axlwl-infected cells, expression was evidently decreased (FIG. 4C).

From the above results, the gene which exhibited the similar expression pattern to the changes of serum GPT levels in both of the A549 cells and the HepG2 cells, i.e., of which expression is almost the same in the AxCAwt-, Ax1CAHGH-, and ΔE2A-CAHGH-infected cells and is decreased only in the Axlwl-infected cells was the pIX gene. This indicated that the gene of which expression is induced by the CAG promoter and which causes inflammation is the pIX gene.

TABLE 1

| Gene | Cell line | Result of Northern Blotting | | | |
|------|-----------|-------|--------|----------|------------|
|      |           | Axlwl | AxCAwt | Ax1CAHGH | ΔE2A-CAHGH |
| L1   | A549      | −     | +      | +        | +/−        |
|      | HepG2     | +     | +      | +        | −          |
| L2   | A549      | −     | +      | +        | −          |
|      | HepG2     | +     | +      | +        | −          |

TABLE 1-continued

Result of Northern Blotting

| Gene | Cell line | Axlwl | AxCAwt | Ax1CAHGH | ΔE2A-CAHGH |
|---|---|---|---|---|---|
| L3 | A549 | − | + | + | − |
|  | HepG2 | + | + | + | − |
| L5 | A549 | − | + | + | − |
|  | HepG2 | + | + | + | − |
| E2A | A549 | + | + | + | − |
|  | HepG2 | + | + | + | − |
| E4 | A549 | + | + | + | + |
|  | HepG2 | + | + | + | + |
| Iva2 | A549 | − | + | + | + |
|  | HepG2 | + | + | + | + |
| pIX | A549 | − | + | + | + |
|  | HepG2 | − | + | + | + |
| Changes in serum GPT levels | | → | ↑ | ↑ | ↑ |

EXAMPLE 7

Confirmation of Induction of pIX Gene Expression by the CMV Promoter

It was investigated whether the expression of the pIX gene is induced by the CMV promoter in a similar manner to the CAG promoter. As a recombinant adenovirus in which a CMV promoter has been inserted, a recombinant adenovirus AdCMVlacZ (Osada S. et al., Kidney Int. 55: 1234-1240 (1999)) was used in which a CMV promoter and an *Escherichia coli* lacZ gene have been inserted in the orientation toward right side at the E1 gene deletion site of adenovirus type 5. As the control virus in which a CAG promoter has been inserted, AxCAwt shown in Example 6 was used.

A549 cells were infected with AdCMVlacZ or AxCAwt in a manner similar to that described in Example 6, and 24 hours later RNA was recovered. However, moi of infection was moi 6 or moi 2 for AdCMVlacZ and moi 300 or moi 100 for AxCAwt. Northern blotting was carried out using the pIX probe shown in Example 6.

Figure 5:
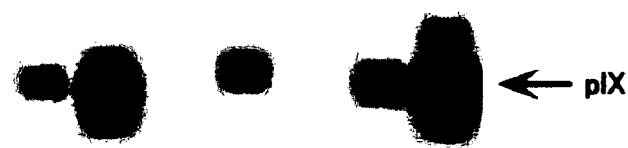
FIG. 5 is a photograph showing the result of Northern blotting of a protein IX (pIX) gene. A549 cells were infected with AxCAwt or AdCMVlacZ at the moi shown in the figure, and 24 hours later RNA was prepared from the cells. Five μg of RNA from each of them was subjected to electrophoresis, and then pIX RNA was detected by Northern blotting. Abbreviations in the figure represent: Mock: mock infection, CAG: AxCAwt, CMV: AdCMVlacZ. Three lanes on the right labeled Ad5 is the positive control. A549 cells were infected with Ad5-dlX (see FIG. 4) at a moi of 10, and 24 hours later RNA was prepared, and the amount of RNA shown in the figure was subjected to electrophoresis.

The result is shown FIG. 5. In the cells infected with AdCMVlacZ at a moi of 6, the pIX gene was expressed at a level equal to or higher than that of the cells infected with AxCAwt at a moi of 100. Since the moi at the time of infection of the two viruses is different, and the direction of insertion of the promoter is different, and the distance from the promoter to the pIX gene is different, the degree of strength of induction of pIX gene expression by the CAG promoter and the CMV promoter cannot be compared. However, in the AdCMVlacZ-infected cells that has inserted therein the CMV promoter, the pIX gene was expressed at a lower moi, and therefore it was revealed that the expression of the pIX gene can be induced by the CMV promoter too.

EXAMPLE 8

Investigation on the Presence or Absence of Induction of pIX Gene Expression by the SRα Promoter and the EF-1α Promoter It was investigated whether the expression of the pIX gene is induced by a foreign promoter containing no CMV promoter. The promoters used for the study were SRα promoter (Takebe Y. et al., Mol. Cell Biol. 8: 466-472 (1988)) and the EF-1α promoter (Kim D. W. et al., Gene 91: 217-223 (1990)), and adenovirus vectors (AxSRlacZ-L and AxEFlacZ-L) in which each promoter and *E. coli* lacZ gene have been inserted in the orientation toward left side. As the positive control, an adenovirus vector AxCAwt (see Example 5) in which only the CAG promoter has been inserted has been inserted and an adenovirus vector (AxCAlacZ-L) in which the CAG promoter and the *E. coli* lacZ gene have been inserted in the orientation toward left side were used. The method of constructing AxSRlacZ-L, AxEFlacZ-L and AxCAlacZ-L has been disclosed by Saito et al. (Japanese Unexamined Patent Publication (Kokai) No. 7-298877), in which AdexlSRlacZ-L is identical with AxSRlacZ-L, AdexlEFlacZ-L with AxEFlacZ-L, and AdexlCAlacZ-L with AxCAlacZ-L, respectively. As the negative control, an adenovirus vector Axlwl (see Example 5) having no foreign promoter inserted therein was used. Furthermore, an adenovirus vector (AdCMVlacZ) having the CMV promoter used in Example 7 was investigated again.

A549 cells were infected with the above six adenovirus vectors (AxSRlacZ-L, AxEFlacZ-L, AxCAlacZ-L, AdCMVlacZ, AxCAwt, Axlwl) at a moi of 30 or 100, and 24 hours later, RNA was recovered and subjected to Northern blotting using the pIX probe (for details of methods, see Example 6).

Figure 6:
FIG. 6 is a photograph showing the result of Northern blotting of the pIX gene. A549 cells were infected with each of the adenovirus vectors shown in the figure at a moi of 30 or 100, and 24 hours later RNA was prepared from the cells. Five μg of RNA from each of them was subjected to Northern blotting to detect pIX RNA.

The result is shown in FIG. 6. In the cells infected with an adenovirus vector (AdCMVlacZ) having a CMV promoter, the pIX gene was expressed indeed, and the amount of expression thereof was equal to or higher than that of the cells infected with an adenovirus vector (AxCAlacZ-L and AxCAwt) having a CAG promoter using as a positive control.

On the other hand, in the cells infected with an adenovirus vector (AxEFlacZ-L) having an EF-1α promoter, no expression of the pIX gene was observed at all. In the cells infected with an adenovirus vector (AxSRlacZ-L) having a SRα promoter, the expression of the pIX gene was observed.

The above results demonstrated that the expression of the pIX gene by a foreign promoter is associated with specificity of the promoter, and that there exist foreign promoters such as the EF-1α promoter which do not induce the expression of the pIX gene at all. Furthermore, it was demonstrated that what induces the expression of the pIX gene is mainly the CMV IE enhancer since the common portion of the CAG promoter and the CMV promoter is only the CMV IE enhancer.

EXAMPLE 9

Investigation on the Inflammation-inducing Ability of Adenovirus Vectors having Different Promoters In order to prove that the induction of pIX gene expression by a foreign promoter is correlated with inflammation which occurs at the administration of an adenovirus vector to an animal, four vectors (AxEFlacZ-L, AxCAlacZ-L, AdCMVlacZ, and Axlwl) among the adenovirus vectors used in Example 8 were administered to C57BL/6 mice, and the degree of inflammation was compared with serum GPT levels as an index.

The adenovirus was administered via the tail vein (five animals per group) at $1 \times 10^9$ PFU (except for AdCMVlacZ), $3 \times 10^8$ PFU, and $1 \times 10^8$ PFU, and blood was collected three days before, and 3, 5, 7, 10, 14, 21, 28, and 35 days after the administration, and GPT levels were determined. Details of each method were carried out according to the method described in Example 3.

Figure 7:
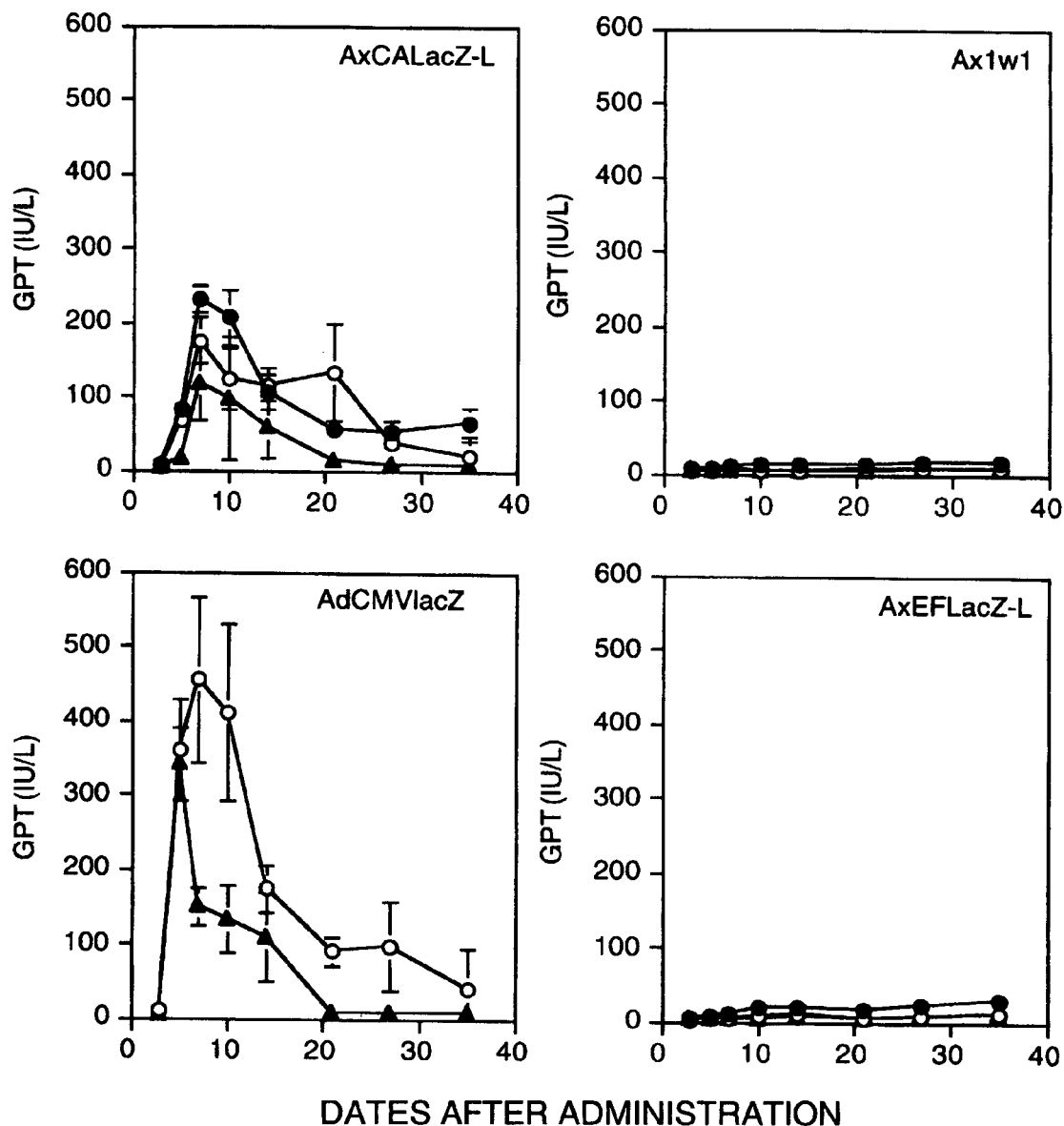
FIG. 7 is a graph showing mean values of daily changes in serum GPT levels of C57BL/6 mice which were injected with adenovirus vectors having a different promoter (five mice per group). In the figure, is a group injected with $1 \times 10^9$ PFU, ○ is a group injected with $3 \times 10^8$ PFU, ▲ is a group injected with $1 \times 10^8$ PFU of the vector.

The result is shown in FIG. 7. In the mice treated with AdCMVlacZ having a CMV promoter, serum GPT levels elevated more than in the mice treated with AxCAlacZ-L having a CAG promoter, and the degree of inflammation was correlated with the amount expressed of the pIX gene shown in Example 8. On the other hand, in the mice treated with AxEFlacZ-L having an EF-1α promoter, there was little increase in serum GPT levels which were the same level as the mice treated with AxIwI having no foreign promoter.

The above results demonstrated that the expression of the pIX gene is directly correlated with inflammation after in vivo administration, i.e. an adenovirus vector having a promoter that does not induce the expression of the pIX gene does not induce inflammation, and that the induction of pIX gene expression by a foreign promoter is the cause of inflammation.

EXAMPLE 10

Preparation of Anti-pIX Antibody and the Detection of Protein IX (1) Cloning of the Protein IX (pIX) Gene In order to clone the coding region of the pIX gene of human adenovirus type 5 (Ad5) by the PCR method, the following procedure was carried out. With the above cosmid vector pAxcw as the template, PCR reaction was performed using the primers of the following sequences. 5'-primers were designed so as to include the nucleotide sequence at positions 3585-3605 of Ad5 and an EcoRI recognition site, and 3'-primers were designed so as to include the base sequence at positions 4034-4015 of Ad5 and a XhoI recognition site.

```
5'-end primer
5'-TAGAATTCTGTTTTGCAGCAGCCGCCGCC-3' (SEQ ID NO: 19)
    EcoRI

3'-end primer
5'-TACTCGAGGTTTTAAACCGCATTGGGAG-3' (SEQ ID No. 20)
    XhoI    End
```

A PCR reaction was performed using a Pfx DNA polymerase (GIBCO BRL) to amplify a 470 bp DNA fragment containing the coding region of the pIX gene. The commercially available plasmid vector pcDNA3.1(+) (Invitrogen) has a multi cloning site downstream of the CMV promoter. Thus, the PCR-amplified 470 bp DNA fragment was co-digested with EcoRI and XhoI, and then inserted in between the EcoRI site and the XhoI site in the multi cloning site of pcDNA3.1 (+) to obtain a pIX-expressing plasmid pCMV-IX (5.9 kb). By sequencing the portion containing the coding region of the pIX gene of this pCMV-IX, and the sequence was confirmed to be identical with the existing sequence (GenBank: Accession No. M73260).

(2) Preparation of a pIX-Fusion Protein

As an antigen to obtain anti-pIX antibody, a fusion protein of pIX and glutathione S-transferase (GST) was prepared.

1) Construction of an Expression Plasmid for a pIX-Fusion Protein

Plasmid pCMV-IX was co-digested with EcoRI and XhoI to obtain a 470 kb DNA fragment containing a pIX gene. The commercially available plasmid vector pGEX-5X-1 (Amersham Pharmacia Biotech) which is constructed to express a GST-fusion protein in E. coli has a multi cloning site at the C-terminal end of GST. Thus, the 470 bp DNA fragment obtained from pCMV-IX was inserted in between the EcoRI site and the XhoI site in the multi cloning site of pGEX-5X-1 to obtain a GST-pIX-expressing plasmid pGST-IX (5.4 kb).

2) Preparation of a pIX-fusion Protein

An E. coli strain JM109 was transformed with the plasmid pGST-IX. Since GST-pIX expressed by the transformant was insoluble, GST-pIX was purified according to the purification method for the protein in inclusion body. First, after culturing the transformed E. coli in 40 ml of the LB medium at 37° C. overnight, 800 ml of the LB medium was added and was further cultured for 1 hour. After adding IPTG (isopropyl-β-D-thiogalactopyranoside) (a final concentration of 0.2 mM) and culturing for 6 hours, the cells were harvested. The cells were washed with PBS, suspended in 20 ml of the lysis buffer (50 mM Tris-HCl (pH 8.0)/1 mM EDTA/100 mM NaCl) containing lysozyme (1 mg/ml), incubated at room temperature for 20 minutes, and then 1 ml of the lysis buffer containing 10% sodium deoxycholate was added to lyse the cells. Then the lysate was added with 100 µl of 1M $MgCl_2$ solution, 100 µl of 1M $MnCl_2$ solution, and 20 µl of DNase I solution (70 U/µl), and incubated at 37° C. for 15 minutes followed by centrifugation (11,850×g) for 15 minutes. After centrifugation, the supernatant was discarded, and the precipitate was washed twice with 20 ml of the lysis buffer containing 0.5% Triton X-100/10 mM EDTA, and then the precipitate was suspended in 1 ml of PBS. The solution was added with an equal amount of 6M urea, and incubated at room temperature for 1 hour followed by centrifugation (11,850×g) for 15 minutes. After centrifugation, the supernatant was discarded, and the precipitate was suspended in 2 ml of PBS. The solution was added with 6 ml of 8M guanidine hydrochloride (a final concentration of 6M), and after centrifugation (11,850×g) for 15 minutes, the supernatant was recovered. Using the supernatant as purified GST-pIX, anti-pIX antibody was prepared.

(3) Preparation of Anti-pIX Antibody

The purified GST-pIX, as it contains 6M guanidine hydrochloride, was immunized to rabbits (Japanese White).

Immunization and blood collecting was referred to Asahi Techno Glass Corporation. 0.2-0.4 mg of antigen (GST-pIX) was immunized five times every two weeks to two rabbits. One week after the fourth immunization, blood was partially collected to confirm that the titer of antibody against GST-pIX was raised sufficiently by the ELISA method, and then one week after the fifth immunization, the whole blood was collected to obtain antiserum (#1 and #2).

Then, it was confirmed that these antisera reacted with pIX by Western blotting. As the positive control containing pIX, the following two samples were used. One is the cells recovered about one day after A549 cells were infected with a virus derived from the adenovirus type 5 wild strain (Ad5-dlX: Saito I. et al., J. Virol. 54: 711-719 (1985)) at a moi of 10 in which the E3 gene has only been deleted, and the other is the purified adenovirus particles. As the negative control, A549 cells that are not infected with adenovirus were used.

Each sample was subjected to SDS polyacrylamide gel electrophoresis (SDS-PAGE) under a reduced condition, and then blotted to a nitrocellulose membrane (Hybond ECL, Amersham Pharmacia Biotech). The membrane was blocked in 5% skim milk, to which a 1000-fold diluted antiserum or a preimmune serum was added, and incubated overnight at 4° C. After washing the membrane, peroxidase-conjugated $F(ab')_2$ fragment donkey anti-rabbit Ig antibody (Amersham Pharmacia Biotech, Cat. NA9340) was added, and incubated at room temperature for 1 hour. Furthermore, after washing the membrane, a chemiluminescence detection reagent (ECL Plus detection reagent, Amersham Pharmacia Biotech) was added thereto, and the membrane was exposed to an X-ray film.

Figure 8:
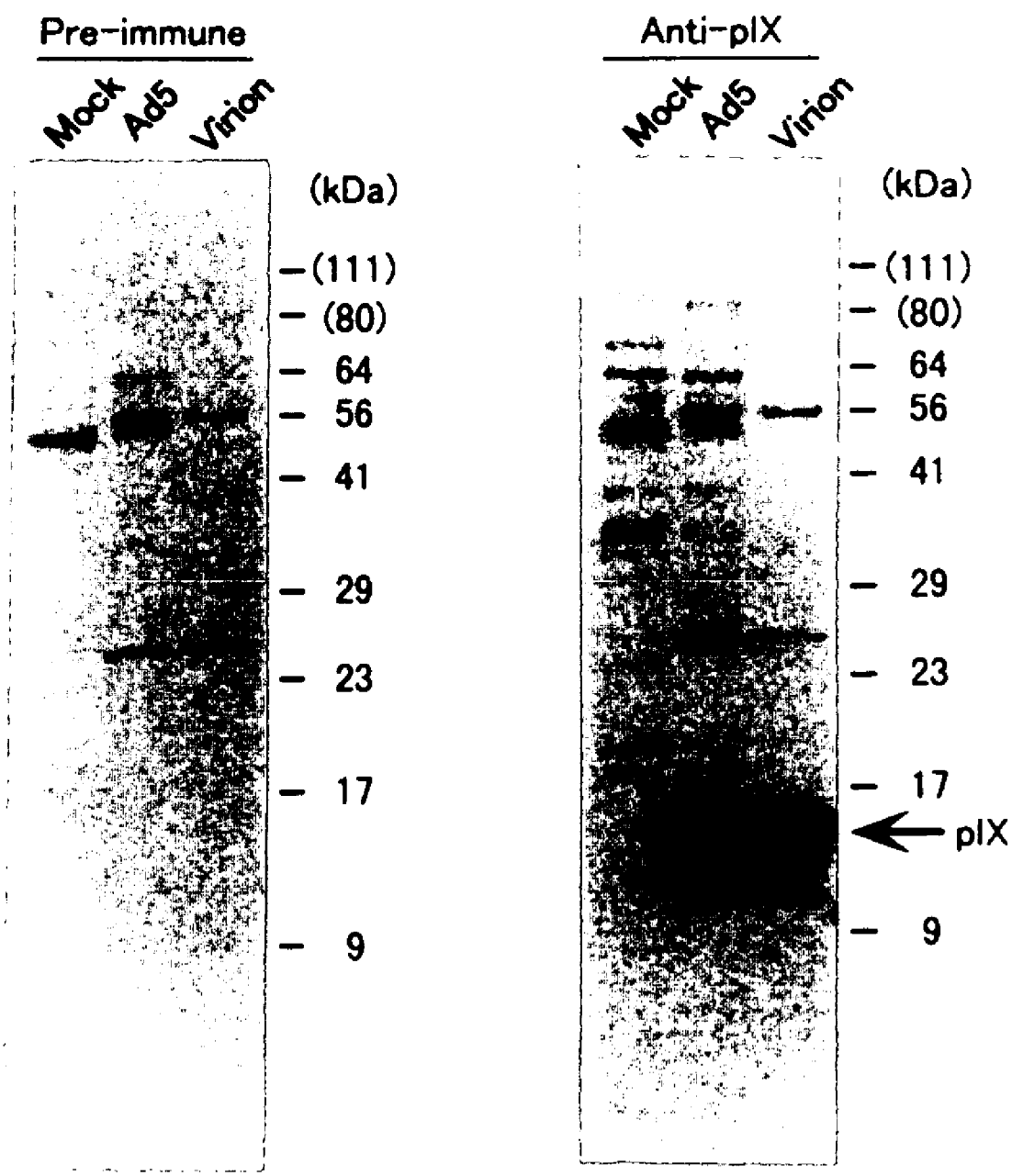
FIG. 8 is a photograph showing the result of Western blotting that used antiserum raised against the pIX-fusion protein (GST-pIX). A549 cells were infected with Ad5-dlX (see FIG. 4) at a moi of 10, and the cells were harvested about one day later, and dissolved in the SDS sample buffer. The cell lysate or purified virus particles ($7.5 \times 10^7$ PFU) were subjected to SDS-polyacrylamide gel electrophoresis (SDS-PAGE) under a reduced condition, followed by Western blotting to thereby detect pIX using anti-pIX antiserum #1 (Anti-pIX) or pre-immune serum (Pre-immune). Abbreviations in the figure represent: Mock: non-infected cells, Ad5: Ad5-dIX-infected cells, Virion: purified virus particles. Numerical values on the right hand side of the figure mean the molecular weight of molecular weight markers. As the molecular weight markers, the prestained molecular weight marker (GIBCO BRL, Cat. No. 10748-010) was used, and the molecular weight used was corrected from the mobility of the unstained molecular weight marker (New England Biolabs, Cat. No. P7702S). Numerical values in parentheses are values that are not corrected with the unstained molecular weight marker.

Among the two antisera, the result of antiserum #1, as example, is shown in FIG. 8. When an antiserum after immunization was used, an about 14 kDa band corresponding to the molecular weight of pIX was clearly detected in the lanes in which the Ad5-dlX-infected cells and purified virus particles were applied, whereas this band was not detected in the lane in which A549 cells not infected with the virus were applied. Furthermore, when preimmune serum was used, this 14 kDa band was not detected in any of the lanes at all. A similar result was obtained for #2 antiserum, though the data are not shown. The above result confirmed that the 14 kDa band detected by these antisera is derived from pIX. Thus, these antisera were used as anti-pIX antibody in the following experiments.

(4) Detection of pIX of which Expression was Induced by the CAG Promoter

In Examples 6-8, it was demonstrated by Northern blotting that the expression of pIX RNA was induced by the CAG promoter. Accordingly, it was investigated by Western blotting whether the expression of pIX can also be induced not only at the RNA level but at the protein level.

Figure 9:
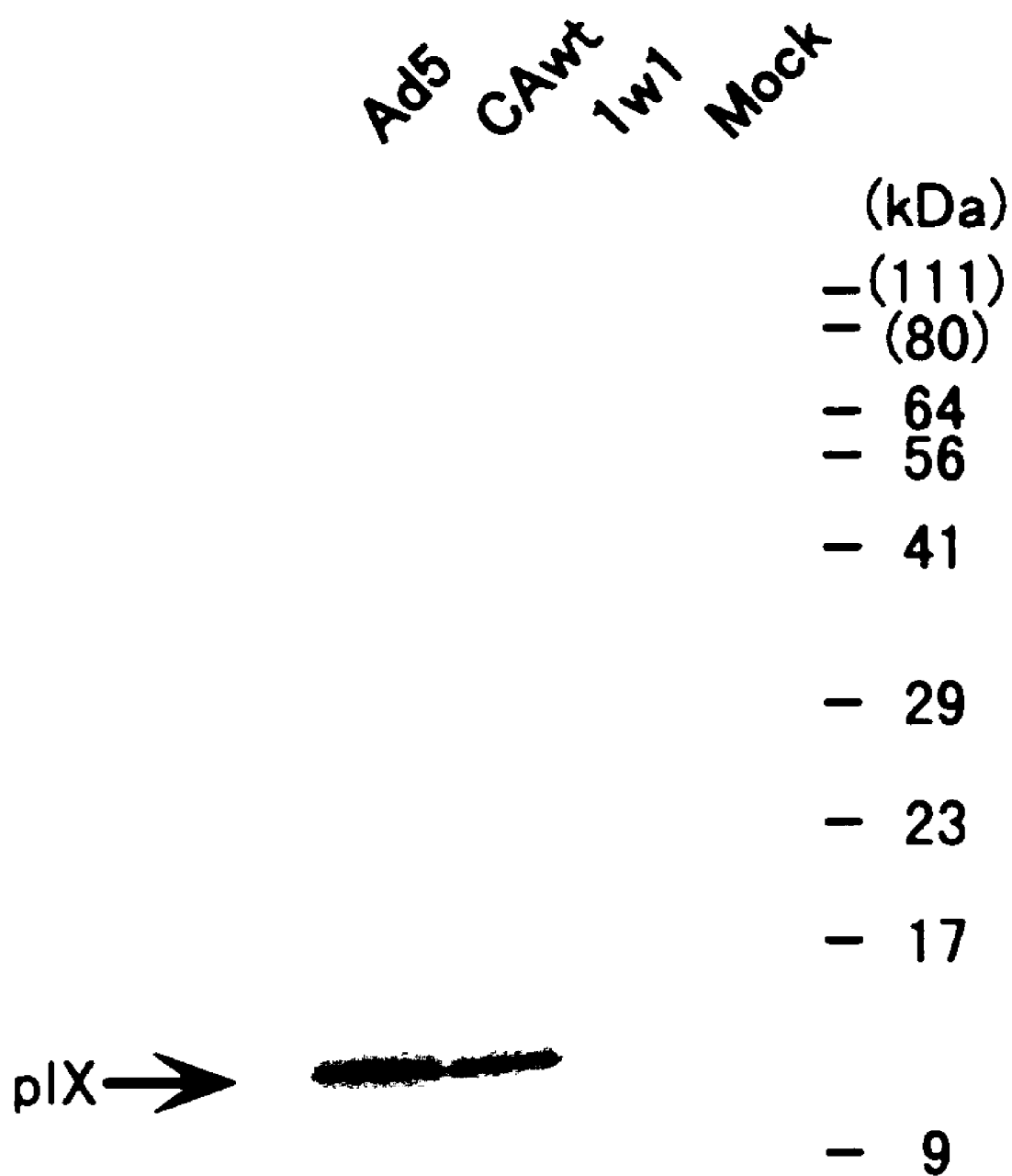
FIG. 9 is a photograph showing the result of Western blotting of pIX. A549 cells were infected with AxCAwt (moi 100), Awlwl (moi 100) or Ad5-dIX (moi 10), and the cells were harvested about one day later, and dissolved in the SDS sample buffer. After SDS-PAGE, Western blotting was carried out to detect pIX. Abbreviations in the figure represent: Ad5: Ad5-dIX-infected cells, CAwt: AxCAwt-infected cell, lwl: Awlwl-infected cells, Mock: non-infected cells. Numerical values on the right hand side of the figure mean molecular weight (see FIG. 8).

A549 cells were infected with an adenovirus vector AxCAwt (see Example 5) in which a CAG promoter has only been inserted or an adenovirus vector Axlwl (see Example 5) in which no foreign promoter has been inserted at a moi of 100, and one day later the cells were recovered. As the positive control, the A549 cells which were infected with Ad5-dIX at a moi of 10 and were recovered one day later, were used. In a method similar to that described in the above (3), Western blotting was performed to detect pIX with anti-pIX antibody (#1). As shown in FIG. 9, 14 kDa pIX was detected in the AxCAwt-infected cells as in the Ad5-dIX-infected cells. On the other hand, this 14 kDa band was not observed at all in the Axlwl-infected cells. This confirmed that the expression of pIX is induced by the CAG promoter at the protein level, too.

EXAMPLE 11

Construction of a pIX-relocated Adenovirus Vector

A pIX-relocated adenovirus vector was constructed by the following procedures (1) to (3):
(1) Construction of a Recombinant Adenovirus Vector (Ax4pIX) Having a pIX Gene Inserted Therein Between the Upstream Region of the E4 Gene and the 3'-end ITR In order to clone the region including the full-length of the pIX gene of human adenovirus type 5 (Ad5), the following procedure was carried out. With a cosmid vector pAxcw (supra) as the template containing the majority of the adenovirus type 5 genome other than the E1 gene and the E3 gene, a PCR reaction was performed using the following primers. Restriction enzyme recognition sites were added to each primer.

E4 gene and the 3'-end ITR, the following procedure was carried out. The cosmid vector pAx4w is a vector that contains 2.6-98.0 m.u. (the E3 gene is deleted) of the genome of adenovirus type 5 and 98.0-100 m.u. of the genome of adenovirus type 2, and has a cloning site, restriction enzyme SwaI site, between the upper region of the promoter of the E4 gene and 3'-end ITR (99.3 m.u.) (Miyake S. et al., Proc. Natl. Acad. Sci. USA 93: 1320-1324 (1996), in said reference pAx4w has been described as pAdex4w). Plasmid pUCfpIX was digested with RsaI to obtain an about 0.6 kb DNA fragment containing a pIX gene. This 0.6 kb DNA fragment was inserted into the SwaI site of the cosmid vector pAx4w to obtain cosmids pAx4pIXL and pAx4pIXR. In pAx4pIXL the pIX gene has been inserted in the orientation toward left side, and in pAx4pIXR the pIX gene has been inserted toward right side.

Figure 10:
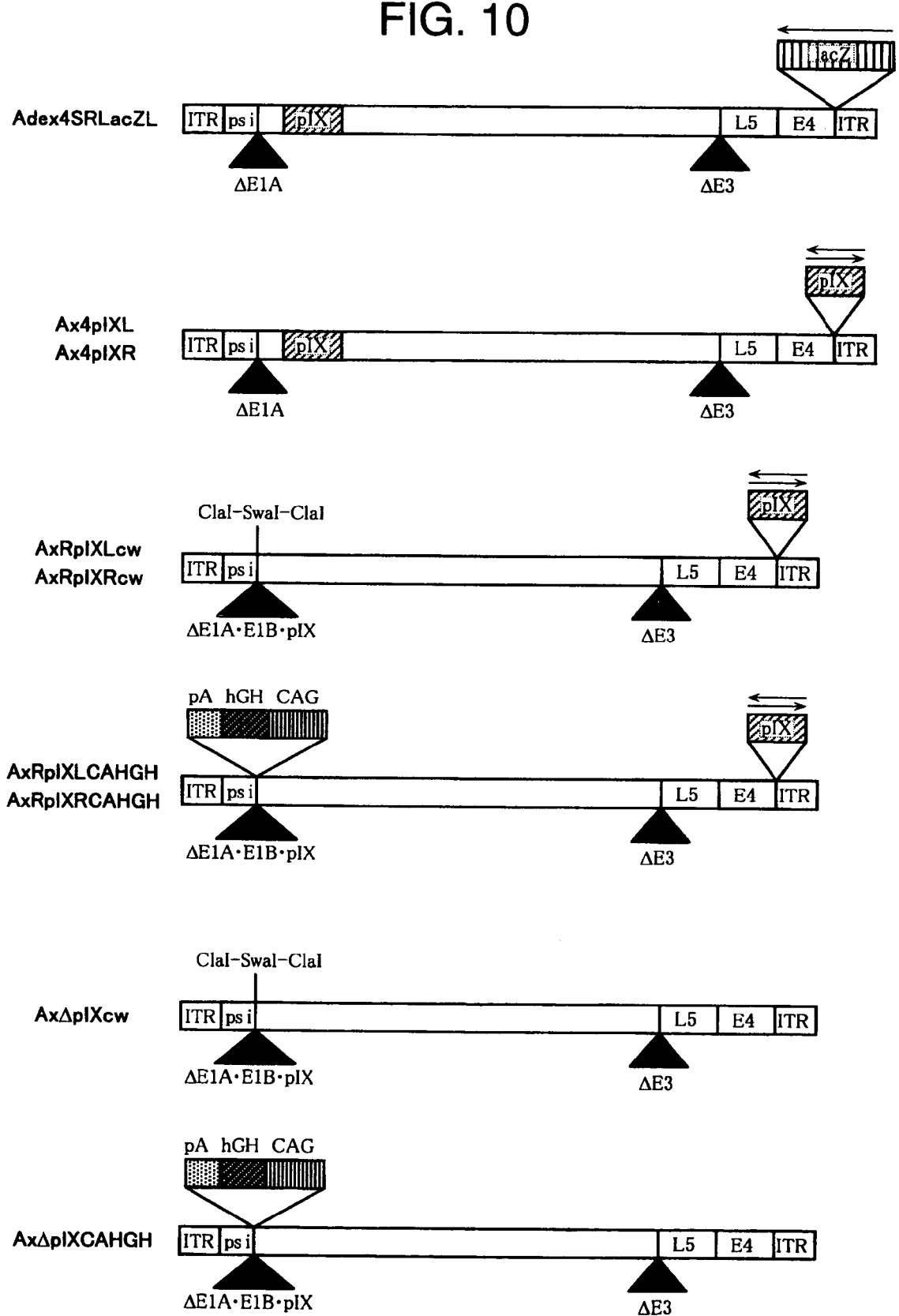
FIG. 10 is a schematic diagram showing the structure of a protein IX-relocated adenovirus vector, pIX-deleted adenovirus vector and the like. In the figure, lacZ represents an expression unit of E. coli lacZ gene, pIX represents the protein IX gene, psi represents a packaging signal, CAG represents the CAG promoter, hGH represents human growth hormone cDNA, and pA represents the poly(A) sequence. An arrow indicates the direction of transcription for each gene.

Finally, in order to construct a recombinant adenovirus in which a pIX gene has been inserted in between the upstream region of the E4 gene and the 3'-end ITR, the following procedure was carried out. The recombinant adenovirus vector Adex4SRlacZL (see Miyake S. et al., Proc. Natl. Acad. Sci. USA 93: 1320-1324 (1996) and FIG. 10) is a replication-defective adenovirus vector which is derived from adenovirus type 5 (the E1A gene and the E3 gene have been deleted) and which has inserted therein the expression unit of $E.\ coli$ lacZ gene in the orientation toward left said at the position of 99.3 m.u., the same position as pAx4w. From Adex4SRlacZL, an adenovirus DNA-terminal protein complex (DNA-TPC) was prepared, and then this DNA-TPC was co-digested with restriction enzymes AseI and EcoRI. Since in the genomic DNA of Adex4SRlacZL, there are several AseI sites and EcoRI sites in the right half of the genome containing the expression unit of the lacZ gene, the digestion of DNA-TPC of Adex4SRlacZL with the both enzymes yields a DNA-TPC in which the right half of the genome has been digested. 293 cells were transformed with this restriction-digested DNA-TPC and the cosmid pAx4pIXL or pAx4pIXR. By digesting the genomic DNA of the generated recombinant adenovirus with restriction enzymes BspEI and PmlI, the virus clone of interest was identified, and a recombinant adenovirus Ax4pIXL or Ax4pIXR (FIG. 10) in which the expression unit of the $E.\ coli$ lacZ gene of Adex4SRlacZL has been replaced with the pIX gene was obtained. Ax4pIXL and Ax4pIXR are recombinant adenoviruses which have the pIX gene at two sites (the original position (9.7-11.2 m.u.) of the pIX gene and between the upstream region of the E4 gene and the 3'-end ITR). The difference in the structure of between Ax4pIXL and Ax4pIXR is only the direction of insertion of the pIX

```
5'-end primer
5'-CCTGAATTC GTACTGAAATGTGTGGGCGTGGCTTA-3'        (SEQ ID NO: 21)(Ad5: 3513-3536)
      EcoRI  RsaI 3'-end primer
5'-CCTGGATCC GTAC ATTAATTGCTTGATCCAAATCCAAACAG-3' (SEQ ID No. 22)(Ad5: 4076-4054)
      BamHI  RsaI AseI
```

An about 0.6 kb DNA fragment containing the PCR-amplified pIX gene was co-digested with EcoRI and BamHI, and then inserted in between the EcoRI site and the BamHI site in the multi cloning site of the commercially available plasmid pUC19 to obtain a plasmid pUCfpIX (3.3 kb). By sequencing of the insert portion containing the pIX gene of this pUCfpIX, and the sequence was confirmed to be identical with the existing sequence (GenBank: Accession No. M73260).

Then, in order to construct a cosmid vector in which a pIX gene has been inserted in between the upstream region of the gene between the E4 gene and ITR, and Ax4pIXL is a recombinant adenovirus in which the pIX gene has been inserted therein in the orientation toward left side, and Ax4pIXR is a recombinant adenovirus in which the pIX gene has been inserted therein in the orientation toward right side.

Figure 11:
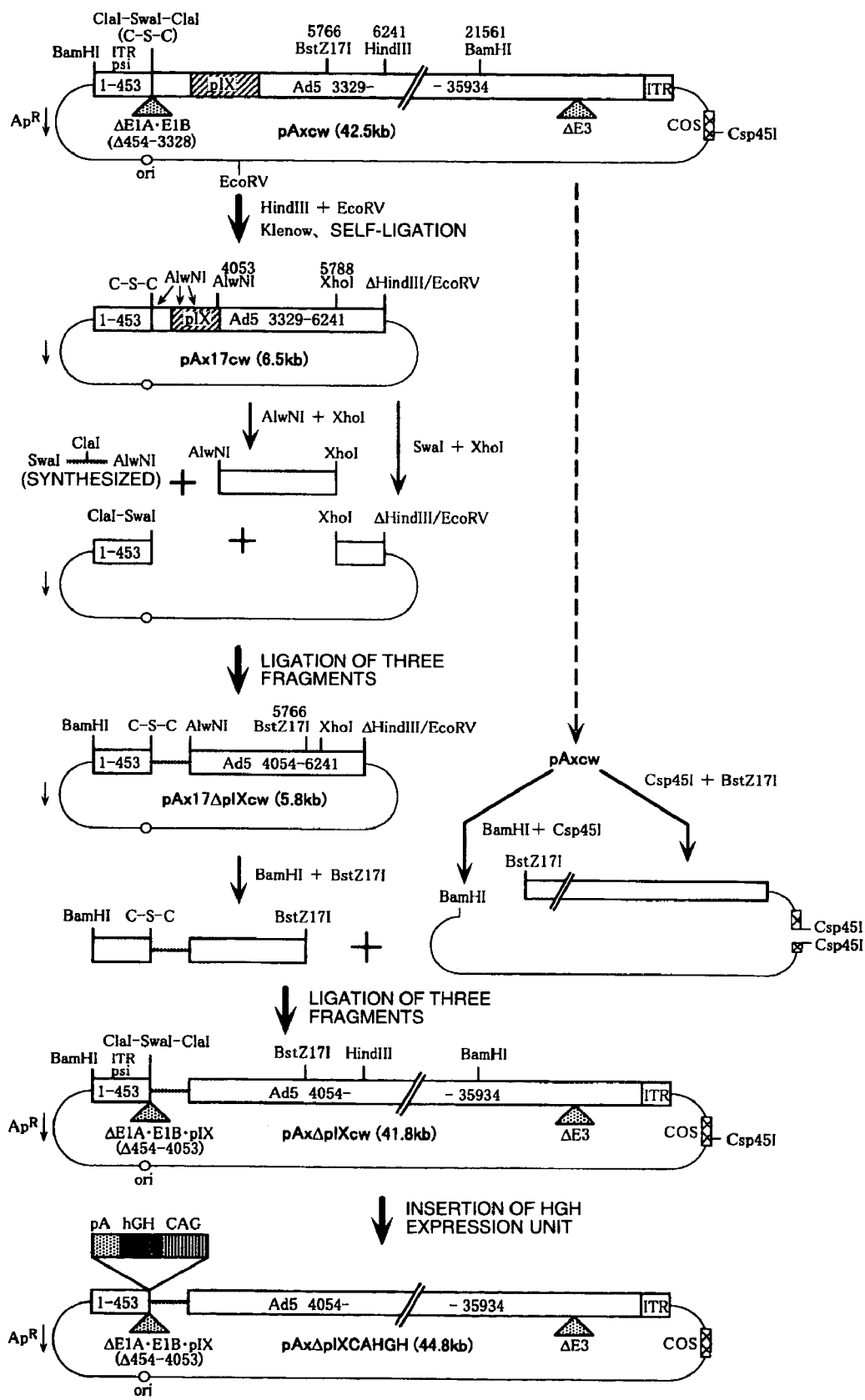
FIG. 11 is a schematic diagram showing the method of constructing a cosmid vector pAxΔpIXcw and pAxΔpIX-CAHGH. In the figure, the open box indicates the human adenovirus type 5 genome, and the thin-lined part indicates an E. coli-derived DNA sequence. Numerical values on the restriction enzymes indicate the nucleotide number at the recognition site of each restriction enzyme in the human adenovirus type 5. $AP^R$ represents ampicillin-resistant gene, ori represents E. coli origin of replication, and COS represents the COS site of λ phage.

(2) Construction of a Cosmid Vector (pAxΔpIXcw) having an Adenovirus Vector Genome in which the E1A, the E1B, and the pIX Genes have been Deleted In order to construct a plasmid containing 17% of the left end of the adenovirus type 5 genome containing a pIX gene, the following procedure was carried out. The above-mentioned cosmid vector pAx4w (FIG. 11) is a vector that contains the majority of adenovirus type 5 genome other than the E1 gene (Δ454-3328) and the E3 gene (A28592-30470). pAxcw was digested with HindIII and EcoRV, and then blunt-ended with a Klenow enzyme followed by self-ligation to obtain a plasmid pAx17cw (6.5 kb: FIG. 11). pAx17cw is a plasmid that contains about 17% (1-453, 3329-6241) of the left end of adenovirus type 5 other than the E1 gene.

In order to construct a pIX gene-deleted plasmid from pAx17cw, the following three DNA fragments (a) to (c) were prepared:
(a) An about 4.0 kb DNA fragment containing no pIX gene, obtained by digesting pAx17cw with SwaI and XhoI,
(b) An about 1.7 kb DNA fragment corresponding to positions 4054-5788 of the adenovirus type 5 genome, obtained by digesting pAx17cw with AlwNI and XhoI,
(c) A double stranded DNA fragment designed to have a sequence of the SwaI-digested fragment-ClaI recognition site-SalI recognition site-NruI recognition site-AlwNI-digested fragment, obtained by phosphorylating the 5'-end of the synthetic DNA having the following sequence and then by annealing it:

(SwaI)

ClaI SalI NruI (AlwNI)

```
5'-AAATCGATT GTCGAC TCGCGA CAGACT-   (SEQ ID NO: 23)
3'

3'-TTTAGCTAA CAGCTG AGCGCT GTC-5'    (SEQ ID NO: 24)
```

The above three fragments, (a), (b) and (c), were ligated thereby to obtain a plasmid pAx17ΔpIXcw (5.8 kb: FIG. 11) in which the E1A, E1B, and pIX genes have been deleted (Δ454-4053).

Then, in order to construct a cosmid vector in which the sequence between the BamHI site and the BstZ17I site of the cosmid vector pAxcw has been the BstZ17I site of the plasmid pAx17ΔpIXcw, the following three DNA fragments (d) to (f) were prepared:
(d) An about 2.2 kb DNA fragment containing SwaI recognition site, obtained by digesting pAx17ΔpIXcw with BamHI and BstZ17I,
(e) An about 10 kb DNA fragment containing no adenovirus genomic DNA, obtained by digesting pAxcw with BamHI and Csp45I,
(f) An about 30 kb DNA fragment containing an adenovirus genomic DNA, obtained by digesting pAxcw with Csp45I and BstZ17I.

The above three fragments, (d), (e) and (f), were ligated thereby to obtain a cosmid vector pAxΔpIXcw (41.8 kb: FIG. 11) having an adenovirus genome in which the E1A, E1B, and pIX gene have been deleted Finally, in order to construct a cosmid vector in which the expression unit of human growth hormone (hGH) has been inserted into the E1A, E1B, and pIX gene deletion site of the cosmid vector pAΔpIXcw, the following procedure was carried out:

A cosmid pAx1CAHGH (Example 1) having a hGH expression unit in which hGH cDNA was ligated downstream of the CAG promoter was digested with a restriction enzyme PmeI to obtain an about 3.0 kb DNA fragment containing a hGH expression unit. This DNA fragment was inserted into the SwaI site of the cosmid vector pAΔpIXcw to obtain a cosmid pAΔpIXCAHGH (44.8 kb: FIG. 11).

(3) Construction of a Protein IX-relocated Adenovirus Vector

In order to construct a protein IX-relocated adenovirus vector by homologous recombination between a recombinant adenovirus Ax4pIXL or Ax4pIXR described in (1) and the cosmid vector pAxΔpIXCAHGH described in (2), the following procedure was carried out. From Ax4pIXL and Ax4pIXR, an adenovirus DNA-TPC was prepared, and then each DNA-TPC was digested with a restriction enzyme EcoT22I. Since there are a several EcoT22I sites in the left half of the genomic DNA of Ax4pIXL and Ax4pIXR, digestion with EcoT22I yields a DNA-TPC in which the left half of the genome has been digested. 293 cells were transformed with the DNA-TPC of the EcoT22I-digested Ax4pIXR and the cosmid pAxΔpIXCAHGH. By digesting the genomic DNA of the generated recombinant adenovirus with restriction enzymes (XhoI, NruI, BspEI etc.), the virus clone of interest is identified. As a result, a pIX-relocated adenovirus vector (AxRpIXRCAHGH, FIG. 10) can be obtained in which the pIX gene is not present at the original position (9.7-11.2 m.u.) of the pIX gene, and the pIX gene has been relocated to between the upstream region of the E4 gene and the 3'-end ITR. Similarly, a pIX-relocated adenovirus vector (AxRpIXLCAHGH, FIG. 10) can be obtained by transformation of 293 cells with the DNA-TPC of the EcoT22I-digested Ax4pIXL and the cosmid pAxΔpIXCAHGH. The difference in the structure of between AxRpIXRCAHGH and AxRpIXLCAHGH is only the direction of insertion of the pIX gene, and AxRpIXRCAHGH is a recombinant adenovirus in which the pIX gene has been inserted therein in the orientation toward right side, and AxRpIXLCAHGH is a recombinant adenovirus in which the pIX gene has been inserted therein in the orientation toward left side.

EXAMPLE 12

Construction of pIX-expressing Cell Line

In order to use for the production of a pIX-deleted adenovirus vector, 293 cells were transformed to construct a pIX-expressing cell line Using a pIX-expressing plasmid pCMV-IX constructed in Example 10-(1), 293 cells were transformed by the lipofection method (FuGENET™ 6 Transfection reagent: Roche Diagnostics Corp.). Since a neomycin-resistant gene has been inserted into pCMV-IX, the medium was replaced to one containing 600 μg/ml of G418 sulfate (Geneticin: GIBCO BRL) three days after transformation, and after the transformed cells were further cultured for 13 days, the cells were cloned. For any 10 clones among the G418-resistant cell lines, the expression of the pIX gene was examined by Northern blotting. As a result, it was confirmed that the pIX gene has been expressed in four clones (#2, #5, #6, #10). Thus, in order to examine the stability of expression of the pIX gene for these four clones, these four clones were subcultured to passage 30, during which RNA was prepared at every five passages, and the expression of the pIX gene was confirmed by Northern blotting (FIG. 12). As a result, it was confirmed that the pIX gene can be stably expressed to at least passage 30 in all four clones, though the amount of expression of the pIX gene is different with the clone.

Figure 13:
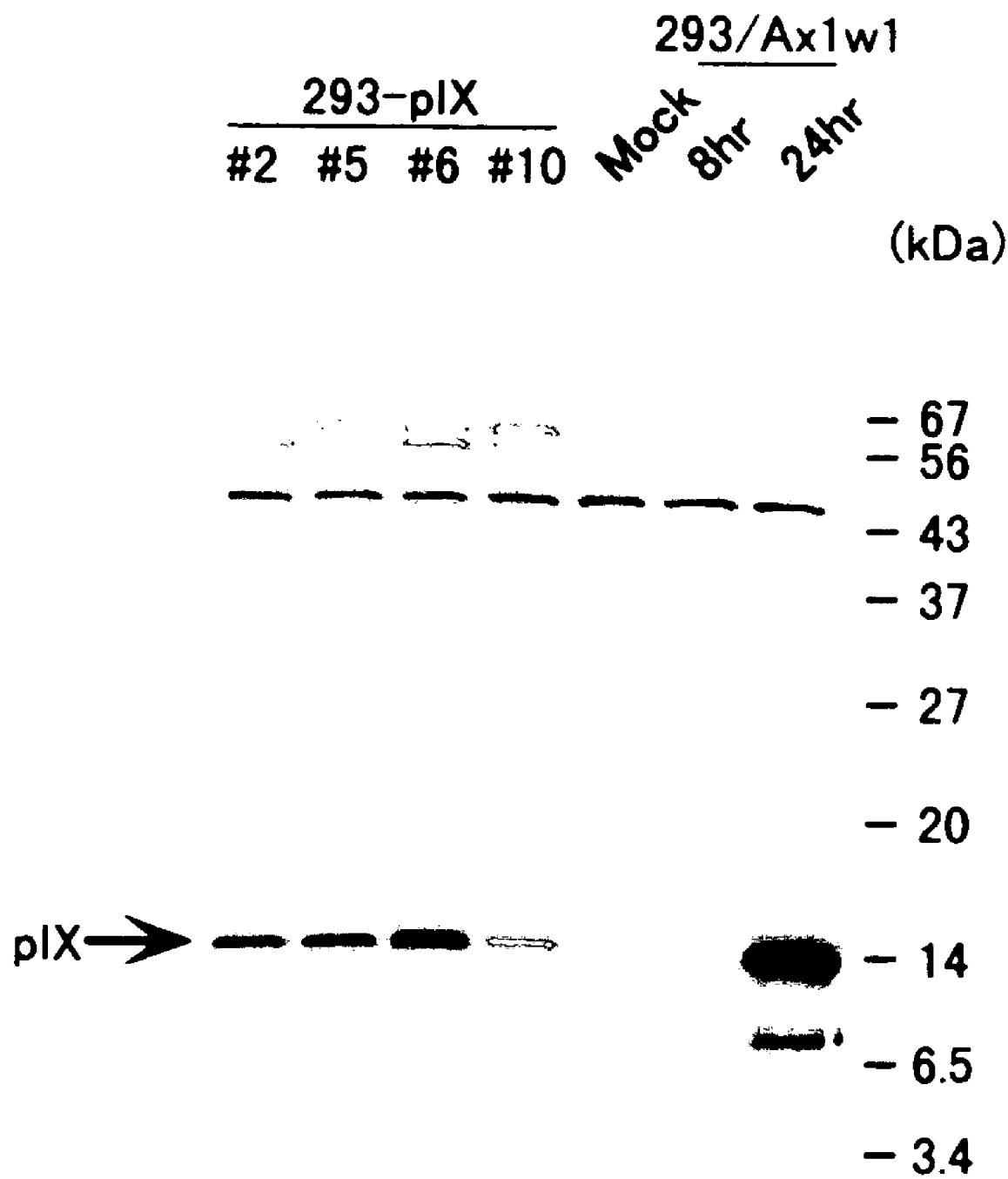
FIG. 13 is a photograph showing the result of Western blotting of pIX of the pIX-expressing cell lines. Four clones (#2, #5, #6, #10) of the pIX-expressing cell lines were subcultured to passage 25, and then dissolved in the SDS sample buffer. After SDS-PAGE, Western blotting was carried out to detect pIX. Three lanes on the right hand side are the negative control and the positive control. For details, see FIG. 12. As the molecular weight markers, unstained molecular weight marker (New England Biolabs, Cat. No. P7702S) was used.

Furthermore, using the cells at passage 25, the expression of pIX was confirmed at the protein level as well using the Western blotting described in Example 10-(3). In this experiment and in the experiment of FIG. 12, 293 cells infected with the adenovirus vector Axlwl in which no foreign promoter has been inserted was used as the positive control. Even if the cells such as A549 cells that are not expressing the adenovirus E1A or E1B genes are infected with Axlwl, pIX is hardly expressed either at the RNA level (FIG. 4, FIG. 6), or at the protein level (FIG. 9). However, when the 293 cells expressing the E1A and the E1B genes are infected with Axlwl, they correspond to a usual replication cycle of the E1 gene-deleted first generation adenovirus vector and express an sufficient amount of pIX. As shown in FIG. 13, it was confirmed that all four clones expressed pIX even at the protein level, though the amount is somewhat less than the amount of pIX expressed by the Axlwl-infected 293 cells.

The above result clearly indicates that four clones (#2, #5, #6, #10) of pIX-expressing cell lines that express pIX constitutively and stably were obtained.

EXAMPLE 13

Construction of a pIX-deleted Adenovirus Vector

In order to construct a pIX-deleted adenovirus vector by homologous recombination between an adenovirus vector AxCAwt used in Example 5 and a pIX-deleted cosmid vector pAxΔpIXCAHGH, the following procedure was carried out.

From AxCAwt an adenovirus DNA-TPC was prepared, and then digested with EcoT22I. 293 cells or the pIX-expressing cell line described in Example 12 are transformed with this DNA-TPC and the cosmid vector pAxΔpIXCAHGH. By digesting the genomic DNA of the generated recombinant adenovirus with restriction enzymes (ClaI, NruI, SalI etc.), the virus clone of interest is identified, and a pIX-deleted adenovirus vector AxΔpIXCAHGH (FIG. 10) can be obtained. AxΔpIXCAHGH is a recombinant adenovirus derived from adenovirus type 5 in which the E1A, E1B and the pIX genes have been deleted (Δ454-4053) and the E3 gene has also been deleted (Δ28592-30470).

When a pIX-deleted adenovirus vector was obtained by transformation of a pIX-expressing cell line, the pIX-expressing cell line is used for the passage and preparation of viruses in large scales. On the other hand, when a pIX-deleted adenovirus vector was obtained by transformation of 293 cells, the pIX-expressing cell line is used for the preparation of viruses in large scales.

Then the pIX-deleted adenovirus vector is purified, and virus particles are prepared, for which the presence of a normal amount of pIX protein in the virus particles is confirmed by Western blotting using anti-pIX antibody.

EXAMPLE 14

Investigation on the Presence or Absence of Inflammation by the Administration of a pIX-relocated Adenovirus Vector and a pIX-deleted Adenovirus Vector In order to confirm that inflammation has been alleviated for the pIX-relocated adenovirus vector and the pIX-deleted adenovirus vector, an in vivo experiment is carried out by measuring serum GPT levels as an index of inflammation as described in Examples 3 and 5. The adenovirus vectors tested are as follows:

hGH-expressing pIX-relocated adenovirus vector:
AxRpIXRCAHGH, AxRpIXLCAHGH (Example 11)
hGH-expressing pIX-deleted adenovirus vector:
AxΔpIXCAHGH (Example 13)
hGH-expressing first generation adenovirus vector:
Ax1CAHGH (Example 5)
a first generation adenovirus vector in which no foreign gene has been inserted: Axlwl (Example 5)

Experimental methods including as mouse straines and the dosage of adenovirus vectors are carried out according to the method described in Example 3.

As a result, in Ax1CAHGH-administered mice, serum GPT levels become significantly increased as in Examples 3 and 5. However, in AxRpIXRCAHGH-, AxRpIXLCAHGH-, and AxΔpIXCAHGH-administered mice, serum GPT levels are not increased at all as in the Axlwl-administered mice. The above result indicates that pIX-relocated adenovirus vectors and pIX-deleted adenovirus vectors hardly causes inflammation even if they are administered in vivo.

INDUSTRIAL APPLICABILITY

The present invention can provide highly safe adenovirus vectors for gene therapy in which the expression of virus protein has been inhibited and inflammation has been alleviated.

---

The invention claimed is:

1. A recombinant adenovirus vector, for which inflammation during in vivo administration thereof is alleviated as compared with a first generation adenovirus vector lacking the E1 gene, said recombinant adenovirus vector having the following characteristics:
   (a) deletion of the adenovirus E1A and E1B genes;
   (b) retention of at least ORF3 of the adenovirus E4 gene;
   (c) presence of a foreign gene under control of a foreign promoter;
   (d) relocation of the adenovirus protein IX gene to a position in said vector at which expression of said protein IX gene is not induced by said foreign promoter, said position being at least 18 kb or more from the foreign promoter, and either: (i) between the adenovirus L3 gene and the adenovirus E2A gene, or (ii) between the E4 gene and the 3' ITR:
   wherein said vector encodes a virus particle having infectivity and thermal stability equivalent to that of an adenovirus wild-type strain.

2. The recombinant adenovirus vector according to claim 1, wherein the foreign gene under the control of the foreign promoter has been inserted into the E1A and E1B gene deletion site.

3. The recombinant adenovirus vector according to claim 1, further comprising a deletion of all or part of an additional adenovirus gene.

4. The recombinant adenovirus vector according to claim 1, further comprising a deletion of all or part of the adenovirus E3 gene.

5. The recombinant adenovirus vector according to claim 1, further comprising a deletion of all or part of the adenovirus E2A gene.

6. The recombinant adenovirus vector according to claim 1, wherein in characteristic (b) only ORF3 of the E4 gene has been retained.

7. The recombinant adenovirus vector according to claim 1, wherein the protein IX gene has been relocated to a position between the adenovirus L3 gene and the adenovirus E2A gene.

8. The recombinant adenovirus according to claim 1, wherein the protein IX gene has been relocated to a position between the E4 gene and the 3" ITR.

9. The recombinant adenovirus vector according to claim 1, wherein the foreign promoter contains an element derived from an animal virus.

10. The recombinant adenovirus vector according to claim 9, wherein the foreign promoter contains a cytomegalovirus (CMV) enhancer.

11. The recombinant adenovirus vector according to claim 10, wherein the foreign promoter is a CMV promoter.

12. The recombinant adenovirus vector according to claim 10, wherein the foreign promoter is a CAG promoter.

13. The recombinant adenovirus vector according to claim 9, wherein the foreign promoter is a Rous sarcoma virus (RSV) promoter or a SRα promoter.

14. The recombinant adenovirus vector according to claim 1, wherein said recombinant adenovirus vector is a human adenovirus.

15. The recombinant adenovirus vector according to claim 14, wherein said recombinant adenovirus vector is a type 2 adenovirus or a type 5 adenovirus.

16. The recombinant adenovirus vector according to claim 2, wherein said recombinant adenovirus vector comprises an additional deletion of all or part of an adenovirus gene.

17. The recombinant adenovirus vector according to claim 9, wherein said animal virus is a mammalian virus.

* * * * *

SEQUENCE LISTING

<160> NUMBER OF SEQ ID NOS: 25

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 1
tggctagctc acctagcggc aatggct                                          27

<210> SEQ ID NO 2
<211> LENGTH: 26
<212> TYPE: DNA
<213> ORGANISM: Artificial Sequence
<220> FEATURE:

```
<223> OTHER INFORMATION: Description of Artificial Sequence: Primer

<400> SEQUENCE: 2
caggcatgcc acccgggcag ctagaa                                          26

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 3
actgcggcta atggtgactg agaca                                           25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 4
cggccgcgcg atgcaagtag tccat                                           25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 5
agcggcgcgg aagagaactc caacg                                           25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 6
atgcccaggg ccttgtaaac gtagg                                           25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 7
gggctccagt gagcaggaac tgaaa                                           25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 8
ctgcgcactg tggctgcgga agtag                                           25
```

```
<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 9
gacccctcac agtgtcagaa ggaaa                                        25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 10
gccaaacagc ctttaacagc caaaa                                        25

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
atgagcacca actcgtttga tg                                           22

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 12
tgttttaaac cgcattggga gggga                                        25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 13
aagaacttgg agacgccctt gtga                                         24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 14
tgtgggaccg cctggaactg cttg                                         24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer
```

```
<400> SEQUENCE: 15
ggcagtggtc tcctcagcga                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
tgaggaagtg tatgcacgtg                                               20

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 17
tgctcagggc gaacggagtc aactttggta                                    30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 18
gtatgcggac gcaagaggaa gaggaagagc                                    30

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 19
tagaattctg ttttgcagca gccgccgcc                                     29

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 20
tactcgaggt tttaaaccgc attgggag                                      28

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 21
cctgaattcg tactgaaatg tgtgggcgtg gctta                              35

<210> SEQ ID NO 22
<211> LENGTH: 41
```

-continued

```
<212> TYPE: DNA
<213> ORGANISM: Artificial Sequence
<220> FEATURE:
<223> OTHER INFORMATION: Description of Artificial Sequence: Primer

<400> SEQUENCE: 22
cctggatccg tacattaatt gcttgatcca aatccaaaca g                    41

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aaatcgattg tcgactcgcg acagact                                    27

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctgtcgcgag tcgacaatcg attt                                       24

<210> SEQ ID NO 25
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Pro Pro Thr Met Glu Asp Val Ser Ser Pro Ser Pro Ser Pro Pro
 1               5                  10                  15

Pro Pro Arg Ala Pro Pro Lys Lys Arg
            20                  25
```